(12) United States Patent
Srinivasan et al.

(10) Patent No.: US 11,864,850 B2
(45) Date of Patent: Jan. 9, 2024

(54) PATH-BASED NAVIGATION OF TUBULAR NETWORKS

(71) Applicant: Auris Health, Inc., Redwood City, CA (US)

(72) Inventors: Subashini Srinivasan, San Carlos, CA (US); Hedyeh Rafii-Tari, Mountain View, CA (US); Ritwik Ummalaneni, San Mateo, CA (US); David Paul Noonan, San Francisco, CA (US); Prasanth Jeevan, San Mateo, CA (US)

(73) Assignee: Auris Health, Inc., Redwood City, CA (US)

( * ) Notice: Subject to any disclaimer, the term of this patent is extended or adjusted under 35 U.S.C. 154(b) by 0 days.

(21) Appl. No.: 17/155,963

(22) Filed: Jan. 22, 2021

(65) Prior Publication Data

US 2021/0137617 A1    May 13, 2021

Related U.S. Application Data

(63) Continuation of application No. 16/424,188, filed on May 28, 2019, now Pat. No. 10,898,286.

(Continued)

(51) Int. Cl.
*A61B 34/30* (2016.01)
*A61B 34/20* (2016.01)
*A61B 34/10* (2016.01)

(52) U.S. Cl.
CPC .............. *A61B 34/30* (2016.02); *A61B 34/20* (2016.02); *A61B 2034/107* (2016.02); *A61B 2034/2051* (2016.02); *A61B 2034/301* (2016.02)

(58) Field of Classification Search
CPC ... A61B 34/30; A61B 34/20; A61B 2034/107; A61B 2034/2051; A61B 2034/301
(Continued)

(56) References Cited

U.S. PATENT DOCUMENTS

| 4,745,908 A | 5/1988 | Wardle |
| 5,273,025 A | 12/1993 | Sakiyama et al. |

(Continued)

FOREIGN PATENT DOCUMENTS

| CN | 101147676 A | 3/2008 |
| CN | 101222882 A | 7/2008 |

(Continued)

OTHER PUBLICATIONS

EP Search Report for appl No. 19811516.4, dated Jan. 26, 2022, 7 pages.

(Continued)

*Primary Examiner* — Michael P Nghiem
(74) *Attorney, Agent, or Firm* — Chang & Hale LLP

(57) ABSTRACT

Provided are systems and methods for path-based navigation of tubular networks. In one aspect, the method includes receiving location data from at least one of a set of location sensors and a set of robot command inputs, the location data being indicative of a location of an instrument configured to be driven through a luminal network. The method also includes determining a first estimate of the location of the instrument at a first time based on the location data, determining a second estimate of the location of the instrument at the first time based on the path, and determining the location of the instrument at the first time based on the first estimate and the second estimate.

30 Claims, 26 Drawing Sheets

Related U.S. Application Data

(60) Provisional application No. 62/678,970, filed on May 31, 2018.

(58) Field of Classification Search
USPC .......................................................... 702/94
See application file for complete search history.

(56) References Cited

U.S. PATENT DOCUMENTS

| | | |
|---|---|---|
| 5,526,812 A | 6/1996 | Dumoulin et al. |
| 5,550,953 A | 8/1996 | Seraji |
| 5,831,614 A | 11/1998 | Tognazzini et al. |
| 5,935,075 A | 8/1999 | Casscells et al. |
| 6,038,467 A | 3/2000 | Bliek et al. |
| 6,047,080 A | 4/2000 | Chen et al. |
| 6,059,718 A | 5/2000 | Taniguchi et al. |
| 6,063,095 A | 5/2000 | Wang et al. |
| 6,167,292 A | 12/2000 | Badano et al. |
| 6,203,493 B1 | 3/2001 | Ben-Haim |
| 6,246,784 B1 | 6/2001 | Summers et al. |
| 6,246,898 B1 | 6/2001 | Vesely et al. |
| 6,332,089 B1 | 12/2001 | Acker et al. |
| 6,425,865 B1 | 7/2002 | Salcudean et al. |
| 6,466,198 B1 | 10/2002 | Feinstein |
| 6,490,467 B1 | 12/2002 | Bucholz et al. |
| 6,553,251 B1 | 4/2003 | Lähdesmäki |
| 6,665,554 B1 | 12/2003 | Charles et al. |
| 6,690,963 B2 | 2/2004 | Ben-Haim et al. |
| 6,690,964 B2 | 2/2004 | Bieger et al. |
| 6,812,842 B2 | 11/2004 | Dimmer |
| 6,899,672 B2 | 5/2005 | Chin et al. |
| 6,926,709 B2 | 8/2005 | Bieger et al. |
| 7,180,976 B2 | 2/2007 | Wink et al. |
| 7,206,627 B2 | 4/2007 | Abovitz et al. |
| 7,233,820 B2 | 6/2007 | Gilboa |
| 7,386,339 B2 | 6/2008 | Strommer et al. |
| 7,756,563 B2 | 7/2010 | Higgins et al. |
| 7,850,642 B2 | 12/2010 | Moll et al. |
| 7,901,348 B2 | 3/2011 | Soper et al. |
| 8,155,403 B2 | 4/2012 | Tschirren et al. |
| 8,190,238 B2 | 5/2012 | Moll et al. |
| 8,298,135 B2 | 10/2012 | Ito et al. |
| 8,317,746 B2 | 11/2012 | Sewell et al. |
| 8,394,054 B2 | 3/2013 | Wallace et al. |
| 8,460,236 B2 | 6/2013 | Roelle et al. |
| 8,821,376 B2 | 9/2014 | Folkowsky |
| 8,858,424 B2 | 10/2014 | Hasegawa et al. |
| 8,929,631 B2 | 1/2015 | Pfister et al. |
| 9,014,851 B2 | 4/2015 | Wong et al. |
| 9,125,639 B2 | 9/2015 | Mathis et al. |
| 9,138,129 B2 | 9/2015 | Diolaiti |
| 9,183,354 B2 | 11/2015 | Baker et al. |
| 9,186,046 B2 | 11/2015 | Ramamurthy et al. |
| 9,272,416 B2 | 3/2016 | Hourtash et al. |
| 9,289,578 B2 | 3/2016 | Walker et al. |
| 9,459,087 B2 | 10/2016 | Dunbar et al. |
| 9,504,604 B2 | 11/2016 | Alvarez |
| 9,561,083 B2 | 2/2017 | Yu et al. |
| 9,603,668 B2 | 3/2017 | Weingarten et al. |
| 9,622,827 B2 | 4/2017 | Yu et al. |
| 9,629,682 B2 | 4/2017 | Wallace et al. |
| 9,636,184 B2 | 5/2017 | Lee et al. |
| 9,710,921 B2 | 7/2017 | Wong et al. |
| 9,713,509 B2 | 7/2017 | Schuh et al. |
| 9,717,563 B2 | 8/2017 | Tognaccini et al. |
| 9,727,963 B2 | 8/2017 | Mintz et al. |
| 9,737,371 B2 | 8/2017 | Romo et al. |
| 9,737,373 B2 | 8/2017 | Schuh |
| 9,744,335 B2 | 8/2017 | Jiang |
| 9,763,741 B2 | 9/2017 | Alvarez et al. |
| 9,788,910 B2 | 10/2017 | Schuh |
| 9,844,412 B2 | 12/2017 | Bogusky et al. |
| 9,867,635 B2 | 1/2018 | Alvarez et al. |
| 9,918,681 B2 | 3/2018 | Wallace et al. |
| 9,931,025 B1 | 4/2018 | Graetzel et al. |
| 9,949,749 B2 | 4/2018 | Noonan et al. |
| 9,955,986 B2 | 5/2018 | Shah |
| 9,962,228 B2 | 5/2018 | Schuh et al. |
| 9,980,785 B2 | 5/2018 | Schuh |
| 9,993,313 B2 | 6/2018 | Schuh et al. |
| 10,016,900 B1 | 7/2018 | Meyer et al. |
| 10,022,192 B1 | 7/2018 | Ummalaneni |
| 10,046,140 B2 | 8/2018 | Kokish et al. |
| 10,080,576 B2 | 9/2018 | Romo et al. |
| 10,123,755 B2 | 11/2018 | Walker et al. |
| 10,130,345 B2 | 11/2018 | Wong et al. |
| 10,136,950 B2 | 11/2018 | Schoenefeld |
| 10,136,959 B2 | 11/2018 | Mintz et al. |
| 10,143,360 B2 | 12/2018 | Roelle et al. |
| 10,143,526 B2 | 12/2018 | Walker et al. |
| 10,145,747 B1 | 12/2018 | Lin et al. |
| 10,149,720 B2 | 12/2018 | Romo |
| 10,159,532 B1 | 12/2018 | Ummalaneni |
| 10,159,533 B2 | 12/2018 | Moll et al. |
| 10,169,875 B2 | 1/2019 | Mintz et al. |
| 10,219,874 B2 | 3/2019 | Yu et al. |
| 10,231,793 B2 | 3/2019 | Romo |
| 10,231,867 B2 | 3/2019 | Alvarez et al. |
| 10,244,926 B2 | 4/2019 | Noonan et al. |
| 10,278,778 B2 | 5/2019 | State et al. |
| 10,285,574 B2 | 5/2019 | Landey et al. |
| 10,299,870 B2 | 5/2019 | Connolly et al. |
| 10,639,114 B2 | 5/2020 | Schuh et al. |
| 10,743,751 B2 | 8/2020 | Landey et al. |
| 10,765,487 B2 | 9/2020 | Ho et al. |
| 10,898,286 B2 * | 1/2021 | Srinivasan ............. A61B 34/20 |
| 11,058,493 B2 * | 7/2021 | Rafii-Tari ............... A61B 34/20 |
| 11,160,615 B2 * | 11/2021 | Rafii-Tari ............... A61B 34/10 |
| 2001/0021843 A1 | 9/2001 | Bosselmann et al. |
| 2001/0039421 A1 | 11/2001 | Heilbrun et al. |
| 2002/0065455 A1 | 5/2002 | Ben-Haim et al. |
| 2002/0077533 A1 | 6/2002 | Bieger et al. |
| 2002/0120188 A1 | 8/2002 | Brock et al. |
| 2003/0105603 A1 | 6/2003 | Hardesty |
| 2003/0125622 A1 | 7/2003 | Schweikard et al. |
| 2003/0181809 A1 | 9/2003 | Hall et al. |
| 2003/0195664 A1 | 10/2003 | Nowlin et al. |
| 2004/0047044 A1 | 3/2004 | Dalton |
| 2004/0072066 A1 | 4/2004 | Cho et al. |
| 2004/0186349 A1 | 9/2004 | Ewers et al. |
| 2004/0249267 A1 | 12/2004 | Gilboa |
| 2004/0263535 A1 | 12/2004 | Birkenbach et al. |
| 2005/0027397 A1 | 2/2005 | Niemeyer |
| 2005/0060006 A1 | 3/2005 | Pflueger et al. |
| 2005/0085714 A1 | 4/2005 | Foley et al. |
| 2005/0107679 A1 | 5/2005 | Geiger et al. |
| 2005/0143649 A1 | 6/2005 | Minai et al. |
| 2005/0143655 A1 | 6/2005 | Satoh |
| 2005/0182295 A1 | 8/2005 | Soper et al. |
| 2005/0193451 A1 | 9/2005 | Quistgaard et al. |
| 2005/0256398 A1 | 11/2005 | Hastings et al. |
| 2005/0272975 A1 | 12/2005 | McWeeney et al. |
| 2006/0004286 A1 | 1/2006 | Chang et al. |
| 2006/0015096 A1 | 1/2006 | Hauck et al. |
| 2006/0025668 A1 | 2/2006 | Peterson et al. |
| 2006/0058643 A1 | 3/2006 | Florent et al. |
| 2006/0084860 A1 | 4/2006 | Geiger et al. |
| 2006/0095066 A1 | 5/2006 | Chang et al. |
| 2006/0098851 A1 | 5/2006 | Shoham et al. |
| 2006/0149134 A1 | 7/2006 | Soper et al. |
| 2006/0173290 A1 | 8/2006 | Lavallee et al. |
| 2006/0184016 A1 | 8/2006 | Glossop |
| 2006/0209019 A1 | 9/2006 | Hu |
| 2006/0258935 A1 | 11/2006 | Pile-Spellman et al. |
| 2006/0258938 A1 | 11/2006 | Hoffman et al. |
| 2007/0032826 A1 | 2/2007 | Schwartz |
| 2007/0055128 A1 | 3/2007 | Glossop |
| 2007/0055144 A1 | 3/2007 | Neustadter et al. |
| 2007/0073136 A1 | 3/2007 | Metzger |
| 2007/0083193 A1 | 4/2007 | Werneth et al. |
| 2007/0123748 A1 | 5/2007 | Meglan |
| 2007/0135886 A1 | 6/2007 | Maschke |
| 2007/0156019 A1 | 7/2007 | Larkin et al. |
| 2007/0167743 A1 | 7/2007 | Honda et al. |

(56) References Cited

U.S. PATENT DOCUMENTS

| | | |
|---|---|---|
| 2007/0167801 A1 | 7/2007 | Webler et al. |
| 2007/0208252 A1 | 9/2007 | Makower |
| 2007/0253599 A1 | 11/2007 | White et al. |
| 2007/0269001 A1 | 11/2007 | Maschke |
| 2007/0293721 A1 | 12/2007 | Gilboa |
| 2007/0299353 A1 | 12/2007 | Harlev et al. |
| 2008/0071140 A1 | 3/2008 | Gattani et al. |
| 2008/0079421 A1 | 4/2008 | Jensen |
| 2008/0103389 A1 | 5/2008 | Begelman et al. |
| 2008/0118118 A1 | 5/2008 | Berger |
| 2008/0118135 A1 | 5/2008 | Averbuch et al. |
| 2008/0123921 A1 | 5/2008 | Gielen et al. |
| 2008/0147089 A1 | 6/2008 | Loh et al. |
| 2008/0161681 A1 | 7/2008 | Hauck |
| 2008/0183064 A1 | 7/2008 | Chandonnet et al. |
| 2008/0183068 A1 | 7/2008 | Carls et al. |
| 2008/0183073 A1 | 7/2008 | Higgins et al. |
| 2008/0183188 A1 | 7/2008 | Carls et al. |
| 2008/0201016 A1 | 8/2008 | Finlay |
| 2008/0207997 A1 | 8/2008 | Higgins et al. |
| 2008/0212082 A1 | 9/2008 | Froggatt et al. |
| 2008/0218770 A1 | 9/2008 | Moll et al. |
| 2008/0243142 A1 | 10/2008 | Gildenberg |
| 2008/0262297 A1 | 10/2008 | Gilboa et al. |
| 2008/0275349 A1 | 11/2008 | Halperin et al. |
| 2008/0287963 A1 | 11/2008 | Rogers et al. |
| 2008/0306490 A1 | 12/2008 | Lakin et al. |
| 2008/0312501 A1 | 12/2008 | Hasegawa et al. |
| 2009/0030307 A1 | 1/2009 | Govari et al. |
| 2009/0054729 A1 | 2/2009 | Mori et al. |
| 2009/0076476 A1 | 3/2009 | Barbagli et al. |
| 2009/0149867 A1 | 6/2009 | Glozman et al. |
| 2009/0227861 A1 | 9/2009 | Ganatra et al. |
| 2009/0248036 A1 | 10/2009 | Hoffman et al. |
| 2009/0259230 A1 | 10/2009 | Khadem et al. |
| 2009/0262109 A1 | 10/2009 | Markowitz et al. |
| 2009/0292166 A1 | 11/2009 | Ito et al. |
| 2009/0295797 A1 | 12/2009 | Sakaguchi |
| 2010/0008555 A1 | 1/2010 | Trumer et al. |
| 2010/0039506 A1 | 2/2010 | Sarvestani et al. |
| 2010/0041949 A1 | 2/2010 | Tolkowsky |
| 2010/0054536 A1 | 3/2010 | Huang et al. |
| 2010/0113852 A1 | 5/2010 | Sydora |
| 2010/0121139 A1 | 5/2010 | OuYang et al. |
| 2010/0160733 A1 | 6/2010 | Gilboa |
| 2010/0161022 A1 | 6/2010 | Tolkowsky |
| 2010/0161129 A1 | 6/2010 | Costa et al. |
| 2010/0225209 A1 | 9/2010 | Goldberg et al. |
| 2010/0240989 A1 | 9/2010 | Stoianovici et al. |
| 2010/0290530 A1 | 11/2010 | Huang et al. |
| 2010/0292565 A1 | 11/2010 | Meyer et al. |
| 2010/0298641 A1 | 11/2010 | Tanaka |
| 2010/0328455 A1 | 12/2010 | Nam et al. |
| 2011/0054303 A1 | 3/2011 | Barrick et al. |
| 2011/0092808 A1 | 4/2011 | Shachar et al. |
| 2011/0184238 A1 | 7/2011 | Higgins et al. |
| 2011/0234780 A1 | 9/2011 | Ito et al. |
| 2011/0238082 A1 | 9/2011 | Wenderow et al. |
| 2011/0245665 A1 | 10/2011 | Nentwick |
| 2011/0248987 A1 | 10/2011 | Mitchell |
| 2011/0249016 A1 | 10/2011 | Zhang et al. |
| 2011/0276179 A1 | 11/2011 | Banks et al. |
| 2011/0319910 A1 | 12/2011 | Roelle et al. |
| 2012/0046521 A1 | 2/2012 | Hunter et al. |
| 2012/0056986 A1 | 3/2012 | Popovic |
| 2012/0062714 A1 | 3/2012 | Liu et al. |
| 2012/0065481 A1 | 3/2012 | Hunter et al. |
| 2012/0069167 A1 | 3/2012 | Liu et al. |
| 2012/0071782 A1 | 3/2012 | Patil et al. |
| 2012/0082351 A1 | 4/2012 | Higgins et al. |
| 2012/0120305 A1 | 5/2012 | Takahashi |
| 2012/0165656 A1 | 6/2012 | Montag et al. |
| 2012/0191079 A1 | 7/2012 | Moll et al. |
| 2012/0209069 A1 | 8/2012 | Popovic et al. |
| 2012/0215094 A1 | 8/2012 | Rahimian et al. |
| 2012/0219185 A1 | 8/2012 | Hu et al. |
| 2012/0289777 A1 | 11/2012 | Chopra et al. |
| 2012/0289783 A1 | 11/2012 | Duindam et al. |
| 2012/0302869 A1 | 11/2012 | Koyrakh et al. |
| 2013/0060146 A1 | 3/2013 | Yang et al. |
| 2013/0144116 A1 | 6/2013 | Cooper et al. |
| 2013/0165945 A9 | 6/2013 | Roelle et al. |
| 2013/0204124 A1 | 8/2013 | Duindam et al. |
| 2013/0225942 A1 | 8/2013 | Holsing et al. |
| 2013/0243153 A1 | 9/2013 | Sra et al. |
| 2013/0246334 A1 | 9/2013 | Ahuja et al. |
| 2013/0259315 A1 | 10/2013 | Angot et al. |
| 2013/0303892 A1 | 11/2013 | Zhao et al. |
| 2013/0345718 A1 | 12/2013 | Crawford et al. |
| 2014/0058406 A1 | 2/2014 | Tsekos |
| 2014/0107390 A1 | 4/2014 | Brown et al. |
| 2014/0114180 A1 | 4/2014 | Jain |
| 2014/0142591 A1 | 5/2014 | Alvarez et al. |
| 2014/0148808 A1 | 5/2014 | Inkpen et al. |
| 2014/0180063 A1 | 6/2014 | Zhao et al. |
| 2014/0235943 A1 | 8/2014 | Paris et al. |
| 2014/0243849 A1 | 8/2014 | Saglam et al. |
| 2014/0257746 A1 | 9/2014 | Dunbar et al. |
| 2014/0264081 A1 | 9/2014 | Walker et al. |
| 2014/0275988 A1 | 9/2014 | Walker et al. |
| 2014/0276033 A1 | 9/2014 | Brannan et al. |
| 2014/0276937 A1 | 9/2014 | Wong et al. |
| 2014/0296655 A1 | 10/2014 | Akhbardeh et al. |
| 2014/0309527 A1 | 10/2014 | Namati et al. |
| 2014/0343416 A1 | 11/2014 | Panescu et al. |
| 2014/0350391 A1 | 11/2014 | Prisco et al. |
| 2014/0357984 A1 | 12/2014 | Wallace et al. |
| 2014/0364739 A1 | 12/2014 | Liu et al. |
| 2014/0364870 A1 | 12/2014 | Alvarez et al. |
| 2015/0051482 A1 | 2/2015 | Liu et al. |
| 2015/0051592 A1 | 2/2015 | Kintz |
| 2015/0054929 A1 | 2/2015 | Ito et al. |
| 2015/0057498 A1 | 2/2015 | Akimoto et al. |
| 2015/0073266 A1 | 3/2015 | Brannan et al. |
| 2015/0119637 A1 | 4/2015 | Alvarez et al. |
| 2015/0141808 A1 | 5/2015 | Elhawary et al. |
| 2015/0141858 A1 | 5/2015 | Razavi et al. |
| 2015/0142013 A1 | 5/2015 | Tanner et al. |
| 2015/0164594 A1 | 6/2015 | Romo et al. |
| 2015/0164596 A1 | 6/2015 | Romo et al. |
| 2015/0223725 A1 | 8/2015 | Engel et al. |
| 2015/0223897 A1 | 8/2015 | Kostrzewski et al. |
| 2015/0223902 A1 | 8/2015 | Walker et al. |
| 2015/0255782 A1 | 9/2015 | Kim et al. |
| 2015/0265087 A1 | 9/2015 | Messick, Jr. |
| 2015/0265368 A1 | 9/2015 | Chopra et al. |
| 2015/0275986 A1 | 10/2015 | Cooper |
| 2015/0287192 A1 | 10/2015 | Sasaki |
| 2015/0297133 A1 | 10/2015 | Jouanique-Dubuis et al. |
| 2015/0305650 A1 | 10/2015 | Hunter et al. |
| 2015/0313503 A1 | 11/2015 | Seibel et al. |
| 2015/0335480 A1 | 11/2015 | Alvarez et al. |
| 2016/0000302 A1 | 1/2016 | Brown et al. |
| 2016/0000414 A1 | 1/2016 | Brown et al. |
| 2016/0000520 A1 | 1/2016 | Lachmanovich et al. |
| 2016/0001038 A1 | 1/2016 | Romo et al. |
| 2016/0008033 A1 | 1/2016 | Hawkins et al. |
| 2016/0111192 A1 | 4/2016 | Suzara |
| 2016/0128992 A1 | 5/2016 | Hudson et al. |
| 2016/0183841 A1 | 6/2016 | Duindam et al. |
| 2016/0199134 A1 | 7/2016 | Brown et al. |
| 2016/0206389 A1 | 7/2016 | Miller |
| 2016/0213432 A1 | 7/2016 | Flexman et al. |
| 2016/0228032 A1 | 8/2016 | Walker et al. |
| 2016/0270865 A1 | 9/2016 | Landey et al. |
| 2016/0279394 A1 | 9/2016 | Moll et al. |
| 2016/0287279 A1 | 10/2016 | Bovay et al. |
| 2016/0287346 A1 | 10/2016 | Hyodo et al. |
| 2016/0314710 A1 | 10/2016 | Jarc et al. |
| 2016/0331469 A1 | 11/2016 | Hall et al. |
| 2016/0360947 A1 | 12/2016 | Iida et al. |
| 2016/0372743 A1 | 12/2016 | Cho et al. |
| 2016/0374541 A1 | 12/2016 | Agrawal et al. |
| 2017/0007337 A1 | 1/2017 | Dan |

(56) References Cited

U.S. PATENT DOCUMENTS

| | | |
|---|---|---|
| 2017/0055851 A1 | 3/2017 | Al-Ali |
| 2017/0079725 A1 | 3/2017 | Hoffman et al. |
| 2017/0079726 A1 | 3/2017 | Hoffman et al. |
| 2017/0084027 A1 | 3/2017 | Mintz et al. |
| 2017/0100199 A1 | 4/2017 | Yu et al. |
| 2017/0119412 A1 | 5/2017 | Noonan et al. |
| 2017/0119481 A1 | 5/2017 | Romo et al. |
| 2017/0165011 A1 | 6/2017 | Bovay et al. |
| 2017/0172673 A1 | 6/2017 | Yu et al. |
| 2017/0189118 A1 | 7/2017 | Chopra et al. |
| 2017/0202627 A1 | 7/2017 | Sramek et al. |
| 2017/0209073 A1 | 7/2017 | Sramek et al. |
| 2017/0215808 A1 | 8/2017 | Shimol et al. |
| 2017/0215969 A1 | 8/2017 | Zhai et al. |
| 2017/0238807 A9 | 8/2017 | Vertikov |
| 2017/0258366 A1 | 9/2017 | Tupin, Jr. et al. |
| 2017/0290631 A1 | 10/2017 | Lee et al. |
| 2017/0296032 A1 | 10/2017 | Li |
| 2017/0296202 A1 | 10/2017 | Brown |
| 2017/0303941 A1 | 10/2017 | Eisner |
| 2017/0325896 A1 | 11/2017 | Donhowe et al. |
| 2017/0333679 A1 | 11/2017 | Jiang |
| 2017/0340241 A1 | 11/2017 | Yamada |
| 2017/0340396 A1 | 11/2017 | Romo et al. |
| 2017/0348067 A1 | 12/2017 | Krimsky |
| 2017/0360508 A1 | 12/2017 | Germain et al. |
| 2017/0365055 A1 | 12/2017 | Mintz et al. |
| 2017/0367782 A1 | 12/2017 | Schuh et al. |
| 2018/0025666 A1 | 1/2018 | Ho et al. |
| 2018/0055582 A1 | 3/2018 | Krimsky |
| 2018/0098690 A1 | 4/2018 | Iwaki |
| 2018/0177556 A1 | 6/2018 | Noonan |
| 2018/0177561 A1 | 6/2018 | Mintz et al. |
| 2018/0214011 A1 | 8/2018 | Graetzel et al. |
| 2018/0217734 A1 | 8/2018 | Koenig et al. |
| 2018/0221038 A1 | 8/2018 | Noonan et al. |
| 2018/0221039 A1 | 8/2018 | Shah |
| 2018/0240237 A1 | 8/2018 | Donhowe et al. |
| 2018/0250083 A1 | 9/2018 | Schuh et al. |
| 2018/0271616 A1 | 9/2018 | Schuh et al. |
| 2018/0279852 A1 | 10/2018 | Rafii-Tari et al. |
| 2018/0280660 A1 | 10/2018 | Landey et al. |
| 2018/0286108 A1 | 10/2018 | Hirakawa |
| 2018/0289431 A1 | 10/2018 | Draper et al. |
| 2018/0308247 A1 | 10/2018 | Gupta |
| 2018/0325499 A1 | 11/2018 | Landey et al. |
| 2018/0333044 A1 | 11/2018 | Jenkins |
| 2018/0360435 A1 | 12/2018 | Romo |
| 2018/0368920 A1 | 12/2018 | Ummalaneni |
| 2019/0000559 A1 | 1/2019 | Berman et al. |
| 2019/0000560 A1 | 1/2019 | Berman et al. |
| 2019/0000566 A1 | 1/2019 | Graetzel et al. |
| 2019/0000576 A1 | 1/2019 | Mintz et al. |
| 2019/0046814 A1 | 2/2019 | Senden et al. |
| 2019/0066314 A1 | 2/2019 | Abhari et al. |
| 2019/0083183 A1 | 3/2019 | Moll et al. |
| 2019/0086349 A1 | 3/2019 | Nelson et al. |
| 2019/0105776 A1 | 4/2019 | Ho et al. |
| 2019/0105785 A1 | 4/2019 | Meyer et al. |
| 2019/0107454 A1 | 4/2019 | Lin et al. |
| 2019/0110839 A1* | 4/2019 | Rafii-Tari .............. A61B 34/20 |
| 2019/0110843 A1 | 4/2019 | Ummalaneni |
| 2019/0117176 A1 | 4/2019 | Walker et al. |
| 2019/0117203 A1 | 4/2019 | Wong et al. |
| 2019/0125164 A1 | 5/2019 | Roelle et al. |
| 2019/0151148 A1 | 5/2019 | Alvarez et al. |
| 2019/0167366 A1 | 6/2019 | Ummalaneni et al. |
| 2019/0175009 A1 | 6/2019 | Mintz et al. |
| 2019/0175062 A1 | 6/2019 | Rafii-Tari et al. |
| 2019/0175287 A1 | 6/2019 | Hill et al. |
| 2019/0175799 A1 | 6/2019 | Hsu et al. |
| 2019/0183585 A1 | 6/2019 | Rafii-Tari et al. |
| 2019/0183587 A1 | 6/2019 | Rafii-Tari et al. |
| 2019/0216548 A1 | 7/2019 | Ummalaneni |
| 2019/0216550 A1 | 7/2019 | Eyre et al. |
| 2019/0216576 A1 | 7/2019 | Eyre et al. |
| 2019/0223974 A1 | 7/2019 | Romo et al. |
| 2019/0228525 A1 | 7/2019 | Mintz et al. |
| 2019/0228528 A1 | 7/2019 | Mintz et al. |
| 2019/0246882 A1 | 8/2019 | Graetzel et al. |
| 2019/0262086 A1 | 8/2019 | Connolly et al. |
| 2019/0269468 A1 | 9/2019 | Hsu et al. |
| 2019/0274764 A1 | 9/2019 | Romo |
| 2019/0287673 A1 | 9/2019 | Michihata et al. |
| 2019/0290109 A1 | 9/2019 | Agrawal et al. |
| 2019/0298160 A1 | 10/2019 | Ummalaneni et al. |
| 2019/0298458 A1 | 10/2019 | Srinivasan et al. |
| 2019/0298460 A1 | 10/2019 | Al-Jadda et al. |
| 2019/0298465 A1 | 10/2019 | Chin et al. |
| 2019/0328213 A1 | 10/2019 | Landey et al. |
| 2019/0336238 A1 | 11/2019 | Yu et al. |
| 2019/0365209 A1 | 12/2019 | Ye et al. |
| 2019/0365479 A1 | 12/2019 | Rafii-Tari |
| 2019/0365486 A1* | 12/2019 | Srinivasan ............. A61B 34/30 |
| 2019/0374297 A1 | 12/2019 | Wallace et al. |
| 2019/0375383 A1 | 12/2019 | Auer |
| 2019/0380787 A1 | 12/2019 | Ye et al. |
| 2019/0380797 A1 | 12/2019 | Yu et al. |
| 2020/0000530 A1 | 1/2020 | DeFonzo et al. |
| 2020/0000533 A1 | 1/2020 | Schuh et al. |
| 2020/0022767 A1 | 1/2020 | Hill et al. |
| 2020/0039086 A1 | 2/2020 | Meyer et al. |
| 2020/0046434 A1 | 2/2020 | Graetzel et al. |
| 2020/0054408 A1 | 2/2020 | Schuh et al. |
| 2020/0060516 A1 | 2/2020 | Baez, Jr. |
| 2020/0078103 A1 | 3/2020 | Duindam et al. |
| 2020/0093549 A1 | 3/2020 | Chin et al. |
| 2020/0093554 A1 | 3/2020 | Schuh et al. |
| 2020/0100845 A1 | 4/2020 | Julian |
| 2020/0101264 A1 | 4/2020 | Jiang |
| 2020/0107894 A1 | 4/2020 | Wallace et al. |
| 2020/0121502 A1 | 4/2020 | Kintz |
| 2020/0146769 A1 | 5/2020 | Eyre et al. |
| 2020/0155084 A1 | 5/2020 | Walker et al. |
| 2020/0170630 A1 | 6/2020 | Wong et al. |
| 2020/0170720 A1 | 6/2020 | Ummalaneni |
| 2020/0188043 A1 | 6/2020 | Yu et al. |
| 2020/0197112 A1 | 6/2020 | Chin et al. |
| 2020/0206472 A1 | 7/2020 | Ma et al. |
| 2020/0217733 A1 | 7/2020 | Lin et al. |
| 2020/0222134 A1 | 7/2020 | Schuh et al. |
| 2020/0237458 A1 | 7/2020 | DeFonzo et al. |
| 2020/0261172 A1 | 8/2020 | Romo et al. |
| 2020/0268459 A1 | 8/2020 | Noonan |
| 2020/0268460 A1 | 8/2020 | Tse et al. |
| 2021/0282862 A1* | 9/2021 | Bourlion ................ A61B 34/10 |

FOREIGN PATENT DOCUMENTS

| | | |
|---|---|---|
| CN | 102316817 A | 1/2012 |
| CN | 102458295 A | 5/2012 |
| CN | 102973317 A | 3/2013 |
| CN | 103735313 A | 4/2014 |
| CN | 105511881 A | 4/2016 |
| CN | 105559850 A | 5/2016 |
| CN | 105559886 A | 5/2016 |
| CN | 106821498 A | 6/2017 |
| CN | 104931059 B | 9/2018 |
| EP | 3025630 A1 | 6/2016 |
| JP | 2015519130 A | 7/2015 |
| JP | 2016523592 A | 8/2016 |
| JP | 2016533836 A | 11/2016 |
| JP | 2017525418 A | 9/2017 |
| KR | 20140009359 A | 1/2014 |
| RU | 2569699 C2 | 11/2015 |
| WO | 2005087128 A1 | 9/2005 |
| WO | 2009097461 A1 | 8/2009 |
| WO | 2013173227 A1 | 11/2013 |
| WO | 2014186715 A1 | 11/2014 |
| WO | 2015031999 A1 | 3/2015 |
| WO | 2015089013 A1 | 6/2015 |
| WO | 2016004007 A1 | 1/2016 |
| WO | 2016164311 A1 | 10/2016 |
| WO | 2017048194 A1 | 3/2017 |

(56) References Cited

FOREIGN PATENT DOCUMENTS

| | | |
|---|---|---|
| WO | 2017049163 A1 | 3/2017 |
| WO | 2017066108 A1 | 4/2017 |
| WO | 2017167754 A1 | 10/2017 |

OTHER PUBLICATIONS

Al-Ahmad et al., dated 2005, Eady experience with a computerized robotically controlled catheter system, Journal of Interventional Cardiac Electrophysiology, 12:199-202, 4 pages.

Ciuti et al, 2012, Intra-operative monocular 3D reconstruction for image-guided navigation in active locomotion capsule endoscopy. Biomedical Robotics And Biomechatronics (Biorob), 4th IEEE Ras & Embs International Conference On IEEE, 7 pages.

CN 1st Office Action for appl No. 201980003361.2, 12 pages.

Fallavoliita et al., 2010, Acquiring multiview C-arm images to assist cardiac ablation procedures, EURASIP Journal on Image and Video Processing, vol. 2010, Article ID 871408, pp. 1-10.

Final Rejection for U.S. Appl. No. 16/424,188, dated Apr. 13, 2020, 8 pages.

Gutierrez et al., Mar. 2008, A practical global distortion correction method for an image intensifier based x-ray fluoroscopy system, Med. Phys, 35(3):997-1007, 11 pages.

Haigron et al., 2004, Depth-map-based scene analysis for active navigation in virtual angioscopy, IEEE Transactions on Medical Imaging, 23( 11 ): 1380-1390, 11 pages.

Hansen Medical, Inc. 2005, System Overview, product brochure, 2 pp., dated as available at http://hansenmedical.com/system.aspx on Jul. 14, 2006 (accessed Jun. 25, 2019 using the internet archive way back machine).

Hansen Medical, Inc. Bibliography, product brochure, 1 p., dated as available athttp://hansenmedical.com/bibliography.aspx on Jul. 14, 2006 (accessed Jun. 25, 2019 using the internet archive way back machine).

Hansen Medical, Inc. dated 2007, Introducing the Sensei Robotic Catheter System, product brochure, 10 pages.

Hansen Medical, Inc. dated 2009, Sensei X Robotic Catheter System, product brochure, 3 pp.

Hansen Medical, Inc. Technology Advantages, product brochure, 1 p., dated as available at http://hansenmedical.com/advantages.aspx on Jul. 13, 2006 (accessed Jun. 25, 2019 using the internet archive way back machine).

International search report and written opinion dated Sep. 23, 2019 for PCT/US2019/034137, 10 pages.

Kiraly et al, 2002, Three-dimensional Human Airway Segmentation Methods for Clinical Virtual Bronchoscopy, Acad Radio!, 9:1153-1168, 16 pages.

Kiraly et al., Sep. 2004, Three-dimensional path planning for virtual bronchoscopy, IEEE Transactions on Medical Imaging, 23(9):1365-1379, 15 pages.

Konen et al., 1998, The VN-project endoscopic image processing for neurosurgery, Computer Aided Surgery, 3:1-6 , 6 pages.

Kumar et al., 2014, Stereoscopic visualization of laparoscope image using depth information from 3D model, Computer methods and programs in biomedicine 113(3):862-868, 7 pages.

Livatino et al., 2015, Stereoscopic visualization and 3-D technologies in medical endoscopic teleoperation, IEEE, 11 pages.

Luo et al., 2010, Modified hybrid bronchoscope tracking based on sequential monte carlo sampler: Dynamic phantom validation, Asian Conference on Computer Vision. Springer, Berlin, Heidelberg, 13 pages.

Marrouche et al., dated May 6, 2005, AB32-1, Preliminary human experience using a novel robotic catheter remote control, Heart Rhythm, 2(5):S63, 1 page.

Mayo Clinic, Robotic Surgery, https://www.mayoclinic.org/tests-procedures/robotic-surgery/about/pac- 20394974?p=1, downloaded from the internet on Jul. 12, 2018, 2 pgs.

Mourgues et al., 2002, Flexible calibration of actuated stereoscopic endoscope for overlay in robot 672 assisted surgery, International Conference on Medical Image Computing and Computer-Assisted Intervention. SprinQer, Berlin, HeidelberQ, 10 pages.

Nadeem et al., 2016, Depth Reconstruction and Computer-Aided Polyp Detection in Optical Colonoscopy Video Frames, arXiv preprint arXiv:1609.01329.

Non-Final Rejection for U.S. Appl. No. 16/424,188, dated Oct. 30, 2019, 12 pages.

Notice of Allowance for U.S. Appl. No. 16/424,188, dated Jun. 22, 2020, 9 pages.

Notice of Allowance for U.S. Appl. No. 16/424,188, dated Oct. 19, 2020, 9 pages.

Oh et al., dated May 2005, p. 5-75, Novel robotic catheter remote control system: safety and accuracy in delivering RF Lesions in all 4 cardiac chambers, Heart Rhythm, 2(5):S277-S278.

Point Cloud, Sep. 10, 2010, Wikipedia, 2 pp.

Racadio et al., Dec. 2007, Live 3D guidance in the interventionail radiology suite, AJR, 189:W357-W364, 8 pages.

Reddy et al., May 2005, p. 1-53. Porcine pulmonary vein ablation using a novel robotic catheter control system and real-time integration of CT imaging with electroanatomical mapping, Hearth Rhythm, 2(5):S121, 1 page.

Sato et al., 2016, Techniques of stapler-based navigational thoracoscopic segmentectomy using virtual assisted lung mapping (VAL-MAP), Journal ofThoracic Disease, 8(Suppl 9):S716.

Shen et al., 2015, Robust camera localisation with depth reconstruction for bronchoscopic navigation. International Journal of Computer Assisted Radiology and Surgery, 10(6):801-813, 13 pages.

Shi et al., Sep. 14-18, 2014, Simultaneous catheter and environment modeling for trans-catheter aortic valve implantation, IEEE/RSJ International Conference on Intelligent Robots and Systems, pp. 2024-2202.

Slepian, dated 2010, Robotic Catheter Intervention: the Hansen Medical Sensei Robot Catheter System, PowerPoint presentation, 28 pages.

Soiheim et ai., May 14, 2009, Navigated resection of giant intracranial meningiomas based on intraoperative 30 ultrasound, Acta Neurochir, 151:1143-1151.

Solomon et al., Dec. 2000, Three-dimensional CT-Guided Bronchoscopy With a Real-Time Electromagnetic Position Sensor A Comparison of Two Image Registration Methods, Chest, 118(6):1783-1787.

Song et al., 2012, Autonomous and stable tracking of endoscope instrument tools with monocular camera, Advanced Intelligent Mechatronics (AIM), 2012 IEEE-ASME International Conference on IEEE, 6 pages.

Vemuri, A. et al.: "Inter-Operative Biopsy Site Relocalization in Endoluminal Surgery", IEEE Transactions on Biomedical Engineering, vol. 63, No. 9, Dec. 2015 (Dec. 2015), pp. 1862-1873, XP011620573, 12 pages.

Verdaasdonk et al., Jan. 23, 2012, Effect of microsecond pulse length and tip shape on explosive bubble formation of 2.78 µm Er,Cr;YSGG and 2.94 µm Er:YAG laser, Proceedings of SPIE, vol. 8221, 12, 1 pages.

Wilson et al., 2008, a buyer's guide to electromagnetic tracking systems for clinical applications, Proc. of SPCI, 6918:691828-1 p. 69188-11.

Yip et al., 2012, Tissue tracking and registration for image-guided surgery, IEEE transactions on medical imaging 31(11 ):2169-2182, 14 pages.

Zhou et al., 2010, Synthesis of stereoscopic views from monocular endoscopic videos, Compute Vision and Pattern Recognition Workshops (CVPRW), 2010 IEEE Computer Society Conference on IEE, 8 pages.

JP Office Action for Appl. No. 2020-566560, dated May 16, 2023, 3 pages.

\* cited by examiner

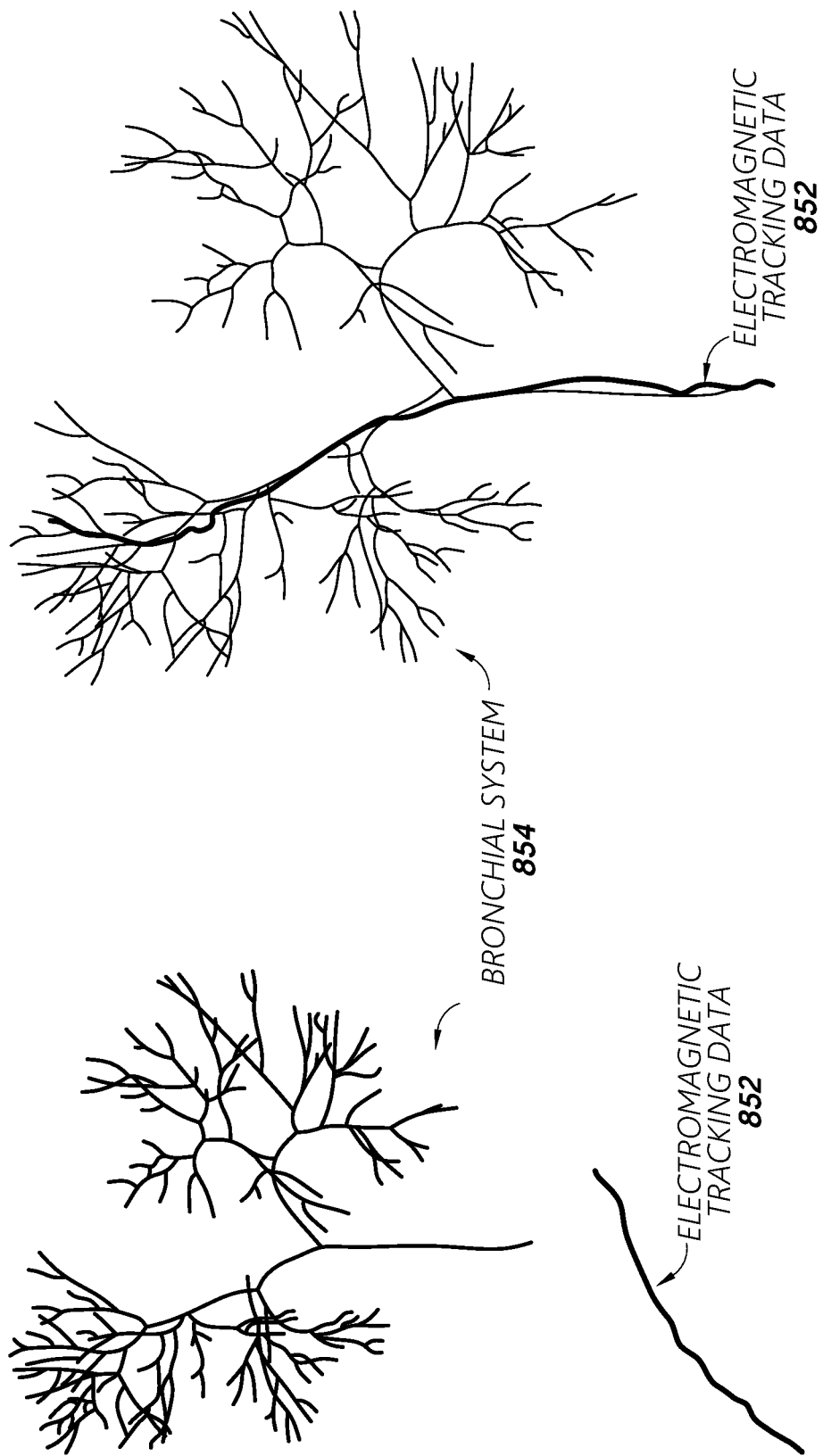

PATH-BASED NAVIGATION OF TUBULAR NETWORKS

CROSS-REFERENCE TO RELATED APPLICATIONS

This application is a continuation of U.S. patent application Ser. No. 16/424,188, now U.S. Pat. No. 10,898,286, filed May 28, 2019, which claims the benefit of U.S. Provisional Application No. 62/678,970, filed May 31, 2018, each of which is hereby incorporated by reference in its entirety.

TECHNICAL FIELD

The systems and methods disclosed herein are directed to surgical robotics, and more particularly to navigation of a medical instrument within a tubular network of a patient's body based at least in part on a path.

BACKGROUND

Bronchoscopy is a medical procedure that allows a physician to examine the inside conditions of a patient's lung airways, such as bronchi and bronchioles. The lung airways carry air from the trachea, or windpipe, to the lungs. During the medical procedure, a thin, flexible tubular tool, known as a bronchoscope, may be inserted into the patient's mouth and passed down the patient's throat into his/her lung airways, and patients are generally anesthetized in order to relax their throats and lung cavities for surgical examinations and operations during the medical procedure.

In the related art, a bronchoscope can include a light source and a small camera that allows a physician to inspect a patient's windpipe and airways, and a rigid tube may be used in conjunction with the bronchoscope for surgical purposes, e.g., when there is a significant amount of bleeding in the lungs of the patient or when a large object obstructs the throat of the patient. When the rigid tube is used, the patient is often anesthetized. Coincident with the rise of other advanced medical devices, the use of robotic bronchoscopes are increasingly becoming a reality. Robotic bronchoscopes provide tremendous advantages in navigation through tubular networks. They are easy to use and allow therapy and biopsies to be administered conveniently even during the bronchoscopy stage.

Apart from mechanical devices or platforms, e.g., robotic bronchoscopes described above, various methods and software models may be used to help with the surgical operations. As an example, a computerized tomography (CT) scan of the patient's lungs is often performed during pre-operation of a surgical examination. Data from the CT scan may be used to generate a three dimensional (3D) model of airways of the patient's lungs, and the generated 3D model enables a physician to access a visual reference that may be useful during the operative procedure of the surgical examination.

However, previous techniques for navigation of tubular networks still have challenges, even when employing medical devices (e.g., robotic bronchoscopes) and when using existing methods (e.g., performing CT scans and generating 3D models). As one example, motion estimation of a medical device (e.g., a bronchoscope tool) inside a patient's body may not be accurate based on location and orientation change of the device, and as a result the device's position may not be accurately or correctly localized inside the patient's body in real time. Inaccurate location information for such an instrument may provide misleading information to the physician that uses the 3D model as a visual reference during medical operation procedures.

Thus, there is a need for improved techniques for navigating through a network of tubular structures.

SUMMARY

The systems, methods and devices of this disclosure each have several innovative aspects, no single one of which is solely responsible for the desirable attributes disclosed herein.

In one aspect, there is provided a medical robotic system, comprising a set of one or more processors; and at least one computer-readable memory in communication with the set of processors and having stored thereon a model of a luminal network of a patient, a position of a target with respect to the model, and a path along at least a portion of the model from an access point to the target, the memory further having stored thereon computer-executable instructions to cause the set of processors to: receive location data from at least one of a set of location sensors and a set of robot command inputs, the location data being indicative of a location of an instrument configured to be driven through the luminal network, determine a first estimate of the location of the instrument at a first time based on the location data, determine a second estimate of the location of the instrument at the first time based on the path, and determine the location of the instrument at the first time based on the first estimate and the second estimate.

In another aspect, there is provided a non-transitory computer readable storage medium having stored thereon instructions that, when executed, cause at least one computing device to: receive location data from at least one of a set of location sensors and a set of robot command inputs, the location data being indicative of a location of an instrument configured to be driven through a luminal network of a patient; determine a first estimate of the location of the instrument at a first time based on the location data; determine a second estimate of the location of the instrument at the first time based on a path stored on at least one computer-readable memory, the non-transitory computer readable storage medium further having stored thereon a model of the luminal network, a position of a target with respect to the model, and the path, the path defined along at least a portion of the model from an access point to the target, and determine the location of the instrument at the first time based on the first estimate and the second estimate.

In yet another aspect, there is provided a method of estimating a location of an instrument, comprising: receiving location data from at least one of a set of location sensors and a set of robot command inputs, the location data being indicative of a location of an instrument configured to be driven through a luminal network of a patient; determining a first estimate of the location of the instrument at a first time based on the location data; determining a second estimate of the location of the instrument at the first time based on a path stored on at least one computer-readable memory, at least one computer-readable memory having stored thereon a model of the luminal network, a position of a target with respect to the model, and the path, the path defined along at least a portion of the model from an access point to the target, and determining the location of the instrument at the first time based on the first estimate and the second estimate.

In still yet another aspect, there is provided a medical robotic system, comprising a set of one or more processors; and at least one computer-readable memory in communication with the set of processors and having stored thereon a model of a mapped portion of a luminal network of a patient, a position of a target with respect to the model, and a path along at least a portion of the model from an access point to the target, the memory further having stored thereon computer-executable instructions to cause the set of processors to: determine that the path leaves the mapped portion of the luminal network before reaching the target, display a current location of an instrument via at least a first modality, the first modality derives a location based on location data received from a set of one or more location sensors and the mapped portion of the model, the instrument is configured to be driven through the luminal network, determine, based on the current location, that the distal end of the instrument is within a threshold range of a point at which the path leaves the mapped portion of the luminal network, and in response to determining that that the distal end of the instrument is within the threshold range of the point, update the current location of the instrument based on a reduction of a weight given to the first modality.

In yet another aspect, there is provided non-transitory computer readable storage medium having stored thereon instructions that, when executed, cause at least one computing device to: determine that a path leaves a mapped portion of a luminal network of a patient before reaching a target, at least one computer-readable memory having stored thereon a model of the mapped portion of the luminal network, a position of the target with respect to the model, and the path along at least a portion of the model from an access point to the target; display a current location of an instrument via at least a first modality, the first modality derives a location based on location data received from a set of one or more location sensors and the mapped portion of the model, the instrument is configured to be driven through the luminal network; determine, based on the current location, that the distal end of the instrument is within a threshold range of a point at which the path leaves the mapped portion of the luminal network; and in response to determining that that the distal end of the instrument is within the threshold range of the point, update the current location of the instrument based on a reduction of a weight given to the first modality.

In another aspect, there is provided a method of determining a location of an instrument, comprising: determining that a path leaves a mapped portion of a luminal network of a patient before reaching a target, at least one computer-readable memory having stored thereon a model of the mapped portion of the luminal network, a position of the target with respect to the model, and the path along at least a portion of the model from an access point to the target; displaying a current location of an instrument via at least a first modality, the first modality derives a location based on location data received from a set of one or more location sensors and the mapped portion of the model, the instrument is configured to be driven through the luminal network; determining, based on the current location, that the distal end of the instrument is within a threshold range of a point at which the path leaves the mapped portion of the luminal network; and in response to determining that that the distal end of the instrument is within the threshold range of the point, updating the current location of the instrument based on a reduction of a weight given to the first modality.

BRIEF DESCRIPTION OF THE DRAWINGS

The disclosed aspects will hereinafter be described in conjunction with the appended drawings, provided to illustrate and not to limit the disclosed aspects, wherein like designations denote like elements.

FIGS. 8E-8F show effect of an example registration of the EM system to a 3D model of a branched tubular network, according to one embodiment.

Reference will now be made in detail to several embodiments, examples of which are illustrated in the accompanying figures. It is noted that wherever practicable similar or like reference numbers may be used in the figures and may indicate similar or like functionality. The figures depict embodiments of the described system (or method) for purposes of illustration only. One skilled in the art will readily recognize from the following description that alternative embodiments of the structures and methods illustrated herein may be employed without departing from the principles described herein.

DETAILED DESCRIPTION

I. Surgical Robotic System

Figure 1A:
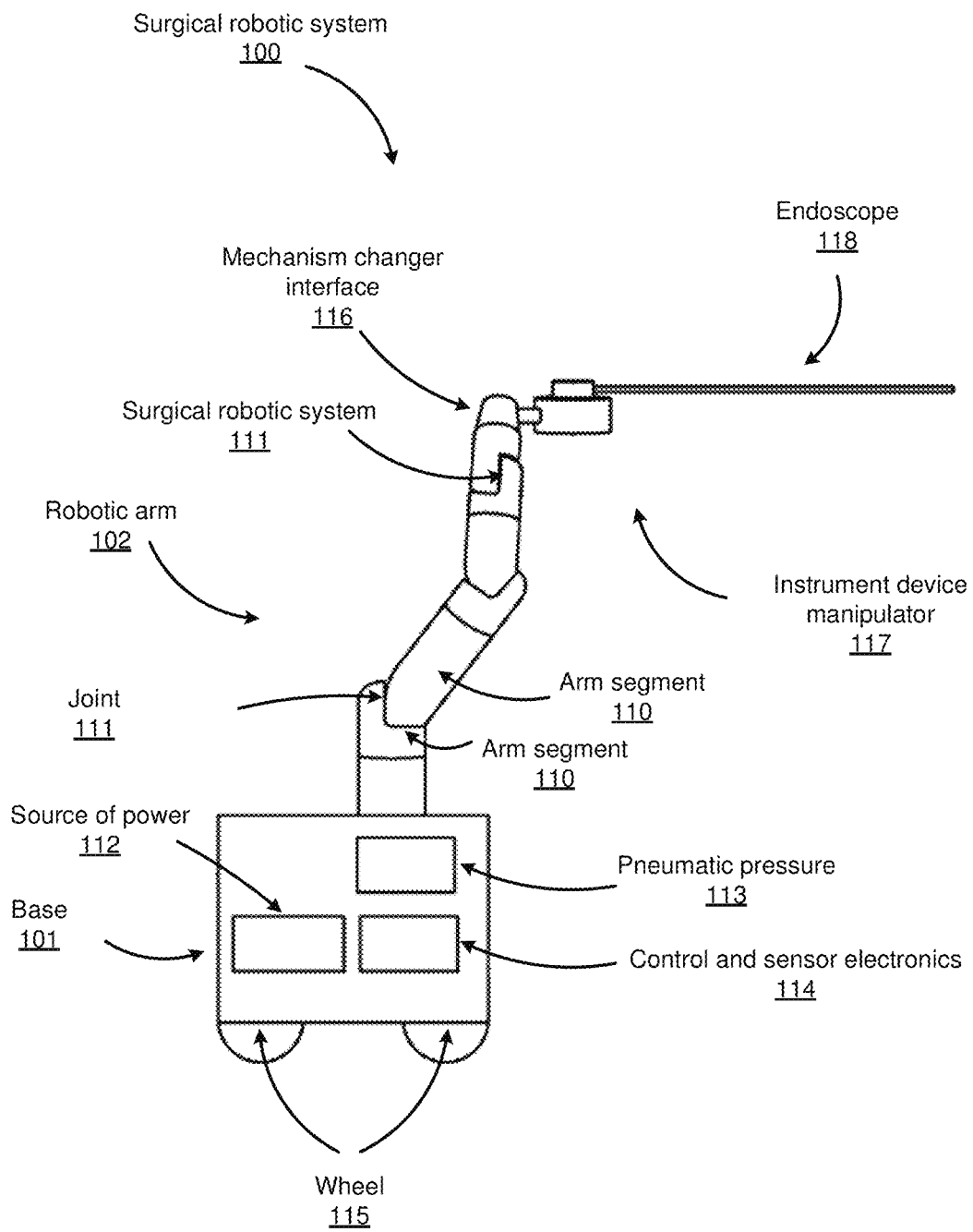
FIG. 1A shows an example surgical robotic system, according to one embodiment.

FIG. 1A shows an example surgical robotic system 100, according to one embodiment. The surgical robotic system 100 includes a base 101 coupled to one or more robotic arms, e.g., robotic arm 102. The base 101 is communicatively coupled to a command console, which is further described with reference to FIG. 2 in Section II. Command Console. The base 101 can be positioned such that the robotic arm 102 has access to perform a surgical procedure on a patient, while a user such as a physician may control the surgical robotic system 100 from the comfort of the command console. In some embodiments, the base 101 may be coupled to a surgical operating table or bed for supporting the patient. Though not shown in FIG. 1 for purposes of clarity, the base 101 may include subsystems such as control electronics, pneumatics, power sources, optical sources, and the like. The robotic arm 102 includes multiple arm segments 110 coupled at joints 111, which provides the robotic arm 102 multiple degrees of freedom, e.g., seven degrees of freedom corresponding to seven arm segments. The base 101 may contain a source of power 112, pneumatic pressure 113, and control and sensor electronics 114—including components such as a central processing unit, data bus, control circuitry, and memory—and related actuators such as motors to move the robotic arm 102. The electronics 114 in the base 101 may also process and transmit control signals communicated from the command console.

In some embodiments, the base 101 includes wheels 115 to transport the surgical robotic system 100. Mobility of the surgical robotic system 100 helps accommodate space constraints in a surgical operating room as well as facilitate appropriate positioning and movement of surgical equipment. Further, the mobility allows the robotic arms 102 to be configured such that the robotic arms 102 do not interfere with the patient, physician, anesthesiologist, or any other equipment. During procedures, a user may control the robotic arms 102 using control devices such as the command console.

In some embodiments, the robotic arm 102 includes set up joints that use a combination of brakes and counter-balances to maintain a position of the robotic arm 102. The counter-balances may include gas springs or coil springs. The brakes, e.g., fail safe brakes, may be include mechanical and/or electrical components. Further, the robotic arms 102 may be gravity-assisted passive support type robotic arms.

Each robotic arm 102 may be coupled to an instrument device manipulator (IDM) 117 using a mechanism changer interface (MCI) 116. The IDM 117 can be removed and replaced with a different type of IDM, for example, a first type of IDM manipulates an endoscope, while a second type of IDM manipulates a laparoscope. The MCI 116 includes connectors to transfer pneumatic pressure, electrical power, electrical signals, and optical signals from the robotic arm 102 to the IDM 117. The MCI 116 can be a set screw or base plate connector. The IDM 117 manipulates surgical instruments such as the endoscope 118 using techniques including direct drive, harmonic drive, geared drives, belts and pulleys, magnetic drives, and the like. The MCI 116 is interchangeable based on the type of IDM 117 and can be customized for a certain type of surgical procedure. The robotic 102 arm can include a joint level torque sensing and a wrist at a distal end, such as the KUKA AG® LBR5 robotic arm.

The endoscope 118 is a tubular and flexible surgical instrument that is inserted into the anatomy of a patient to capture images of the anatomy (e.g., body tissue). In particular, the endoscope 118 includes one or more imaging devices (e.g., cameras or other types of optical sensors) that capture the images. The imaging devices may include one or more optical components such as an optical fiber, fiber array, or lens. The optical components move along with the tip of the endoscope 118 such that movement of the tip of the endoscope 118 results in changes to the images captured by the imaging devices. The endoscope 118 is further described with reference to FIGS. 3A-4B in Section IV. Endoscope.

Robotic arms 102 of the surgical robotic system 100 manipulate the endoscope 118 using elongate movement members. The elongate movement members may include pull wires, also referred to as pull or push wires, cables, fibers, or flexible shafts. For example, the robotic arms 102 actuate multiple pull wires coupled to the endoscope 118 to deflect the tip of the endoscope 118. The pull wires may include both metallic and non-metallic materials such as stainless steel, Kevlar, tungsten, carbon fiber, and the like. The endoscope 118 may exhibit nonlinear behavior in response to forces applied by the elongate movement members. The nonlinear behavior may be based on stiffness and compressibility of the endoscope 118, as well as variability in slack or stiffness between different elongate movement members.

Figure 1B:
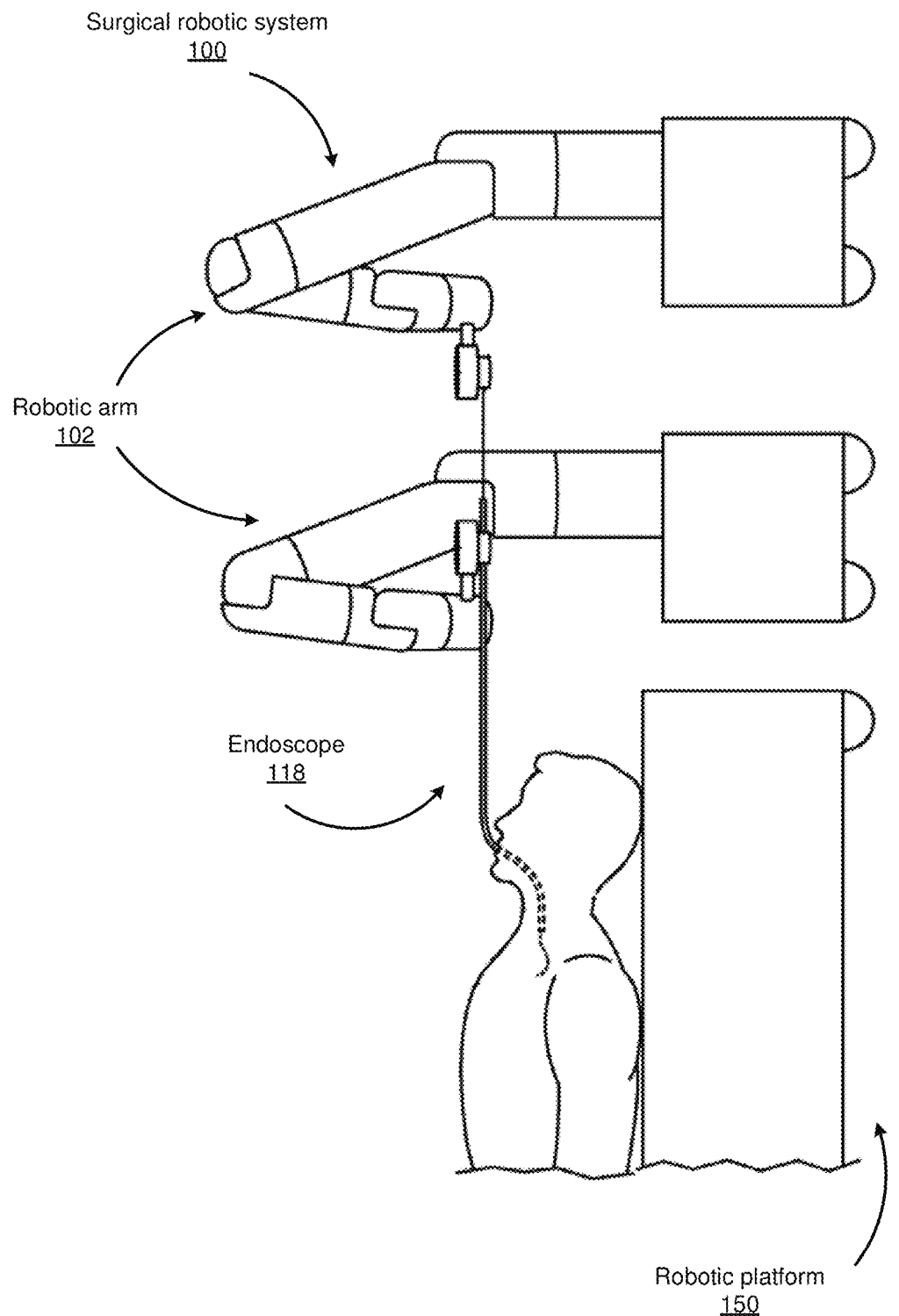
FIGS. 1B-1F show various perspective views of a robotic platform coupled to the surgical robotic system shown in FIG. 1A, according to one embodiment.
Figure 1C:
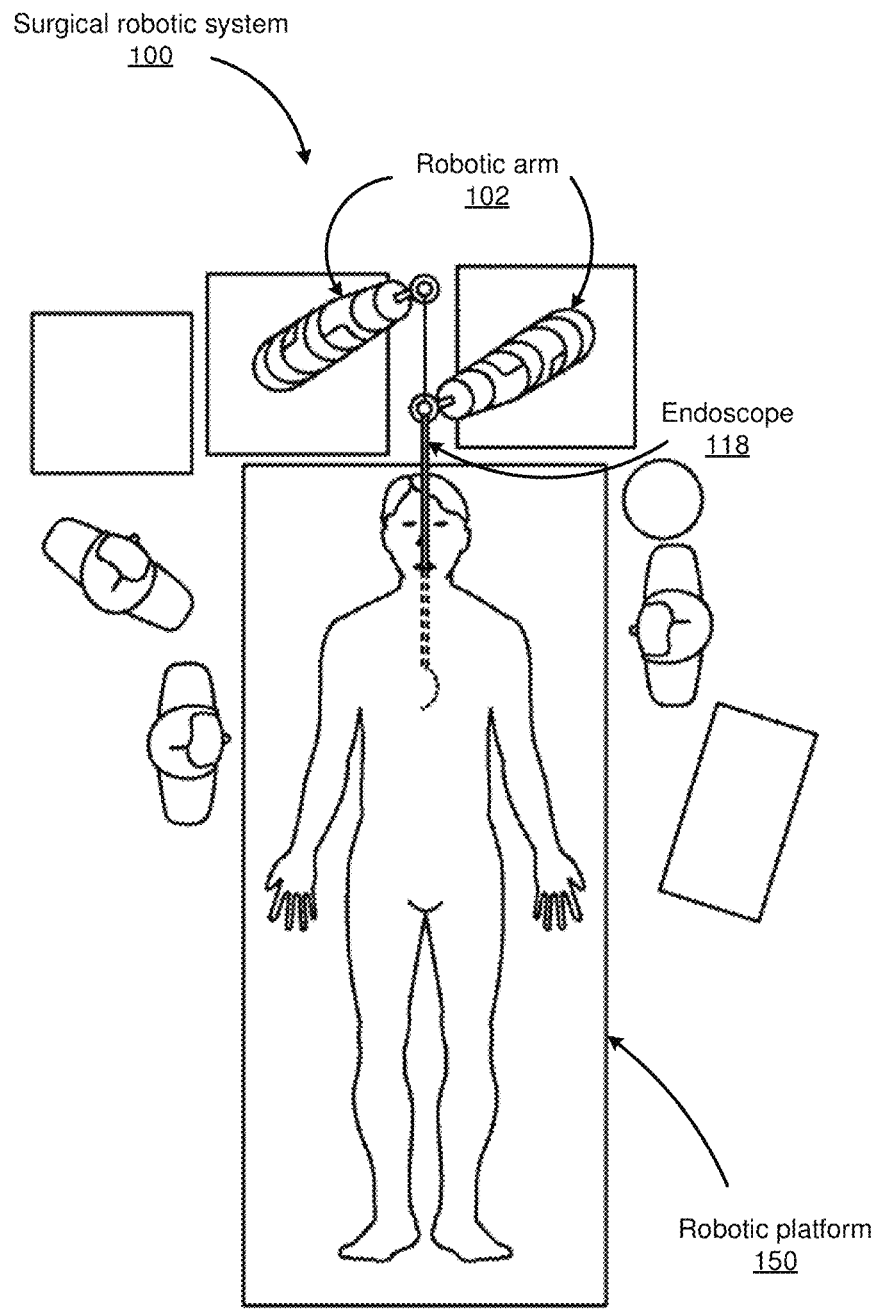
Figure 1D:
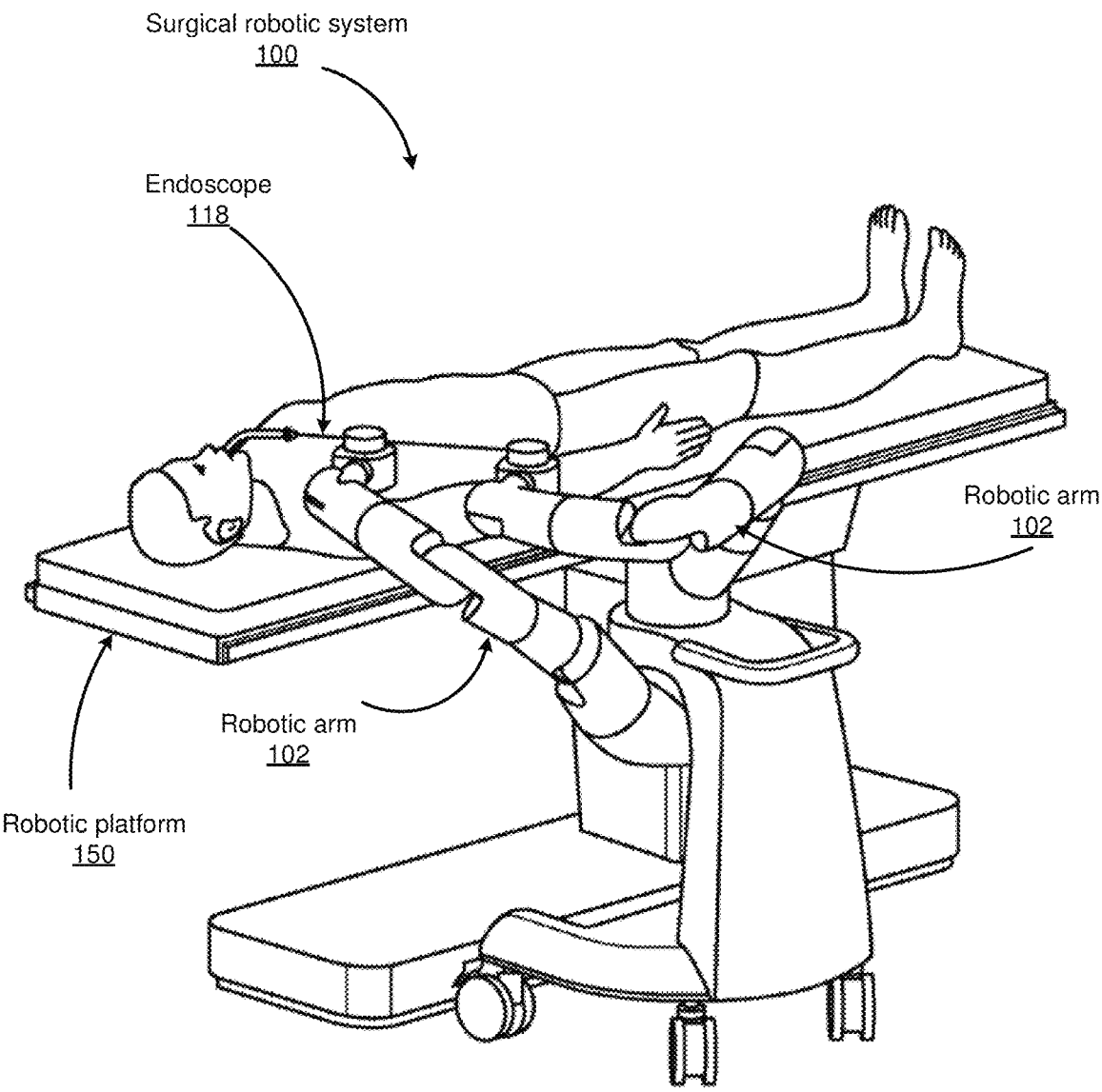
Figure 1E:
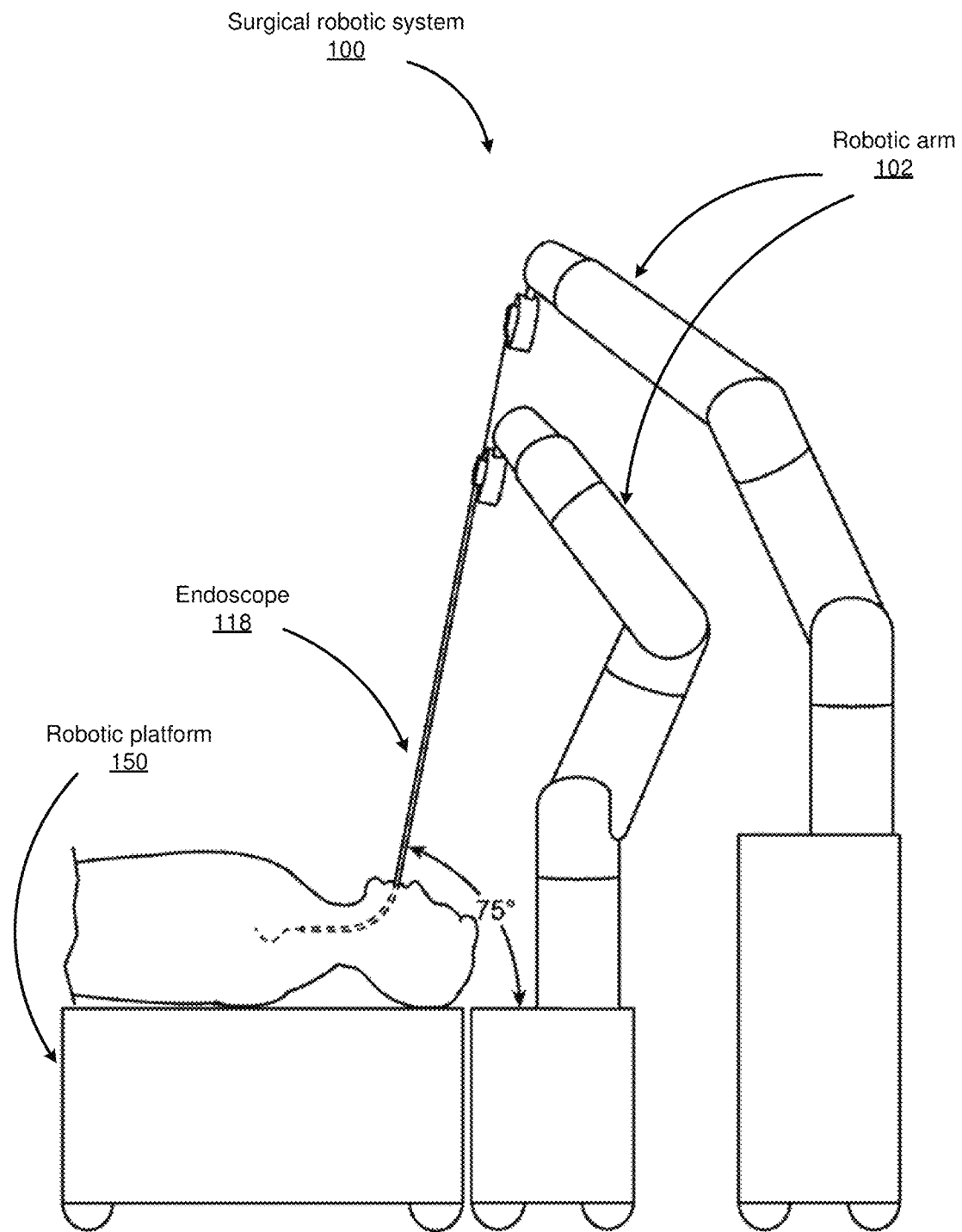
Figure 1F:
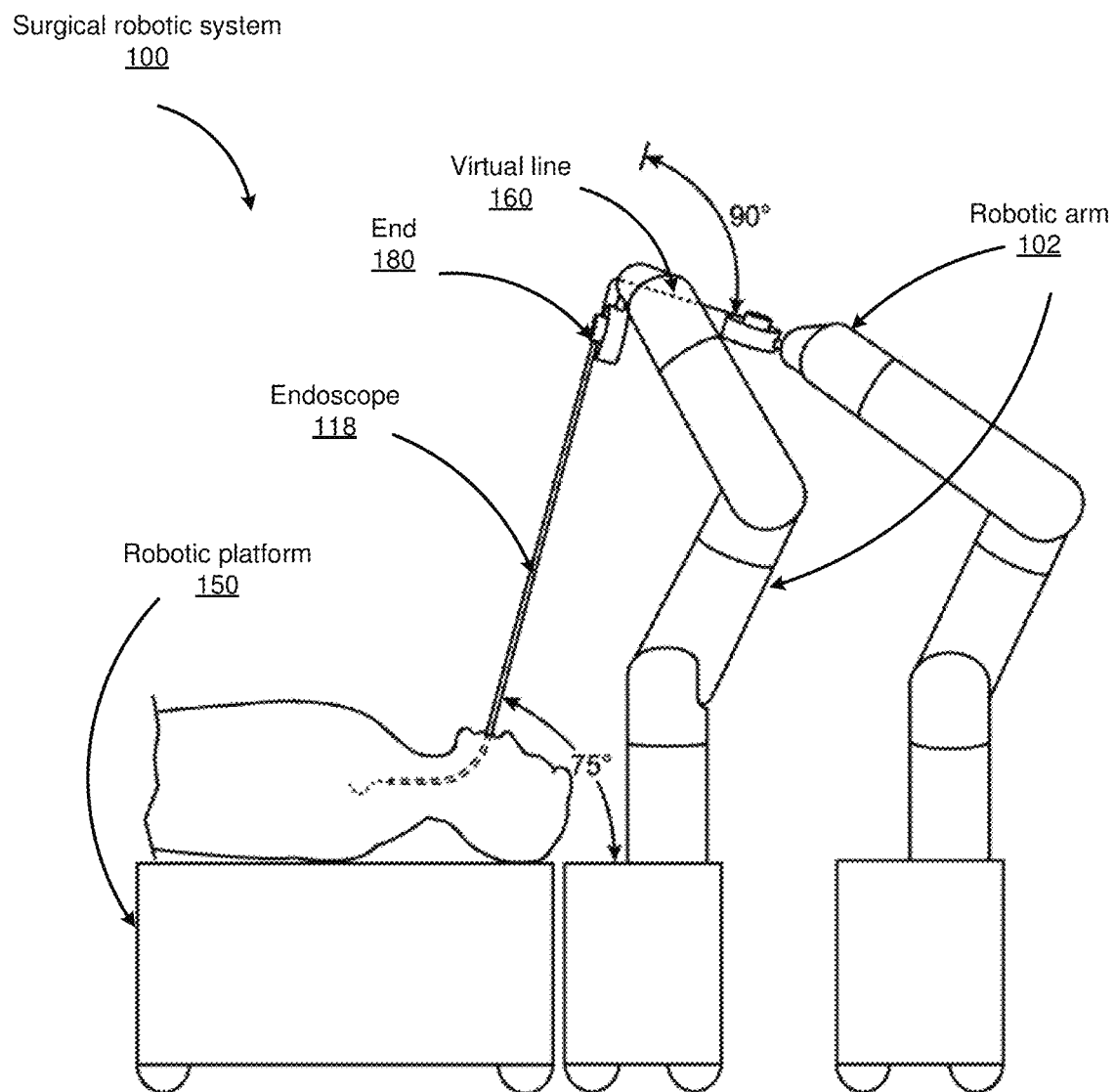

FIGS. 1B-1F show various perspective views of the surgical robotic system 100 coupled to a robotic platform 150 (or surgical bed), according to various embodiments. Specifically, FIG. 1B shows a side view of the surgical robotic system 100 with the robotic arms 102 manipulating the endoscopic 118 to insert the endoscopic inside a patient's body, and the patient is lying on the robotic platform 150. FIG. 1C shows a top view of the surgical robotic system 100 and the robotic platform 150, and the endoscopic 118 manipulated by the robotic arms is inserted inside the patient's body. FIG. 1D shows a perspective view of the surgical robotic system 100 and the robotic platform 150, and the endoscopic 118 is controlled to be positioned horizontally parallel with the robotic platform. FIG. 1E shows another perspective view of the surgical robotic system 100 and the robotic platform 150, and the endoscopic 118 is controlled to be positioned relatively perpendicular to the robotic platform. In more detail, in FIG. 1E, the angle between the horizontal surface of the robotic platform 150 and the endoscopic 118 is 75 degree. FIG. 1F shows the perspective view of the surgical robotic system 100 and the robotic platform 150 shown in FIG. 1E, and in more detail, the angle between the endoscopic 118 and the virtual line 160 connecting one end 180 of the endoscopic and the robotic arm 102 that is positioned relatively farther away from the robotic platform is 90 degree.

II. Command Console

Figure 2:
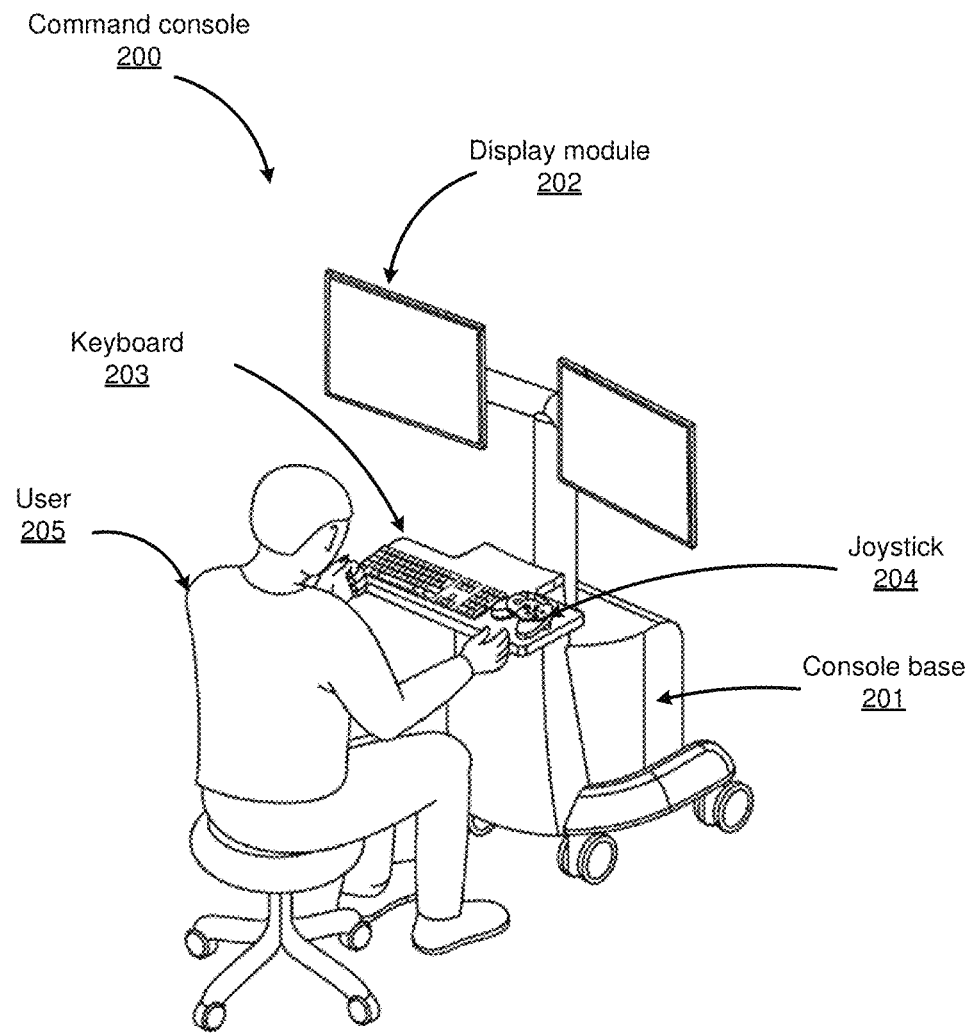
FIG. 2 shows an example command console for the example surgical robotic system, according to one embodiment.

FIG. 2 shows an example command console 200 for the example surgical robotic system 100, according to one embodiment. The command console 200 includes a console base 201, display modules 202, e.g., monitors, and control modules, e.g., a keyboard 203 and joystick 204. In some embodiments, one or more of the command console 200 functionality may be integrated into a base 101 of the surgical robotic system 100 or another system communicatively coupled to the surgical robotic system 100. A user 205, e.g., a physician, remotely controls the surgical robotic system 100 from an ergonomic position using the command console 200.

The console base 201 may include a central processing unit, a memory unit, a data bus, and associated data communication ports that are responsible for interpreting and processing signals such as camera imagery and tracking sensor data, e.g., from the endoscope 118 shown in FIG. 1. In some embodiments, both the console base 201 and the base 101 perform signal processing for load-balancing. The console base 201 may also process commands and instructions provided by the user 205 through the control modules 203 and 204. In addition to the keyboard 203 and joystick 204 shown in FIG. 2, the control modules may include other devices, for example, computer mice, trackpads, trackballs, control pads, video game controllers, and sensors (e.g., motion sensors or cameras) that capture hand gestures and finger gestures.

The user 205 can control a surgical instrument such as the endoscope 118 using the command console 200 in a velocity mode or position control mode. In velocity mode, the user 205 directly controls pitch and yaw motion of a distal end of the endoscope 118 based on direct manual control using the control modules. For example, movement on the joystick 204 may be mapped to yaw and pitch movement in the distal end of the endoscope 118. The joystick 204 can provide haptic feedback to the user 205. For example, the joystick 204 vibrates to indicate that the endoscope 118 cannot further translate or rotate in a certain direction. The command console 200 can also provide visual feedback (e.g., pop-up messages) and/or audio feedback (e.g., beeping) to indicate that the endoscope 118 has reached maximum translation or rotation.

In position control mode, the command console 200 uses a three-dimensional (3D) map of a patient and pre-determined computer models of the patient to control a surgical instrument, e.g., the endoscope 118. The command console 200 provides control signals to robotic arms 102 of the surgical robotic system 100 to manipulate the endoscope 118 to a target location. Due to the reliance on the 3D map, position control mode requires accurate mapping of the anatomy of the patient.

In some embodiments, users 205 can manually manipulate robotic arms 102 of the surgical robotic system 100 without using the command console 200. During setup in a surgical operating room, the users 205 may move the robotic arms 102, endoscopes 118, and other surgical equipment to access a patient. The surgical robotic system 100 may rely on force feedback and inertia control from the users 205 to determine appropriate configuration of the robotic arms 102 and equipment.

The display modules 202 may include electronic monitors, virtual reality viewing devices, e.g., goggles or glasses, and/or other means of display devices. In some embodiments, the display modules 202 are integrated with the control modules, for example, as a tablet device with a touchscreen. Further, the user 205 can both view data and input commands to the surgical robotic system 100 using the integrated display modules 202 and control modules.

The display modules 202 can display 3D images using a stereoscopic device, e.g., a visor or goggle. The 3D images provide an "endo view" (i.e., endoscopic view), which is a computer 3D model illustrating the anatomy of a patient. The "endo view" provides a virtual environment of the patient's interior and an expected location of an endoscope 118 inside the patient. A user 205 compares the "endo view" model to actual images captured by a camera to help mentally orient and confirm that the endoscope 118 is in the correct—or approximately correct—location within the patient. The "endo view" provides information about anatomical structures, e.g., the shape of an intestine or colon of the patient, around the distal end of the endoscope 118. The display modules 202 can simultaneously display the 3D model and computerized tomography (CT) scans of the anatomy the around distal end of the endoscope 118. Further, the display modules 202 may overlay the already determined navigation paths of the endoscope 118 on the 3D model and scans/images generated based on preoperative model data (e.g., CT scans).

In some embodiments, a model of the endoscope 118 is displayed with the 3D models to help indicate a status of a surgical procedure. For example, the CT scans identify a lesion in the anatomy where a biopsy may be necessary. During operation, the display modules 202 may show a reference image captured by the endoscope 118 corresponding to the current location of the endoscope 118. The display modules 202 may automatically display different views of the model of the endoscope 118 depending on user settings and a particular surgical procedure. For example, the display modules 202 show an overhead fluoroscopic view of the endoscope 118 during a navigation step as the endoscope 118 approaches an operative region of a patient.

III. Instrument Device Manipulator

Figure 3A:
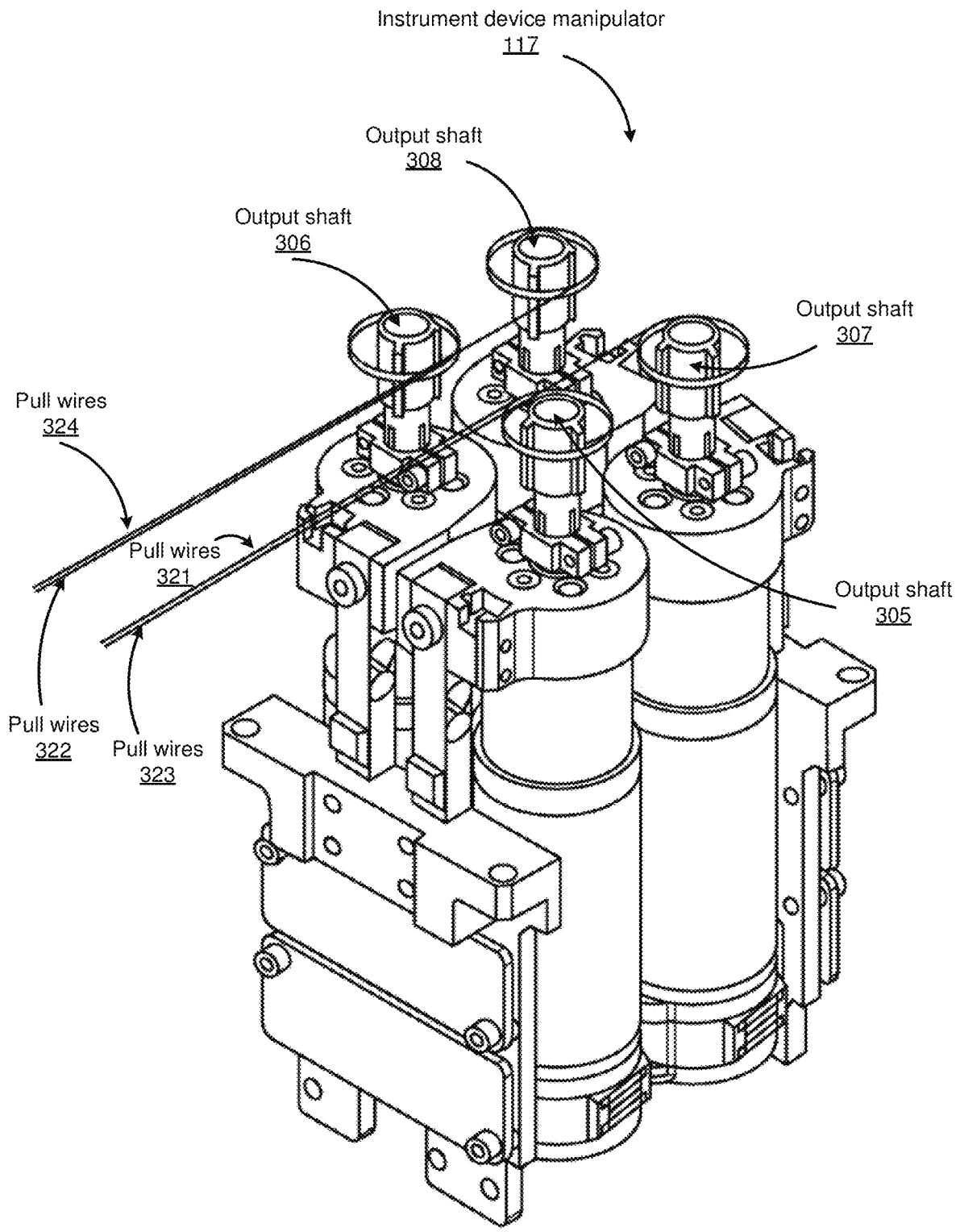
FIG. 3A shows an isometric view of an example independent drive mechanism of the instrument device manipulator (IDM) shown in FIG. 1A, according to one embodiment.

FIG. 3A shows an isometric view of an example independent drive mechanism of the IDM 117 shown in FIG. 1, according to one embodiment. The independent drive mechanism can tighten or loosen the pull wires 321, 322, 323, and 324 (e.g., independently from each other) of an endoscope by rotating the output shafts 305, 306, 307, and 308 of the IDM 117, respectively. Just as the output shafts 305, 306, 307, and 308 transfer force down pull wires 321, 322, 323, and 324, respectively, through angular motion, the pull wires 321, 322, 323, and 324 transfer force back to the output shafts. The IDM 117 and/or the surgical robotic system 100 can measure the transferred force using a sensor, e.g., a strain gauge further described below.

Figure 3B:
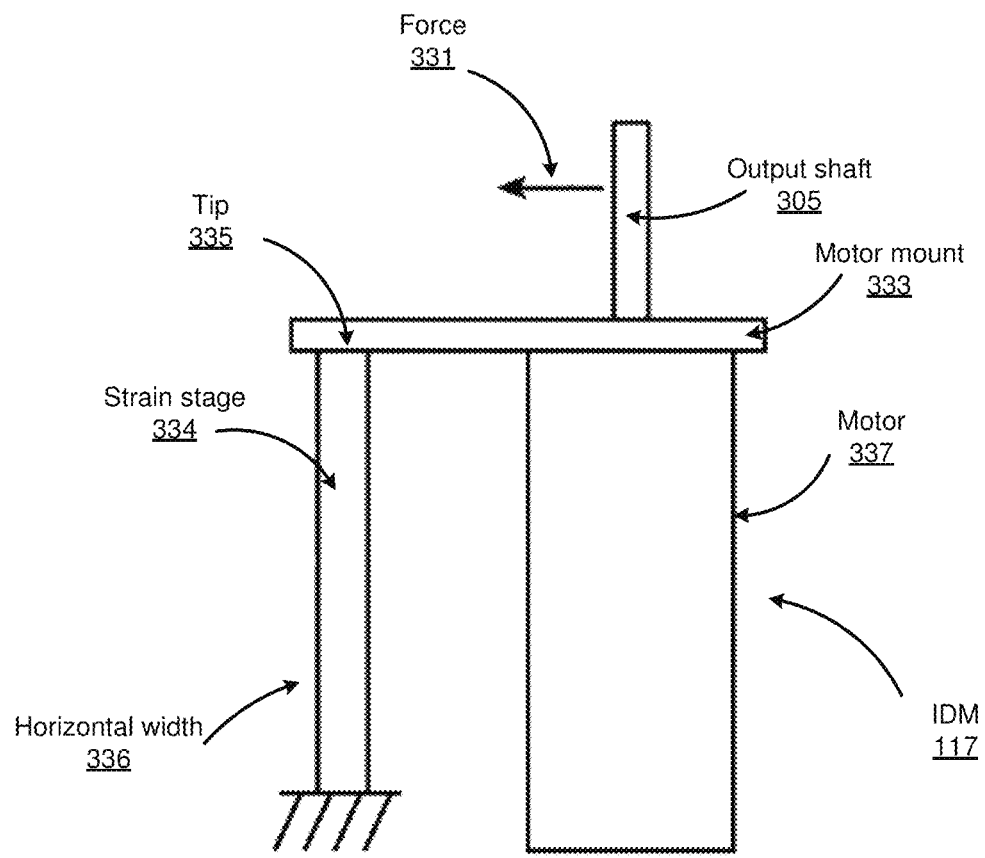
FIG. 3B shows a conceptual diagram that shows how forces may be measured by a strain gauge of the independent drive mechanism shown in FIG. 3A, according to one embodiment.

FIG. 3B shows a conceptual diagram that shows how forces may be measured by a strain gauge 334 of the independent drive mechanism shown in FIG. 3A, according to one embodiment. A force 331 may direct away from the output shaft 305 coupled to the motor mount 333 of the motor 337. Accordingly, the force 331 results in horizontal displacement of the motor mount 333. Further, the strain gauge 334 horizontally coupled to the motor mount 333 experiences strain in the direction of the force 331. The strain may be measured as a ratio of the horizontal displacement of the tip 335 of strain gauge 334 to the overall horizontal width 336 of the strain gauge 334.

In some embodiments, the IDM 117 includes additional sensors, e.g., inclinometers or accelerometers, to determine an orientation of the IDM 117. Based on measurements from the additional sensors and/or the strain gauge 334, the surgical robotic system 100 can calibrate readings from the strain gauge 334 to account for gravitational load effects. For example, if the IDM 117 is oriented on a horizontal side of the IDM 117, the weight of certain components of the IDM 117 may cause a strain on the motor mount 333. Accordingly, without accounting for gravitational load effects, the strain gauge 334 may measure strain that did not result from strain on the output shafts.

IV. Endoscope

Figure 4A:
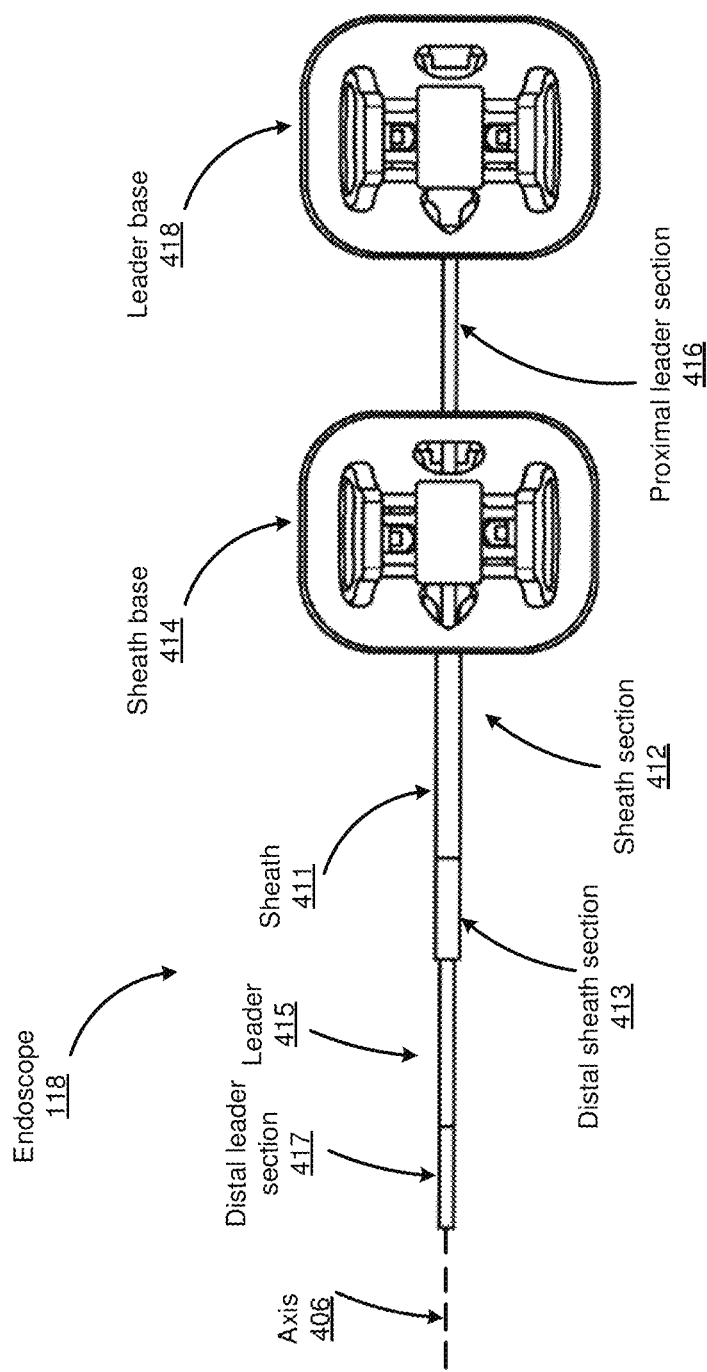
FIG. 4A shows a top view of an example endoscope, according to one embodiment.

FIG. 4A shows a top view of an example endoscope 118, according to one embodiment. The endoscope 118 includes a leader 415 tubular component nested or partially nested inside and longitudinally-aligned with a sheath 411 tubular component. The sheath 411 includes a proximal sheath section 412 and distal sheath section 413. The leader 415 has a smaller outer diameter than the sheath 411 and includes a proximal leader section 416 and distal leader section 417. The sheath base 414 and the leader base 418 actuate the distal sheath section 413 and the distal leader section 417, respectively, for example, based on control signals from a user of a surgical robotic system 100. The sheath base 414 and the leader base 418 are, e.g., part of the IDM 117 shown in FIG. 1.

Both the sheath base 414 and the leader base 418 include drive mechanisms (e.g., the independent drive mechanism further described with reference to FIG. 3A-B in Section III. Instrument Device Manipulator) to control pull wires coupled to the sheath 411 and leader 415. For example, the sheath base 414 generates tensile loads on pull wires coupled to the sheath 411 to deflect the distal sheath section 413. Similarly, the leader base 418 generates tensile loads on pull wires coupled to the leader 415 to deflect the distal leader section 417. Both the sheath base 414 and leader base 418 may also include couplings for the routing of pneumatic pressure, electrical power, electrical signals, or optical signals from IDMs to the sheath 411 and leader 414, respectively. A pull wire may include a steel coil pipe along the length of the pull wire within the sheath 411 or the leader 415, which transfers axial compression back to the origin of the load, e.g., the sheath base 414 or the leader base 418, respectively.

The endoscope 118 can navigate the anatomy of a patient with ease due to the multiple degrees of freedom provided by pull wires coupled to the sheath 411 and the leader 415. For example, four or more pull wires may be used in either the sheath 411 and/or the leader 415, providing eight or more degrees of freedom. In other embodiments, up to three pull wires may be used, providing up to six degrees of freedom. The sheath 411 and leader 415 may be rotated up to 360 degrees along a longitudinal axis 406, providing more degrees of motion. The combination of rotational angles and multiple degrees of freedom provides a user of the surgical robotic system 100 with a user friendly and instinctive control of the endoscope 118.

Figure 4B:
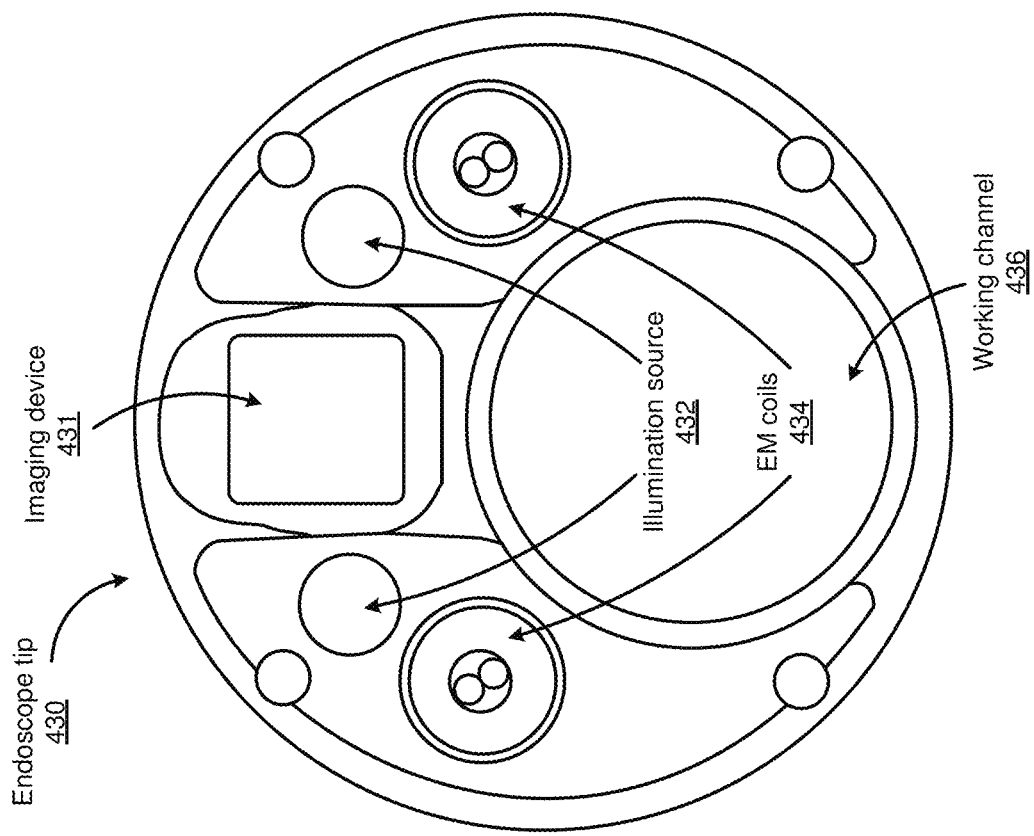
FIG. 4B shows an example endoscope tip of the endoscope shown in FIG. 4A, according to one embodiment.

FIG. 4B illustrates an example endoscope tip 430 of the endoscope 118 shown in FIG. 4A, according to one embodiment. In FIG. 4B, the endoscope tip 430 includes an imaging device 431 (e.g., a camera), illumination sources 432, and ends of EM coils 434. The illumination sources 432 provide light to illuminate an interior portion of an anatomical space. The provided light allows the imaging device 431 to record images of that space, which can then be transmitted to a computer system such as command console 200 for processing as described herein. Electromagnetic (EM) coils 434 located on the tip 430 may be used with an EM tracking system to detect the position and orientation of the endoscope tip 430 while it is disposed within an anatomical system. In some embodiments, the coils may be angled to provide sensitivity to EM fields along different axes, giving the ability to measure a full 6 degrees of freedom: three positional and three angular. In other embodiments, only a single coil may be disposed within the endoscope tip 430, with its axis oriented along the endoscope shaft of the endoscope 118; due to the rotational symmetry of such a system, it is insensitive to roll about its axis, so only 5 degrees of freedom may be detected in such a case. The endoscope tip 430 further comprises a working channel 436 through which surgical instruments, such as biopsy needles, may be inserted along the endoscope shaft, allowing access to the area near the endoscope tip.

V. Registration Transform of EM System to 3D Model

V. A. Schematic Setup of an EM Tracking System

Figure 5:
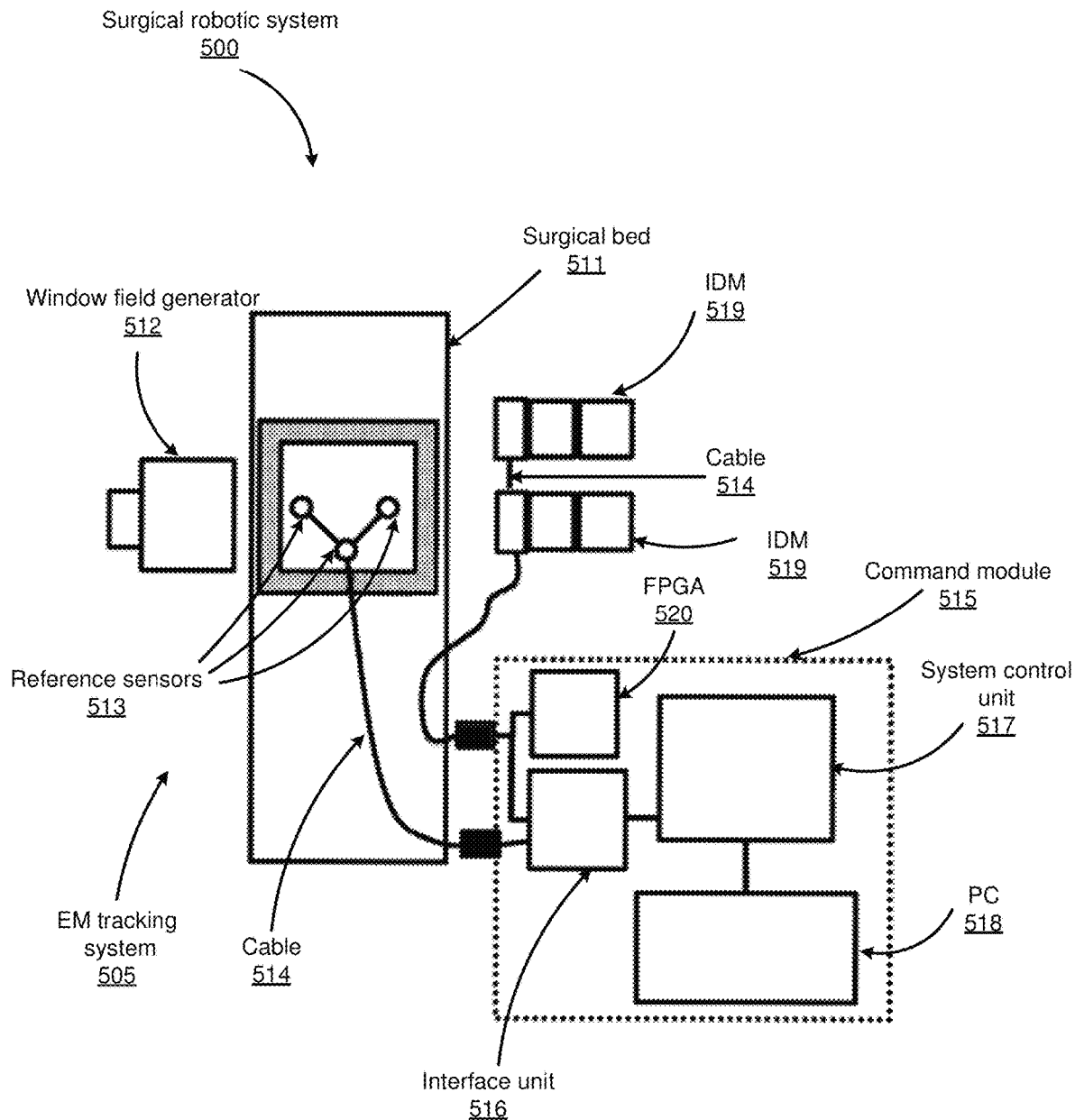
FIG. 5 shows an example schematic setup of an EM tracking system included in a surgical robotic system, according to one embodiment.

FIG. 5 shows an example schematic setup of an EM tracking system 505 included in a surgical robotic system 500, according to one embodiment. In FIG. 5, multiple robot components (e.g., window field generator, reference sensors as described below) are included in the EM tracking system 505. The robotic surgical system 500 includes a surgical bed 511 to hold a patient's body. Beneath the bed 511 is the window field generator (WFG) 512 configured to sequentially activate a set of EM coils (e.g., the EM coils 434 shown in FIG. 4B). The WFG 512 generates an alternating current (AC) magnetic field over a wide volume; for example, in some cases it may create an AC field in a volume of about 0.5×0.5×0.5 m.

Additional fields may be applied by further field generators to aid in tracking instruments within the body. For example, a planar field generator (PFG) may be attached to a system arm adjacent to the patient and oriented to provide an EM field at an angle. Reference sensors 513 may be placed on the patient's body to provide local EM fields to further increase tracking accuracy. Each of the reference sensors 513 may be attached by cables 514 to a command module 515. The cables 514 are connected to the command module 515 through interface units 516 which handle communications with their respective devices as well as providing power. The interface unit 516 is coupled to a system control unit (SCU) 517 which acts as an overall interface controller for the various entities mentioned above. The SCU 517 also drives the field generators (e.g., WFG 512), as well as collecting sensor data from the interface units 516, from which it calculates the position and orientation of sensors within the body. The SCU 517 may be coupled to a personal computer (PC) 518 to allow user access and control.

The command module 515 is also connected to the various IDMs 519 coupled to the surgical robotic system 500 as described herein. The IDMs 519 are typically coupled to a single surgical robotic system (e.g., the surgical robotic system 500) and are used to control and receive data from their respective connected robotic components; for example, robotic endoscope tools or robotic arms. As described above, as an example, the IDMs 519 are coupled to an endoscopic tool (not shown here) of the surgical robotic system 500.

The command module 515 receives data passed from the endoscopic tool. The type of received data depends on the corresponding type of instrument attached. For example, example received data includes sensor data (e.g., image data, EM data), robot data (e.g., endoscopic and IDM physical motion data), control data, and/or video data. To better handle video data, a field-programmable gate array (FPGA) 520 may be configured to handle image processing. Comparing data obtained from the various sensors, devices, and field generators allows the SCU 517 to precisely track the movements of different components of the surgical robotic system 500, and for example, positions and orientations of these components.

In order to track a sensor through the patient's anatomy, the EM tracking system 505 may require a process known as "registration," where the system finds the geometric transformation that aligns a single object between different coordinate systems. For instance, a specific anatomical site on a patient has two different representations in the 3D model coordinates and in the EM sensor coordinates. To be able to establish consistency and common language between these two different coordinate systems, the EM tracking system 505 needs to find the transformation that links these two representations, i.e., registration. For example, the position of the EM tracker relative to the position of the EM field generator may be mapped to a 3D coordinate system to isolate a location in a corresponding 3D model.

V. B. 3D Model Representation

Figure 6A:
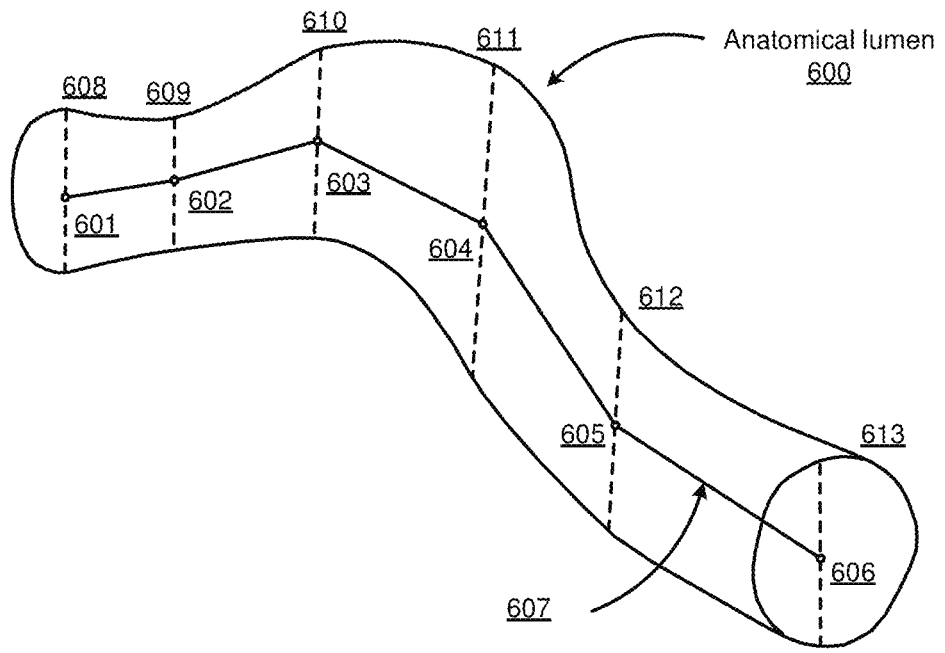
FIGS. 6A-6B show an example anatomical lumen and an example 3D model of the anatomical lumen, according to one embodiment.
Figure 6B:
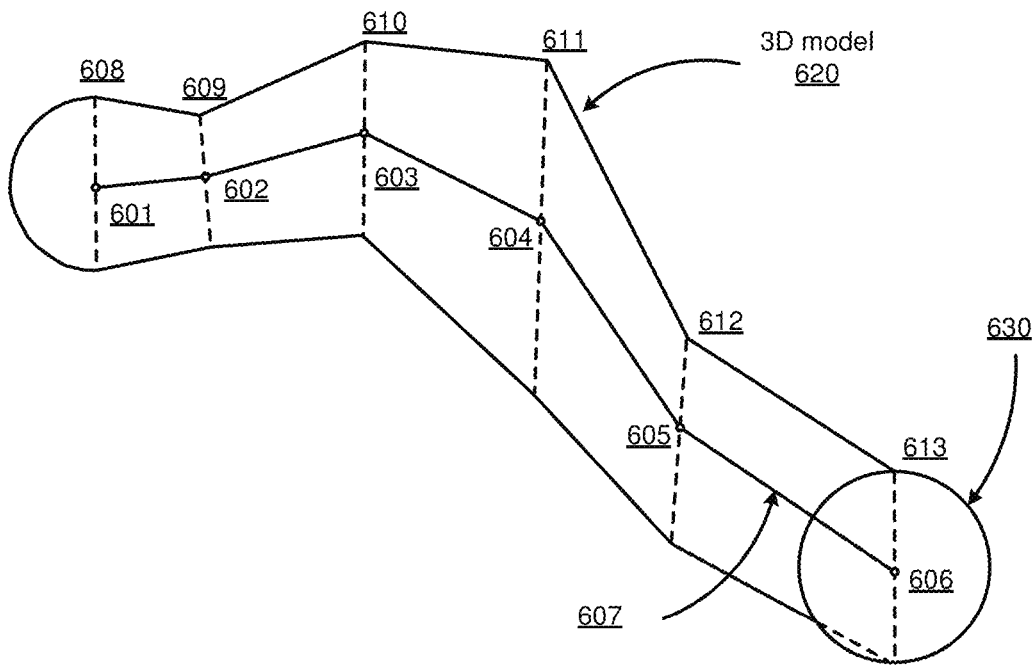

FIGS. 6A-6B show an example anatomical lumen 600 and an example 3D model 620 of the anatomical lumen, according to one embodiment. More specifically, FIGS. 6A-6B illustrate the relationships of centerline coordinates, diameter measurements and anatomical spaces between the actual anatomical lumen 600 and its 3D model 620. In FIG. 6A, the anatomical lumen 600 is roughly tracked longitudinally by centerline coordinates 601, 602, 603, 604, 605, and 606 where each centerline coordinate roughly approximates the center of the tomographic slice of the lumen. The centerline coordinates are connected and visualized by a centerline 607. The volume of the lumen can be further visualized by measuring the diameter of the lumen at each centerline coordinate, e.g., coordinates 608, 609, 610, 611, 612, and 613 represent the measurements of the lumen 600 corresponding to coordinates 601, 602, 603, 604, 605, and 606.

FIG. 6B shows the example 3D model 620 of the anatomical lumen 600 shown in FIG. 6A, according to one embodiment. In FIG. 6B, the anatomical lumen 600 is visualized in 3D space by first locating the centerline coordinates 601, 602, 603, 604, 605, and 606 in 3D space based on the centerline 607. As one example, at each centerline coordinate, the lumen diameter is visualized as a 2D circular space (e.g., the 2D circular space 630) with diameters 608, 609, 610, 611, 612, and 613. By connecting those 2D circular spaces to form a 3D space, the anatomical lumen 600 is approximated and visualized as the 3D model 620. More accurate approximations may be determined by increasing the resolution of the centerline coordinates and measurements, i.e., increasing the density of centerline coordinates and measurements for a given lumen or subsection. Centerline coordinates may also include markers to indicate point of interest for the physician, including lesions.

In some embodiments, a pre-operative software package is also used to analyze and derive a navigation path based on the generated 3D model of the anatomical space. For example, the software package may derive a shortest navigation path to a single lesion (marked by a centerline coordinate) or to several lesions. This navigation path may be presented to the operator intra-operatively either in two-dimensions or three-dimensions depending on the operator's preference. In certain implementations, as discussed below, the navigation path (or at a portion thereof) may be pre-operatively selected by the operator. The path selection may include identification of one or more target locations (also simply referred to as a "target") within the patient's anatomy.

Figure 7:
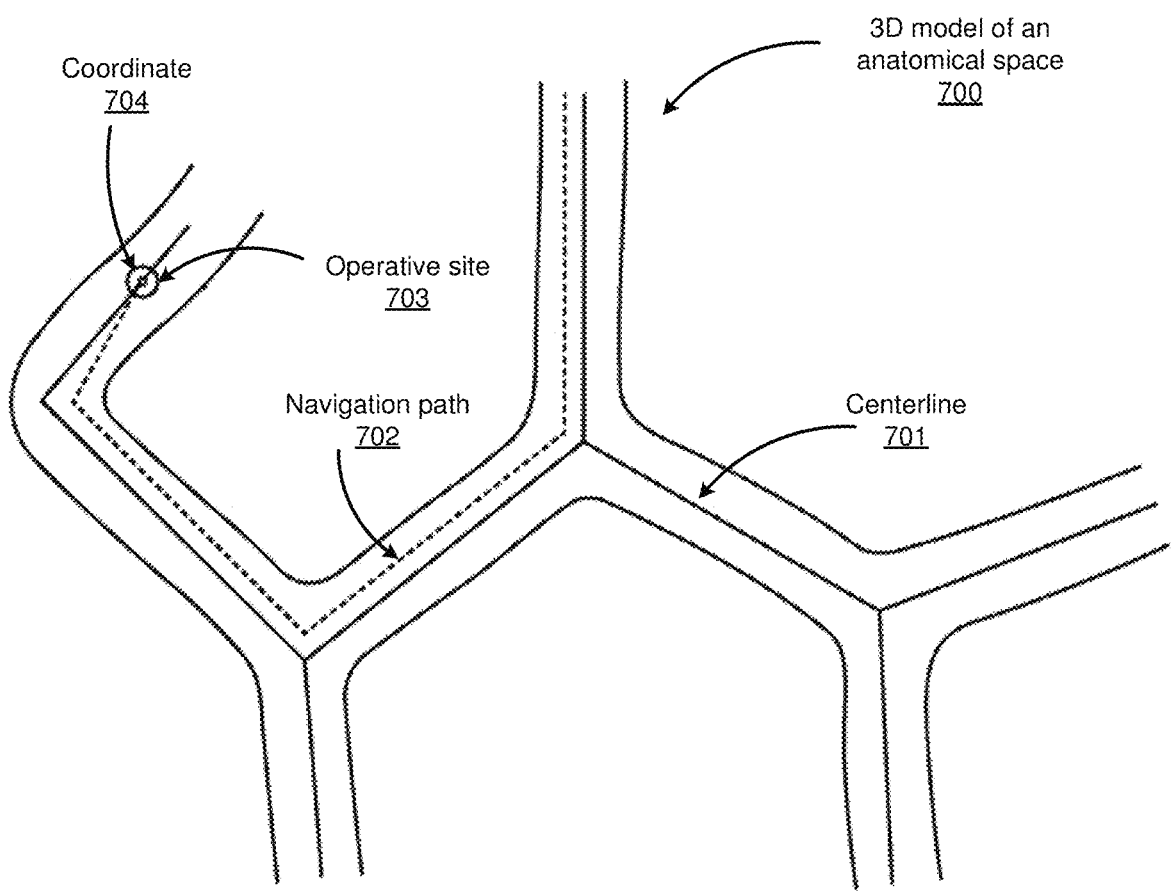
FIG. 7 shows a computer-generated 3D model representing an anatomical space, according to one embodiment.

FIG. 7 shows a computer-generated 3D model 700 representing an anatomical space, according to one embodiment. As discussed above in FIGS. 6A-6B, the 3D model 700 may be generated using a centerline 701 that was obtained by reviewing CT scans that were generated preoperatively. In some embodiments, computer software may be able to map a navigation path 702 within the tubular network to access an operative site 703 (or other target) within the 3D model 700. In some embodiments, the operative site 703 may be linked to an individual centerline coordinate 704, which allows a computer algorithm to topologically search the centerline coordinates of the 3D model 700 for the optimum path 702 within the tubular network. In certain embodiments, the topological search for the path 702 may be constrained by certain operator selected parameters, such as the location of one or more targets, one or more waypoints, etc.

In some embodiments, the distal end of the endoscopic tool within the patient's anatomy is tracked, and the tracked location of the endoscopic tool within the patient's anatomy is mapped and placed within a computer model, which enhances the navigational capabilities of the tubular network. In order to track the distal working end of the endoscopic tool, i.e., location and orientation of the working end, a number of approaches may be employed, either individually or in combination.

In a sensor-based approach to localization, a sensor, such as an electromagnetic (EM) tracker, may be coupled to the distal working end of the endoscopic tool to provide a real-time indication of the progression of the endoscopic tool. In EM-based tracking, an EM tracker, embedded in the endoscopic tool, measures the variation in the electromagnetic field created by one or more EM transmitters. The transmitters (or field generators), may be placed close to the patient (e.g., as part of the surgical bed) to create a low intensity magnetic field. This induces small-currents in sensor coils in the EM tracker, which are correlated to the distance and angle between the sensor and the generator. The electrical signal may then be digitized by an interface unit (on-chip or PCB) and sent via cables/wiring back to the system cart and then to the command module. The data may then be processed to interpret the current data and calculate the precise location and orientation of the sensor relative to the transmitters. Multiple sensors may be used at different locations in the endoscopic tool, for instance in leader and sheath in order to calculate the individual positions of those components. Accordingly, based on readings from an artificially-generated EM field, the EM tracker may detect changes in field strength as it moves through the patient's anatomy.

V. C. On-the-Fly EM Registration

Figure 8B:
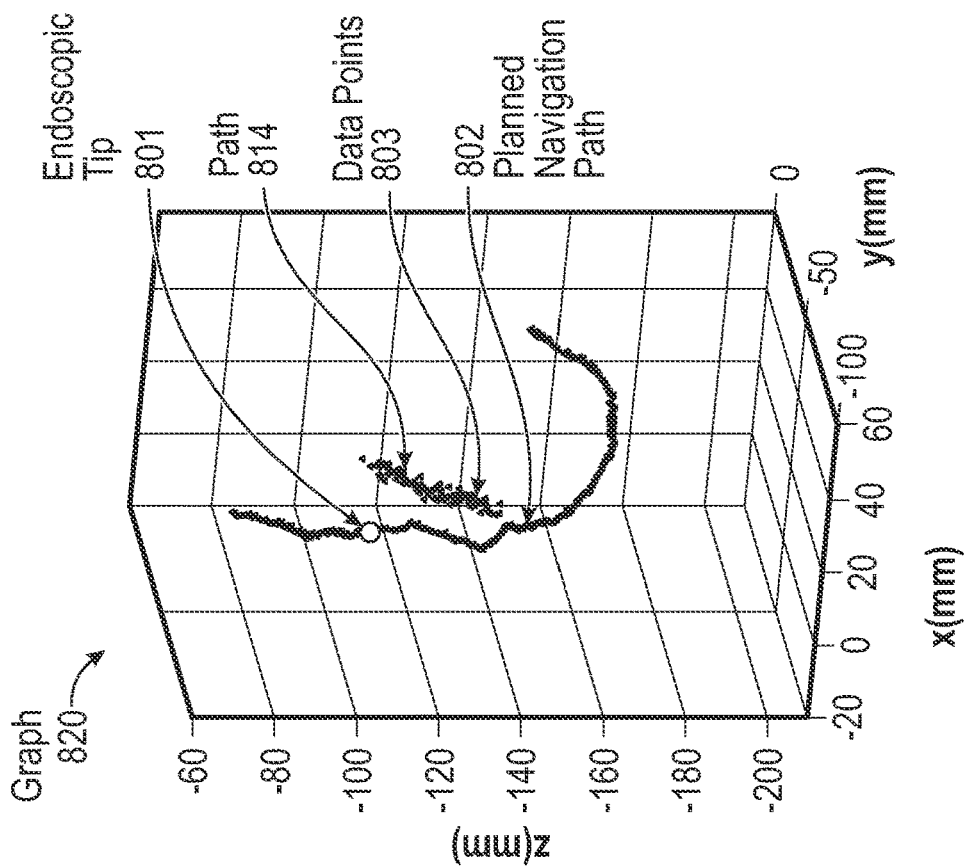
FIGS. 8A-8D show example graphs illustrating on-the-fly registration of an EM system to a 3D model of a path through a tubular network, according to one embodiment.
Figure 8A:
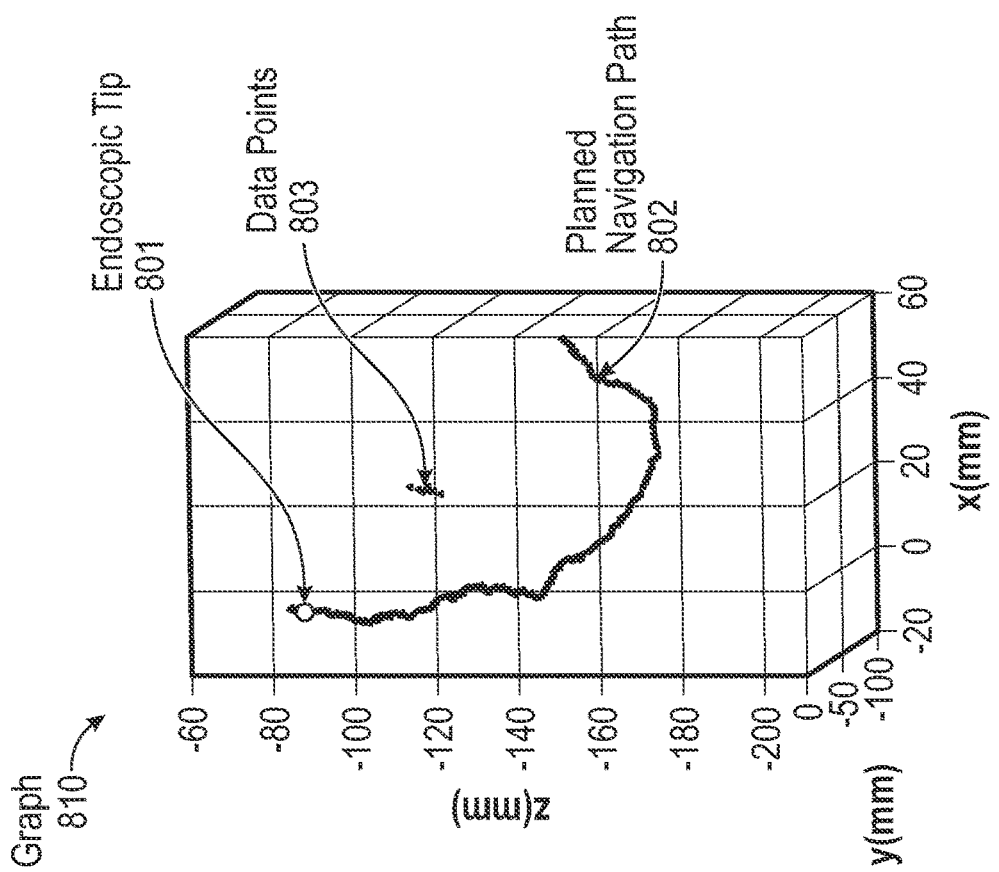

FIGS. 8A-8D show example graphs 810-840 illustrating on-the-fly registration of an EM system to a 3D model of a path through a tubular network, according to one embodiment. The navigation configuration system described herein allows for on-the-fly registration of the EM coordinates to the 3D model coordinates without the need for independent registration prior to an endoscopic procedure. In more detail, FIG. 8A shows that the coordinate systems of the EM tracking system and the 3D model are initially not registered to each other, and the graph 810 in FIG. 8A shows the registered (or expected) location of an endoscope tip 801 moving along a planned navigation path 802 through a branched tubular network (not shown here), and the registered location of the instrument tip 801 as well as the planned path 802 are derived from the 3D model. The actual position of the tip is repeatedly measured by the EM tracking system 505, resulting in multiple measured location data points 803 based on EM data. As shown in FIG. 8A, the data points 803 derived from EM tracking are initially located far from the registered location of the endoscope tip 801 expected from the 3D model, reflecting the lack of registration between the EM coordinates and the 3D model coordinates. There may be several reasons for this, for example, even if the endoscope tip is being moved relatively smoothly through the tubular network, there may still be some visible scatter in the EM measurement, due to breathing movement of the lungs of the patient.

The points on the 3D model may also be determined and adjusted based on correlation between the 3D model itself, image data received from optical sensors (e.g., cameras) and robot data from robot commands. The 3D transformation between these points and collected EM data points will determine the initial registration of the EM coordinate system to the 3D model coordinate system.

FIG. 8B shows a graph 820 at a later temporal stage compared with the graph 810, according to one embodiment. More specifically, the graph 820 shows the expected location of the endoscope tip 801 expected from the 3D model has been moved farther along the preplanned navigation path 802, as illustrated by the shift from the original expected position of the instrument tip 801 shown in FIG. 8A along the path to the position shown in FIG. 8B. During the EM tracking between generation of the graph 810 and generation of graph 820, additional data points 803 have been recorded by the EM tracking system but the registration has not yet been updated based on the newly collected EM data. As a result, the data points 803 in FIG. 8B are clustered along a visible path 814, but that path differs in location and orientation from the planned navigation path 802 the endoscope tip is being directed by the operator to travel along. Eventually, once sufficient data (e.g., EM data) is accumulated, compared with using only the 3D model or only the EM data, a relatively more accurate estimate can be derived from the transform needed to register the EM coordinates to those of the 3D model. The determination of sufficient data may be made by threshold criteria such as total data accumulated or number of changes of direction. For example, in a branched tubular network such as a bronchial tube network, it may be judged that sufficient data have been accumulated after arriving at two branch points.

Figure 8D:
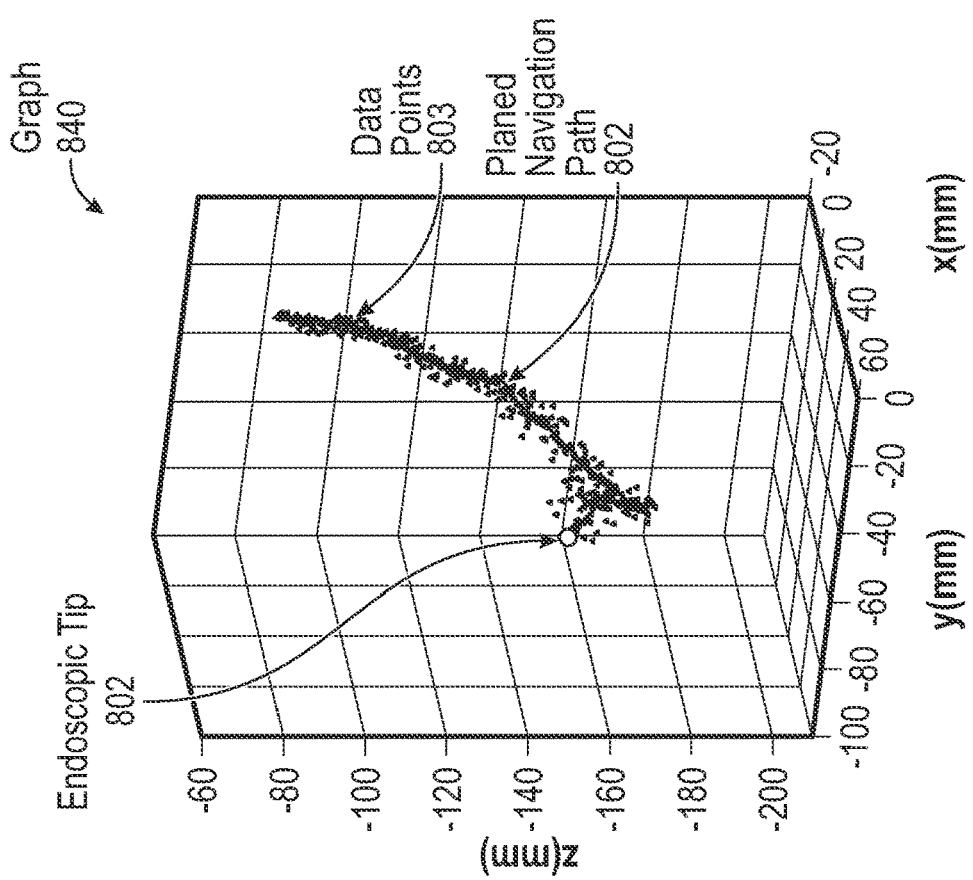
Figure 8C:
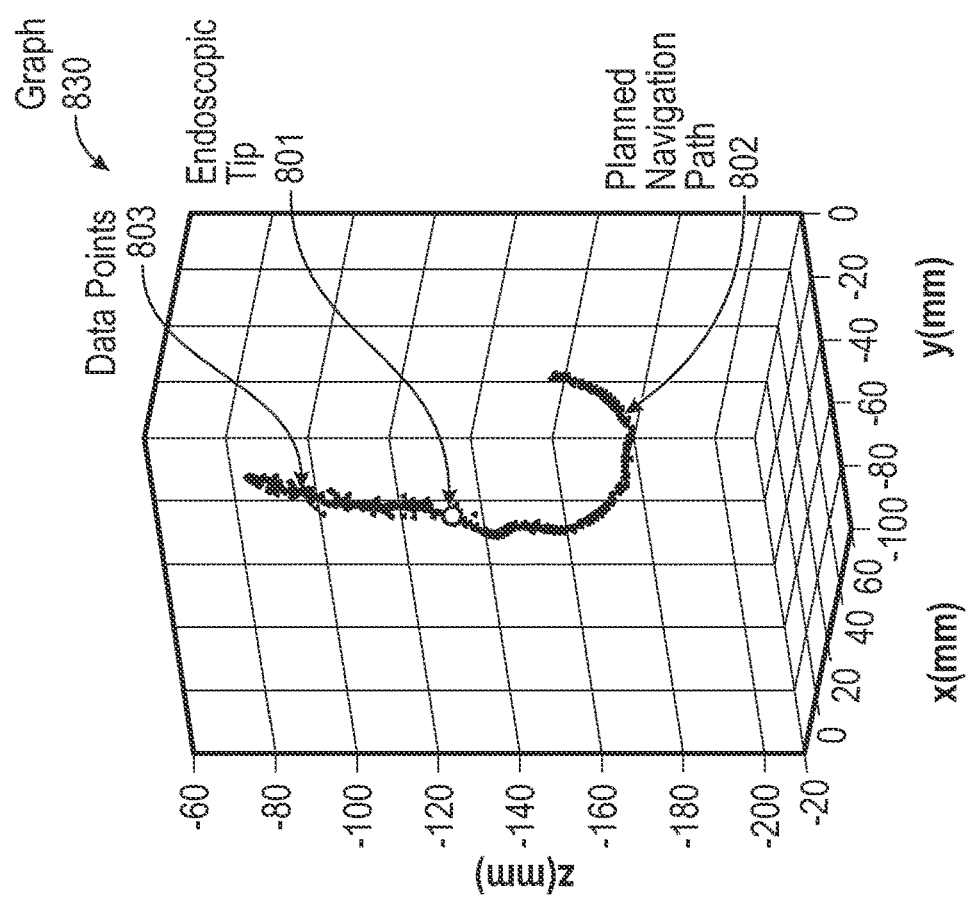

FIG. 8C shows a graph 830 shortly after the navigation configuration system has accumulated a sufficient amount of data to estimate the registration transform from EM to 3D model coordinates, according to one embodiment. The data points 803 in FIG. 8C have now shifted from their previous position as shown in FIG. 8B as a result of the registration transform. As shown in FIG. 8C, the data points 803 derived from EM data is now falling along the planned navigation path 802 derived from the 3D model, and each data point among the data points 803 is now reflecting a measurement of the expected position of endoscope tip 801 in the coordinate system of the 3D model. In some embodiments, as further data are collected, the registration transform may be updated to increase accuracy. In some cases, the data used to determine the registration transformation may be a subset of data chosen by a moving window, so that the registration may change over time, which gives the ability to account for changes in the relative coordinates of the EM and 3D models—for example, due to movement of the patient.

FIG. 8D shows an example graph 840 in which the expected location of the endoscope tip 801 has reached the end of the planned navigation path 802, arriving at the target location in the tubular network, according to one embodiment. As shown in FIG. 8D, the recorded EM data points 803 is now generally tracks along the planned navigation path 802, which represents the tracking of the endoscope tip throughout the procedure. Each data point reflects a transformed location due to the updated registration of the EM tracking system to the 3D model.

In some embodiments, each of the graphs shown in FIGS. 8A-8D can be shown sequentially on a display visible to a user as the endoscope tip is advanced in the tubular network. In some embodiments, the processor can be configured with instructions from the navigation configuration system such that the model shown on the display remains substantially fixed when the measured data points are registered to the display by shifting of the measured path shown on the display in order to allow the user to maintain a fixed frame of reference and to remain visually oriented on the model and on the planned path shown on the display.

FIGS. 8E-8F show the effect of an example registration of the EM system to a 3D model of a branched tubular network, according to one embodiment. In FIGS. 8E-8F, 3D graphs showing electromagnetic tracking data 852 and a model of a patient's bronchial system 854 are illustrated without (shown in FIG. 8E) and with (shown in FIG. 8F) a registration transform. In FIG. 8E, without registration, tracking data 860 have a shape that corresponds to a path through the bronchial system 854, but that shape is subjected to an arbitrary offset and rotation. In FIG. 8F, by applying the registration, the tracking data 852 are shifted and rotated, so that they correspond to a path through the bronchial system 854.

VI. Navigation Configuration System

VI. A. High-Level Overview of Navigation Configuration System

Figure 9A:
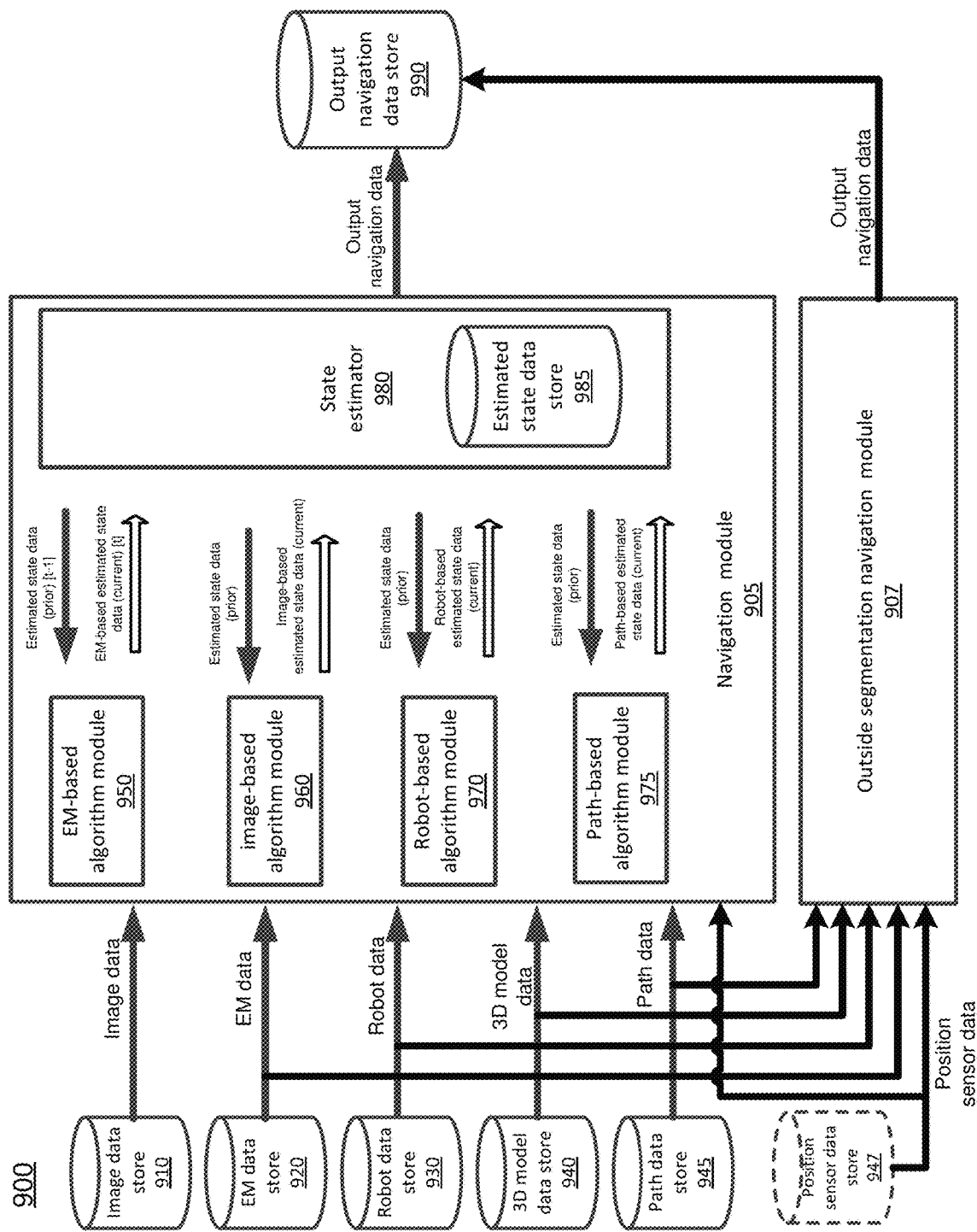
FIG. 9A shows a high-level overview of an example block diagram of a navigation configuration system, according to one embodiment.
Figure 9B:
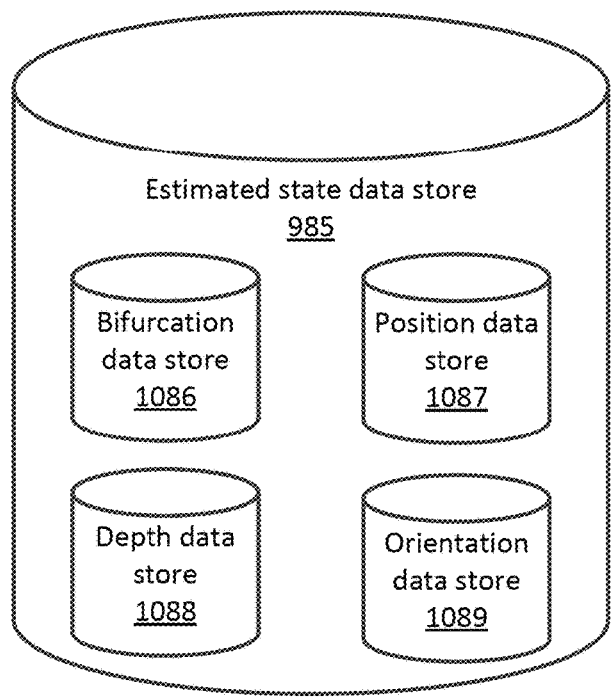
FIG. 9B shows an example block diagram of the estimated state data store included in the state estimator, according to one embodiment.

FIGS. 9A-9B show example block diagrams of a navigation configuration system 900, according to one embodiment. More specifically, FIG. 9A shows a high-level overview of an example block diagram of the navigation configuration system 900, according to one embodiment. In FIG. 9A, the navigation configuration system 900 includes multiple input data stores, a navigation module 905 that receives various types of input data from the multiple input data stores, an outside segmentation navigation module 905 that receives various types of input data from the multiple input data stores, and an output navigation data store 990 that receives output navigation data from the navigation module. The block diagram of the navigation configuration system 900 shown in FIG. 9A is merely one example, and in alternative embodiments not shown, the navigation configuration system 900 can include different and/or addition entities. Likewise, functions performed by various entities of the system 900 may differ according to different embodiments. The navigation configuration system 900 may be similar to the navigational system described in U.S. Patent Publication No. 2017/0084027, published on Mar. 23, 2017, the entirety of which is incorporated herein by reference.

The input data, as used herein, refers to raw data gathered from and/or processed by input devices (e.g., command module, optical sensor, EM sensor, IDM) for generating estimated state information for the endoscope as well as output navigation data. The multiple input data stores 910-945 include an image data store 910, an EM data store 920, a robot data store 930, a 3D model data store 940, and a path data store 945. Each type of the input data stores 910-945 stores the name-indicated type of data for access and use by a navigation module 905. Image data may include one or more image frames captured by the imaging device at the instrument tip, as well as information such as frame rates or timestamps that allow a determination of the time elapsed between pairs of frames. Robot data may include data related to physical movement of the medical instrument or part of the medical instrument (e.g., the instrument tip or sheath) within the tubular network. Example robot data includes command data instructing the instrument tip to reach a specific anatomical site and/or change its orientation (e.g., with a specific pitch, roll, yaw, insertion, and retraction for one or both of a leader and a sheath) within the tubular network, insertion data representing insertion movement of the part of the medical instrument (e.g., the instrument tip or sheath), IDM data, and mechanical data representing mechanical movement of an elongate member of the medical instrument, for example motion of one or more pull wires, tendons or shafts of the endoscope that drive the actual movement of the medial instrument within the tubular network. EM data may be collected by EM sensors and/or the EM tracking system as described above. 3D model data may be derived from 2D CT scans as described above. Path data includes the planned navigation path (e.g., the navigation path 702) which may be generated by a topological search of the tubular network to one or more targets. The multiple input data stores may also include other types of data stores such as an optional position sensor data store 947. In certain implementations, the position sensor data store 947 may store shape sensor data received from a shape sensing fiber positioned within the instrument. The navigation module 905 and/or the outside segmentation navigation module 907 may be configured to receive the position sensor data from the position sensor data store 947 depending on the embodiment.

The output navigation data store 990 receives and stores output navigation data provided by the navigation module 905 and/or the outside segmentation navigation module 907. As described in greater detail below, the system 900 may adjust the weights given to the output navigation data generated by the navigation module 905 and the outside segmentation navigation module 907 based on the position of the instrument with respect to the mapped portion of the luminal network. Output navigation data indicates information to assist in directing the medical instrument through the tubular network to arrive at a particular destination within the tubular network, and is based on estimated state information for the medical instrument at each instant time, the estimated state information including the location and orientation of the medical instrument within the tubular network. In one embodiment, as the medical instrument moves inside the tubular network, the output navigation data indicating updates of movement and location/orientation information of the medical instrument is provided in real time, which better assists its navigation through the tubular network.

To determine the output navigation data, the navigation module 905 and/or the outside segmentation navigation module 907 locates (or determines) the estimated state of the medical instrument within a tubular network. As shown in FIG. 9A, the navigation module 905 further includes various algorithm modules, such as an EM-based algorithm module 950, an image-based algorithm module 960, a robot-based algorithm module 970, and a path-based algorithm module 975, that each may consume mainly certain types of input data and contribute a different type of data to a state estimator 980. As illustrated in FIG. 9A, the different kinds of data output by these modules, labeled EM-based data, the image-based data, the robot-based data, and the path-based data, may be generally referred to as "intermediate data" for sake of explanation. The detailed composition of each algorithm module and of the state estimator 980 is more fully described below.

VI. B. Navigation Module

With reference to the navigation module 905 shown in FIG. 9A, the navigation module 905 includes a state estimator 980 as well as multiple algorithm modules that employ different algorithms for navigating through a tubular network. For clarity of description, the state estimator 980 is described first, followed by the description of the various modules that exchange data with the state estimator 980.

VI. B. 1 State Estimator

The state estimator 980 included in the navigation module 905 receives various intermediate data and provides the estimated state of the instrument tip as a function of time, where the estimated state indicates the estimated location and orientation information of the instrument tip within the tubular network. The estimated state data are stored in the estimated data store 985 that is included in the state estimator 980.

FIG. 9B shows an example block diagram of the estimated state data store 985 included in the state estimator 980, according to one embodiment. The estimated state data store 985 may include a bifurcation data store 1086, a position data store 1087, a depth data store 1088, and an orientation data store 1089, however this particular breakdown of data storage is merely one example, and in alternative embodiments not shown, different and/or additional data stores can be included in the estimated state data store 985.

The various stores introduced above represent estimated state data in a variety of ways. Specifically, bifurcation data refers to the location of the medical instrument with respect to the set of branches (e.g., bifurcation, trifurcation or a division into more than three branches) within the tubular network. For example, the bifurcation data can be set of branch choices elected by the instrument as it traverses through the tubular network, based on a larger set of available branches as provided, for example, by the 3D model which maps the entirety of the tubular network. The bifurcation data can further include information in front of the location of the instrument tip, such as branches (bifurcations) that the instrument tip is near but has not yet traversed through, but which may have been detected, for example, based on the tip's current position information relative to the 3D model, or based on images captured of the upcoming bifurcations.

Position data indicates three-dimensional position of some part of the medical instrument within the tubular network or some part of the tubular network itself. Position data can be in the form of absolute locations or relative locations relative to, for example, the 3D model of the tubular network. As one example, position data can include an indication of the position of the location of the instrument being within a specific branch. The identification of the specific branch may also be stored as a segment identification (ID) which uniquely identifies the specific segment of the model in which the instrument tip is located.

Depth data indicates depth information of the instrument tip within the tubular network. Example depth data includes the total insertion (absolute) depth of the medical instrument into the patient as well as the (relative) depth within an identified branch (e.g., the segment identified by the position data store 1087). Depth data may be determined based on position data regarding both the tubular network and medical instrument.

Orientation data indicates orientation information of the instrument tip, and may include overall roll, pitch, and yaw in relation to the 3D model as well as pitch, roll, raw within an identified branch.

Turning back to FIG. 9A, the state estimator 980 provides the estimated state data back to the algorithm modules for generating more accurate intermediate data, which the state estimator uses to generate improved and/or updated estimated states, and so on forming a feedback loop. For example, as shown in FIG. 9A, the EM-based algorithm module 950 receives prior EM-based estimated state data, also referred to as data associated with timestamp "t−1." The state estimator 980 uses this data to generate "estimated state data (prior)" that is associated with timestamp "t−1." The state estimator 980 then provides the data back to the EM-based algorithm module. The "estimated state data (prior)" may be based on a combination of different types of intermediate data (e.g., robotic data, image data) that is associated with timestamp "t−1" as generated and received from different algorithm modules. Next, the EM-based algorithm module 950 runs its algorithms using the estimated state data (prior) to output to the state estimator 980 improved and updated EM-based estimated state data, which is represented by "EM-based estimated state data (current)" here and associated with timestamp t. This process continues to repeat for future timestamps as well.

As the state estimator 980 may use several different kinds of intermediate data to arrive at its estimates of the state of the medical instrument within the tubular network, the state estimator 980 is configured to account for the various different kinds of errors and uncertainty in both measurement and analysis that each type of underlying data (robotic, EM, image, path) and each type of algorithm module might create or carry through into the intermediate data used for consideration in determining the estimated state. To address these, two concepts are discussed, that of a probability distribution and that of confidence value.

The "probability" of the "probability distribution", as used herein, refers to a likelihood of an estimation of a possible location and/or orientation of the medical instrument being correct. For example, different probabilities may be calculated by one of the algorithm modules indicating the relative likelihood that the medical instrument is in one of several different possible branches within the tubular network. In one embodiment, the type of probability distribution (e.g., discrete distribution or continuous distribution) is chosen to match features of an estimated state (e.g., type of the estimated state, for example continuous position information vs. discrete branch choice). As one example, estimated states for identifying which segment the medical instrument is in for a trifurcation may be represented by a discrete probability distribution, and may include three discrete values of 20%, 30% and 50% representing chance as being in the location inside each of the three branches as determined by one of the algorithm modules. As another example, the estimated state may include a roll angle of the medical instrument of 40±5 degrees and a segment depth of the instrument tip within a branch may be is 4±1 mm, each represented by a Gaussian distribution which is a type of continuous probability distribution. Different methods or modalities can be used to generate the probabilities, which will vary by algorithm module as more fully described below with reference to later figures.

In contrast, the "confidence value," as used herein, reflects a measure of confidence in the estimation of the state provided by one of the algorithms based one or more factors. For the EM-based algorithms, factors such as distortion to EM Field, inaccuracy in EM registration, shift or movement of the patient, and respiration of the patient may affect the confidence in estimation of the state. Particularly, the confidence value in estimation of the state provided by the EM-based algorithms may depend on the particular respiration cycle of the patient, movement of the patient or the EM field generators, and the location within the anatomy where the instrument tip locates. For the image-based algorithms, examples factors that may affect the confidence value in estimation of the state include illumination condition for the location within the anatomy where the images are captured, presence of fluid, tissue, or other obstructions against or in front of the optical sensor capturing the images, respiration of the patient, condition of the tubular network of the patient itself (e.g., lung) such as the general fluid inside the tubular network and occlusion of the tubular network, and specific operating techniques used in, e.g., navigating or image capturing.

For example one factor may be that a particular algorithm has differing levels of accuracy at different depths in a patient's lungs, such that relatively close to the airway opening, a particular algorithm may have a high confidence in its estimations of medical instrument location and orientation, but the further into the bottom of the lung the medical instrument travels that confidence value may drop. Generally, the confidence value is based on one or more systemic factors relating to the process by which a result is determined, whereas probability is a relative measure that arises when trying to determine the correct result from multiple possibilities with a single algorithm based on underlying data.

As one example, a mathematical equation for calculating results of an estimated state represented by a discrete probability distribution (e.g., branch/segment identification for a trifurcation with three values of an estimated state involved) can be as follows:

$$S_1 = C_{EM} * P_{1,EM} + C_{Image} * P_{1,Image} + C_{Robot} * P_{1,Robot};$$

$$S_2 = C_{EM} * P_{2,EM} + C_{Image} * P_{2,Image} + C_{Robot} * P_{2,Robot};$$

$$S_3 = C_{EM} * P_{3,EM} + C_{Image} * P_{3,Image} + C_{Robot} * P_{3,Robot}$$

In the example mathematical equation above, $S_i (i=1,2,3)$ represents possible example values of an estimated state in a case where 3 possible segments are identified or present in the 3D model, $C_{EM}$, $C_{Image}$, and $C_{Robot}$ represents confidence value corresponding to EM-based algorithm, image-based algorithm, and robot-based algorithm and $P_{i,EM}$, $P_{i,Image}$, and $P_{i,Robot}$ represent the probabilities for segment i.

To better illustrate the concepts of probability distributions and confidence value associated with estimate states, a detailed example is provided here. In this example, a user is trying to identify segment where an instrument tip is located in a certain trifurcation within a central airway (the predicted region) of the tubular network, and three algorithms modules are used including EM-based algorithm, image-based algorithm, and robot-based algorithm. In this example, a probability distribution corresponding to the EM-based algorithm may be 20% in the first branch, 30% in the second branch, and 50% in the third (last) branch, and the confidence value applied to this EM-based algorithm and the central airway is 80%. For the same example, a probability distribution corresponding to the image-based algorithm may be 40%, 20%, 40% for the first, second, and third branch, and the confidence value applied to this image-based algorithm is 30%; while a probability distribution corresponding to the robot-based algorithm may be 10%, 60%, 30% for the first, second, and third branch, and the confidence value applied to this image-based algorithm is 20%. The difference of confidence values applied to the EM-based algorithm and the image-based algorithm indicates that the EM-based algorithm may be a better choice for segment identification in the central airway, compared with the image-based algorithm. An example mathematical calculation of a final estimated state can be:

for the first branch: 20%*80%+40%*30%+10%*20%=30%; for the second branch: 30%*80%+20%*30%+60%*20%=42%; and for the third branch: 50%*80%+40%*30%+30%*20%=58%.

In this example, the output estimated state for the instrument tip can be the result values (e.g., the resulting 30%, 42% and 58%), or derivative value from these result values such as the determination that the instrument tip is in the third branch. Although this example describes the use of the algorithm modules include EM-based algorithm, image-based algorithm, and robot-based algorithm, the estimation of the state for the instrument tip can also be provided based on different combinations of the various algorithms modules, including the path-based algorithm.

As above the estimated state may be represented in a number of different ways. For example, the estimated state may further include an absolute depth from airway to location of the tip of the instrument, as well as a set of data representing the set of branches traversed by the instrument within the tubular network, the set being a subset of the entire set of branches provided by the 3D model of the patient's lungs, for example. The application of probability distribution and confidence value on estimated states allows improved accuracy of estimation of location and/or orientation of the instrument tip within the tubular network.

VI. B. 2 Overview of Path-Based Navigation

As shown in FIG. 9A, the algorithm modules include an EM-based algorithm module 950, an image-based algorithm module 960, a robot-based algorithm module 970, and a path-based algorithm module 975. The algorithm modules shown in FIG. 9A is merely one example, and in alternative embodiments, different and/additional algorithm modules involving different and/or additional navigation algorithms can also be included in the navigation module 905. Further details and example embodiments of the EM-based algorithm module 950, the image-based algorithm module 960, and the robot-based algorithm module 970 are described in U.S. Patent Publication No. 2017/0084027, referenced above.

Figure 10:
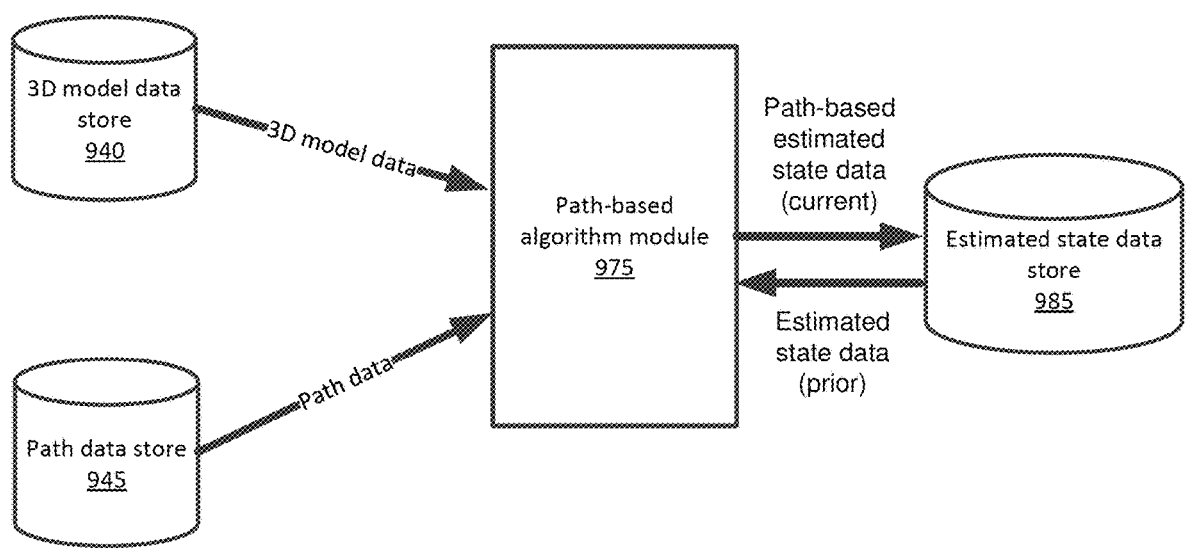
FIG. 10 shows an example block diagram of the path-based algorithm module in accordance with aspects of this disclosure.

FIG. 10 shows an example block diagram of the path-based algorithm module 975 in accordance with aspects of this disclosure. The path-based algorithm module 975 receives as input, estimated state data (prior) (e.g., position data and/or depth data) from the estimated state data store 985, the 3D model data from the 3D model data store 940, and the path data from the path data store 945. Based on the received data, the path-based algorithm module 975 determines an estimate of the position of the instrument tip relative to the 3D model of the tubular network and provides path-based estimated state data (current) to the state estimator 980, which can be stored in the estimated state data store 985. As an example, the path-based estimated state data may be represented as a probability distribution between a plurality of identified segments of the 3D model (e.g., a discrete distribution of 30% and 70% for two segments joined at a bifurcation).

The navigation configuration system 900 may operate in one of a plurality of modalities depending on the current location of the instrument tip, which may be defined based on the estimated state data (prior) received from the estimated state data store 985. Specifically, the navigation configuration system 900 may operate in one modality (e.g., using navigation module 905) when the current location of the instrument tip is determined to be within a mapped portion of the luminal network, which may be defined by the 3D model data stored in the 3D model data store 940. Further, in certain implementations, the path-based algorithm module 975 may operate in another modality (e.g., using outside segmentation navigation module 907) when the current location of the instrument tip is determined to be outside of the mapped portion of the luminal network or within a threshold distance of the unmapped portion of the luminal network. As will be described in greater detail below, the navigation configuration system 900 may transition between the first and second modalities based on the detection of certain threshold values, such as, the distance from the current location of the instrument to the edge of the mapped portion of the luminal network.

VI. B. 2. I. Path-Based Navigation—within Mapped Portion of Luminal Network

Figure 11:
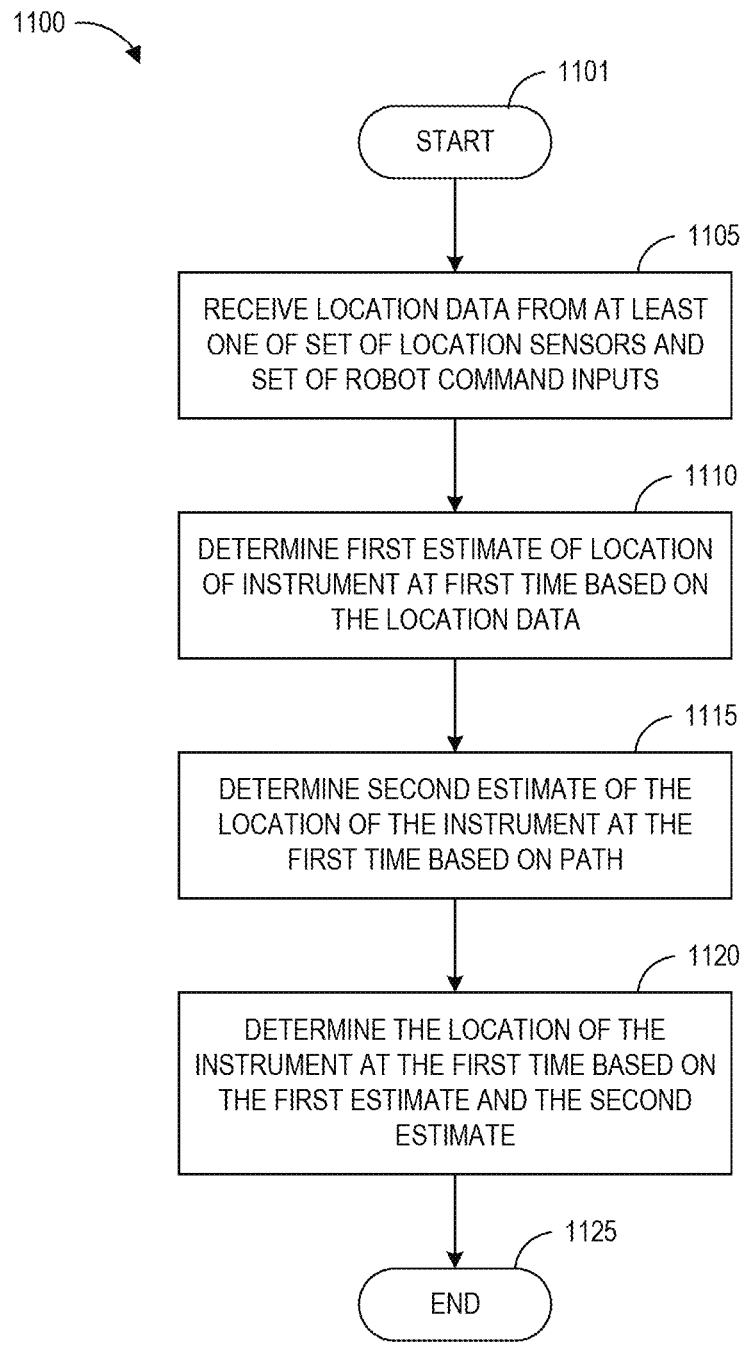
FIG. 11 is a flowchart illustrating an example method operable by a robotic system, or component(s) thereof, for path-based navigation of tubular networks in accordance with aspects of this disclosure.

FIG. 11 is a flowchart illustrating an example method operable by a robotic system, or component(s) thereof, for path-based navigation of tubular networks in accordance with aspects of this disclosure. For example, the steps of method 1100 illustrated in FIG. 11 may be performed by processor(s) and/or other component(s) of a medical robotic system (e.g., surgical robotic system 500) or associated system(s) (e.g., the path-based algorithm module 945 of the navigation configuration system 900). For convenience, the method 1100 is described as performed by the navigation configuration system, also referred to simply as the "system" in connection with the description of the method 1100.

The method 1100 begins at block 1101. At block 1105, the system may receive location data from at least one of a set of location sensors and a set of robot command inputs. The location data may be indicative of a location of an instrument configured to be driven through a luminal network of a patient. As described above, the system may include at least one computer-readable memory having stored thereon a model of the luminal network (e.g., the 3D model data stored in 3D model data store 940), a position of a target with respect to the model, and a path along at least a portion of the model from an access point to the target. In certain embodiments, the path and the position of the target may be stored as path data in the path data store 945.

At block 1110, the system may determine a first estimate of the location of the instrument at a first time based on the location data. The first estimate of the location of the instrument may be based on, for example, data received from one or more of the image data store 910, the EM data store 920, the robot data store 930, and/or the 3D model data store 940.

At block 1115, the system may determine a second estimate of the location of the instrument at the first time based on the path. In certain implementations, the path-based estimated state data may include an indication of a segment along the path (e.g., path data received from the path data store 945) and a weight associated with the identified segment. Thus, the system may determine a weight associated with the path-based location estimate.

Depending on the embodiment, the system may select a segment of the luminal network along the path as the estimated location of the instrument based on depth data received from the depth data store 1088 of the estimated state data store 985. The system may, using the depth information, estimate the location of the instrument based on a distance along the path determined from the depth data (e.g., a distance defined by the depth data starting from the access point of the luminal network).

The system may employ one of a plurality of methods or modalities to determine the weight associated with the path-based estimate. In certain embodiments, the system may determine the weight based on the location of the instrument within the luminal network (e.g., based on the estimated state data (prior) received from the estimated state data store 985). As described in detail below, the weight associated with the path-based location estimate may be based on the probability that the operator will deviate from the path while driving the instrument. Various factors may influence the probability that the operator will drive the instrument down a segment of the luminal network that is not part of the path. Examples of these factors include: difficulty in visually identifying the correct segment for advancing the instrument, complexity of the branching system of the luminal network, operator determination to explore portions of the luminal network outside of the path, etc. Some or all of these factors may increase the probability that the operator will deviate from the path according to the insertion depth of the instrument into the luminal network. By proper selection of the weight, the system may increase the ability of the state estimator 980 to reliably use the path-based location estimation as a source of data on which to base the estimated state of the instrument.

In related aspects, further details and an example model relating to block 1115 are described below with reference to FIG. 12.

Continuing with FIG. 11, at block 1120, the system may determine the location of the instrument at the first time based on the first estimate and the second estimate. This determination may be performed, for example, by the state estimator 980 determining the state of the instrument based on estimated state data received from the path-based algorithm module 975 and at least one: of the EM-based algorithm module 950, the image-based algorithm module 960, and the robot-based algorithm module 970. In embodiments where the system determines a weight associated with the path-based location estimate, the system may further use the weight in determining the location of the instrument at block 1120. The method 1110 ends at block 1125.

Figure 12:
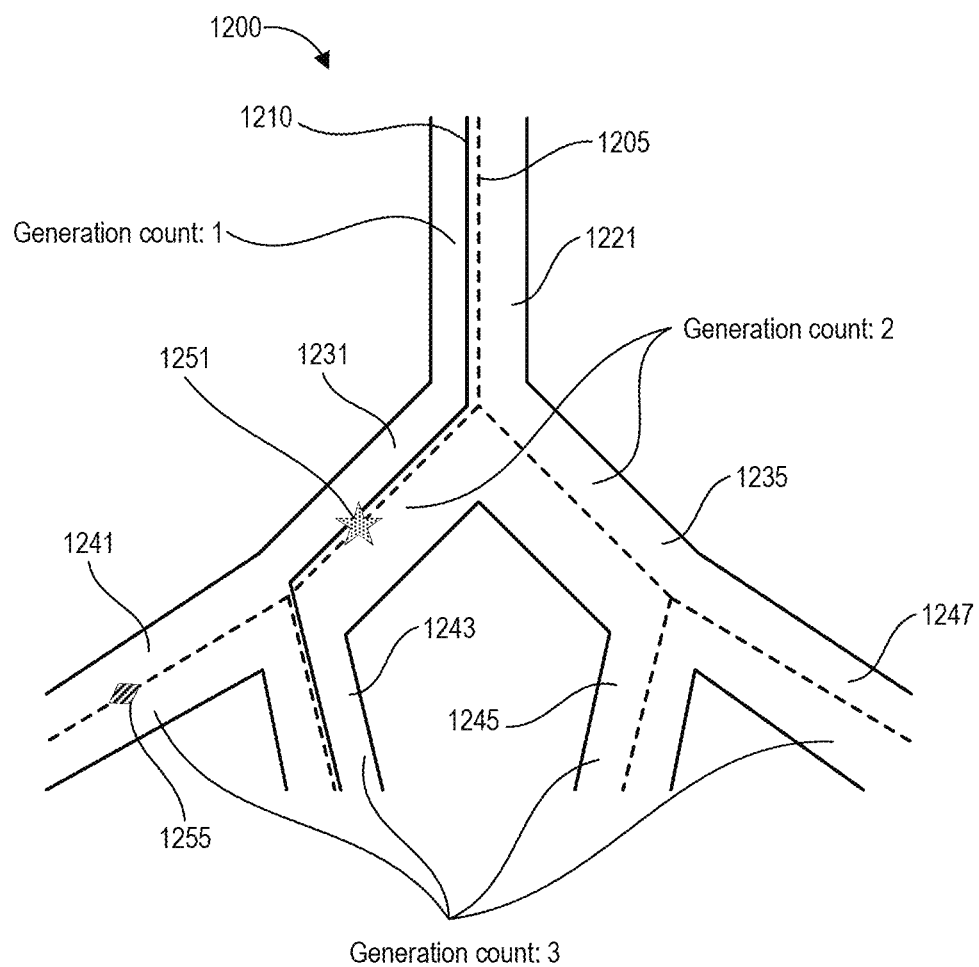
FIG. 12 is a simplified example model of a portion of a luminal network for describing aspects of this disclosure related to path-based location estimation.

FIG. 12 is a simplified example model of a portion of a luminal network for describing aspects of this disclosure related to path-based location estimation. In particular, FIG. 12 depicts a model 1200 of a simplified luminal network including a skeleton 1205, which may be defined by a centerline of the luminal network, and a navigational path 1210 which traverses a portion of the model 1200. Although illustrated as offset from the skeleton 1205, the navigational path 1210 may be defined along the skeleton 1205 in certain embodiments. The model 1200 further includes a first-generation segment 1221, two second-generation segments 1231 and 1235 which branch from the first-generation segment 1221, and four third-generation segments 1241, 1243, 1245, and 1247. Two example locations 1251 and 1255 of a distal end of an instrument are also illustrated in FIG. 12.

In one implementation, the location of the instrument may be defined by identifying the segment in which the distal end of the instrument is currently located. In this implementation, the model may include a plurality of segments (e.g., segments 1221-1247 as illustrated in FIG. 12), where each segment is associated with a generation count or generation designation. The generation count of a given segment may be determined or defined based on the number of branches in the luminal network located between the given segment and an access point of the patient allowing the instrument access into the luminal network. In the FIG. 12 embodiment, an example assignment of generation counts to the segments 1221-1247 may include: the first generation segment 1221 having a generation count of one, the second generation segments 1231 and 1235 having a generation count of two, and the third generation segments 1241, 1243, 1245, and 1247 having a generation count of three. Those skilled in the art will recognize that other numbering schemes may be employed to assign generation counts and/or generation designations to the segments of a luminal network.

In certain implementations, the system may estimate a current segment in which the instrument is located using a path-based location estimate and determine the weight associated with the path-based location estimate based on the generation count of the current segment. For example, when the instrument is positioned at the first location 1251, the segment count of the current segment 1231 may be two. The system may, in certain embodiments, decrease the weight for the path-based location estimate as the generation count increases. In other words, the weight given to the path-based estimate may be decreased (e.g., monotonically) as the generation count of the current segment increases. Referring to the example of FIG. 12, in this implementation the weight assigned to the path-based estimate at the second location 1255 may be less than the weight assigned to the path-based estimate at the first location 1251. The particular function used by the system to determine the weight is not particularly limited. In one example implementation, the weight given to a particular segment may be inversely proportional to the segment's generation count.

After the instrument has been advanced a sufficient distance into the luminal network, the system may reduce the weight assigned to the path-based location estimate to zero or another minimal value. In certain implementations, the system may determine whether to reduce the weight to zero or the minimal value based on the generation count of the current segment in which the instrument is located. For example, the system may determine that the generation count of the current segment is greater than a threshold generation count, and set the weight to zero, or the minimal value, in response to determining that the generation count of the first segment is greater than the threshold generation count.

Depending on the embodiment, the weight associated with the path-based location estimate may correspond to a confidence value associated with the estimate. As described above, the confidence value may reflect a measure of confidence in the estimation of the state provided by the path-based algorithm module 975. The system may determine the confidence value based on the likelihood that the operator of the robotic system will deviate from the navigation path. The likelihood that the operator will deviate from the navigation path may be determined empirically based on tracking the location of the instrument during actual medical procedures. In one example, the likelihood that the operator will deviate from the navigation path near the start of the procedure may be practically zero, such as when the operator is transitioning from the trachea to one of the main bronchi during a bronchoscopic procedure. However, as the instrument is advanced further into the airway, it may be more difficult for the operator to identify the correct segment of the network to drive the instrument into based on, for example, the images received from the camera. Alternatively, the operator may decide to deviate from the path when as the instrument approaches the target in order to investigate a portion of the luminal network or to perform a complex navigational maneuver (e.g., articulating the instrument around a tight curvature in the luminal network). Thus, it may be advantageous to lower the confidence level of the path-based location estimate to match the increasing probability that the operator will leave the navigation path as the instrument advances further into the luminal network.

Figure 13:
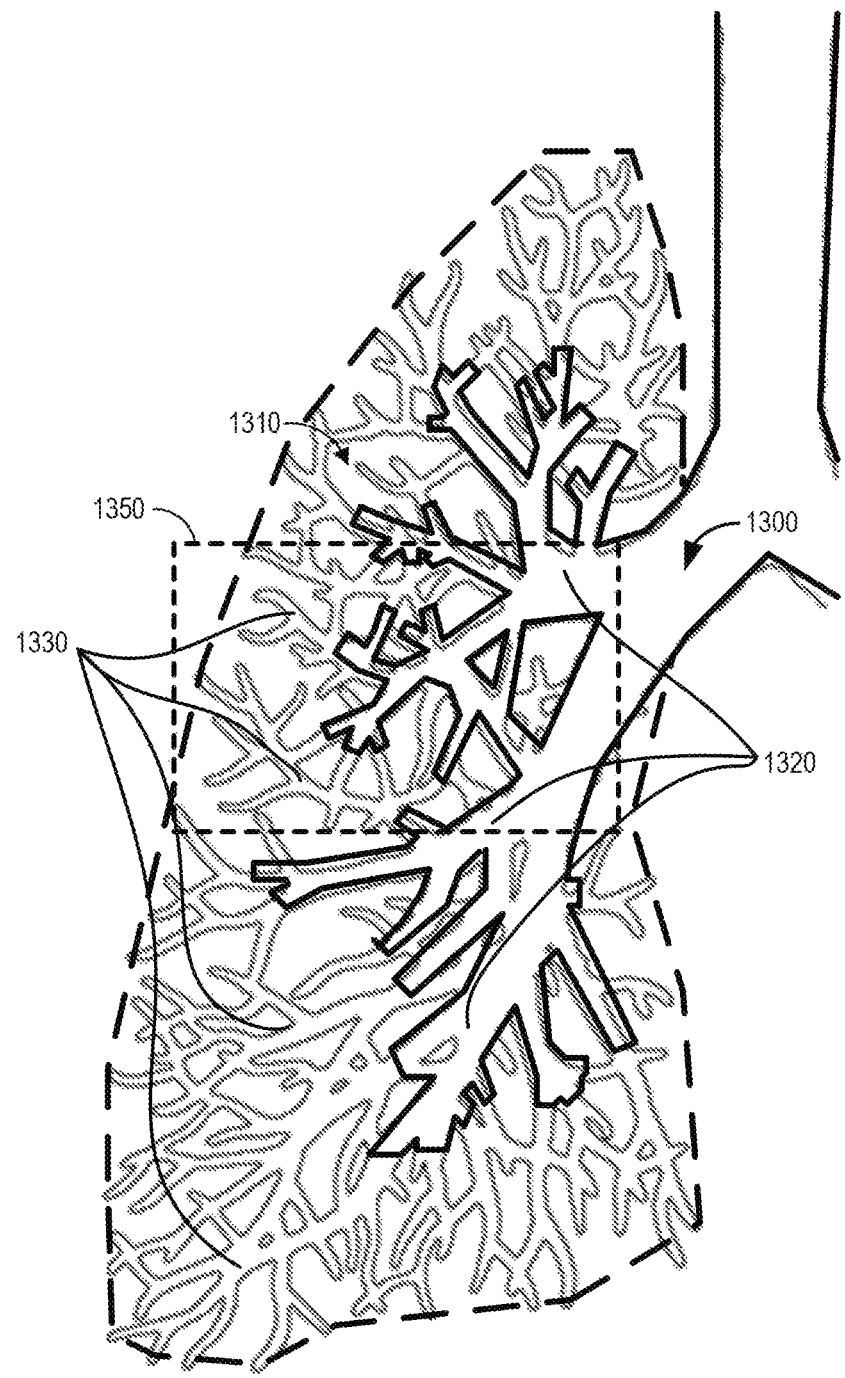
FIG. 13 is an example view of a model overlaid on a luminal network in accordance with aspects of this disclosure.

VI. B. 2. II. Path-Based Navigation—Outside of Mapped Portion of Luminal Network In addition to the use of the path in estimating the location of the instrument when within the mapped portion of the luminal network, the path may also be used as a data source in when the instrument is located outside of the mapped portion of the luminal network. In particular, the model of a given luminal network may not fully map the entirety of the luminal network. FIG. 13 is an example view of a model 1300 (e.g., 3D model data stored in the 3D model data store 940) overlaid on a luminal network 1310 in accordance with aspects of this disclosure. In some instances, limitations in the imaging and mapping techniques used to generate the model 1300 may prevent generation of a model that corresponds to the entire luminal network 1310. For example, certain branched lumens within the luminal network may be sufficiently small that they cannot be clearly depicted and analyzed with common imaging and mapping techniques. As such, the model 1300 may not provide a complete representation of the luminal network 1310, for example, leaving various portions of the luminal network 1310 unmapped and/or unrepresented in the model 1300.

For example, as shown in FIG. 13, the model 1300 can correspond to a mapped portion 1320 of the luminal network 1310. An unmapped portion 1330 of the luminal network 1310, which may not be represented by the model 1300, may extend beyond the mapped portion 1320. A portion 1350 of the model 1300 including a section of the mapped portion 1320 of the luminal network 1310 and a section of the unmapped portion 1330 of the luminal network 1310 is enlarged in FIG. 15, which is described below.

Certain algorithms for estimating the location of the instrument may utilize the 3D model data received from the 3D model data store in order to generate estimated state data representative of the location of the instrument. For example, each of the EM-based algorithm module 950, the image-based algorithm module 960, and the robot-based algorithm module 970 may use 3D model data received from the 3D model data store 940 in estimating the state data. Accordingly, if the instrument is driven to an unmapped portion (e.g., unmapped portion 1330 of FIG. 13) of a luminal network, the 3D model data store 940 may not have 3D model data which can be used in the estimation of the location of the instrument. Thus, aspects of this disclosure relate to the use of the path data (e.g., stored in the path data store 945) to address the lack of 3D model data used to estimate the instrument location.

Figure 14:
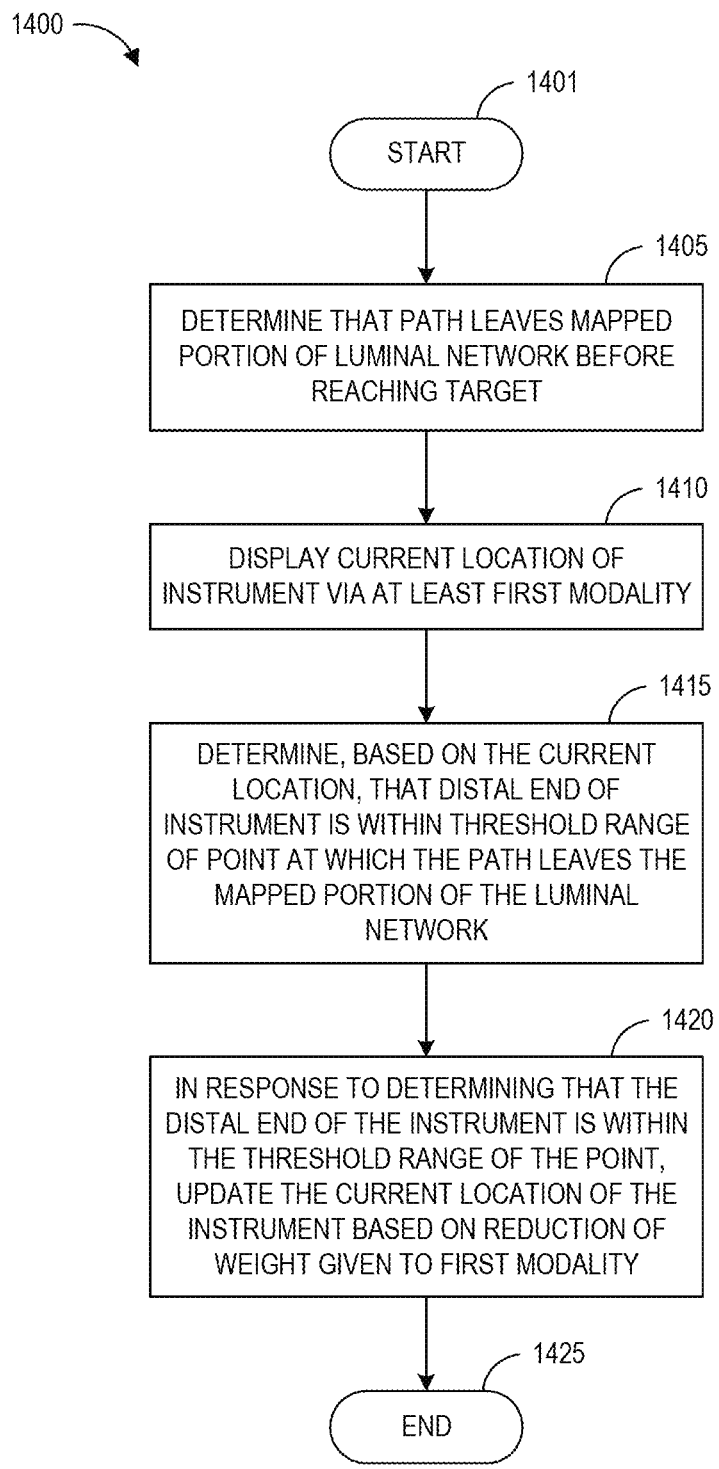
FIG. 14 is a flowchart illustrating another example method operable by a robotic system, or component(s) thereof, for path-based navigation of tubular networks in accordance with aspects of this disclosure.

FIG. 14 is a flowchart illustrating another example method operable by a robotic system, or component(s) thereof, for using path-based data in navigation outside of unsegmented portions of tubular networks in accordance with aspects of this disclosure. For example, the steps of method 1400 illustrated in FIG. 14 may be performed by processor(s) and/or other component(s) of a medical robotic system (e.g., surgical robotic system 500) or associated system(s) (e.g., the path-based algorithm module 945 of the navigation configuration system 900). For convenience, the method 1400 is described as performed by the navigation configuration system 900, also referred to simply as the "system" in connection with the description of the method 1400.

The method 1400 begins at block 1401. At block 1405, the system may determine that the path leaves a mapped portion of a luminal network of a patient before reaching a target. In performing the method 1400, the system may include at least one computer-readable memory having stored thereon a model of the mapped portion of the luminal, a position of the target with respect to the model, and the path along at least a portion of the model from an access point to the target. Thus, block 1405 may involve the processor determining that at least a portion of the path extends through an unmapped portion of the luminal network to the target.

In related aspects, further details relating to block 1405 are described below with reference to FIG. 15. In particular, the description below in connection with FIG. 15 provides further detail regarding a number of embodiments detailing how the system may determine that the path has left the mapped portion of the luminal network.

At block 1410, the system may display a current location of an instrument via at least a first modality (e.g., the navigation module 905 of FIG. 9A). The first modality may include the system deriving a location of the instrument based on location data received from a set of one or more location sensors and the mapped portion of the model. Examples of the location data include image data, EM data, and robot data. Depending on the embodiment, the first modality may include an estimate of the location of the instrument via one or more of the EM-based algorithm module 950, the image-based algorithm module 960, and the robot-based algorithm module 970.

At block 1415, the system may determine, based on the current location of the instrument, that the distal end of the instrument is within a threshold range of a point at which the path leaves the mapped portion of the luminal network.

Figure 15:
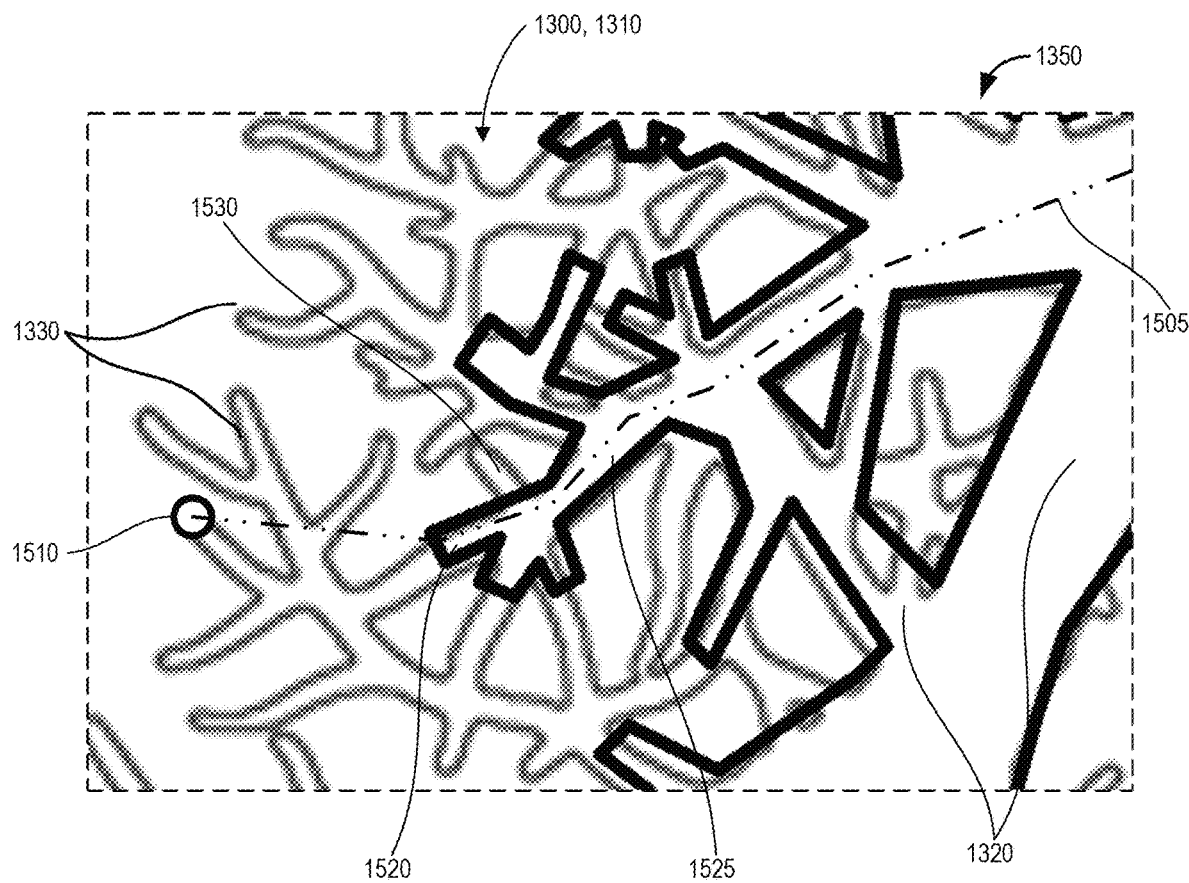
FIG. 15 illustrates a portion of the luminal network of FIG. 13 including a mapped portion and an unmapped portion in accordance with aspects of this disclosure.

In one embodiment, the system may determine that the instrument is within a threshold range of a point at which the path leaves the mapped portion of the luminal network based on determining that the instrument is located within the second to last segment 1525 as illustrated in the example of FIG. 15. The system may identify the second to last segment 1525 as a segment of the model 1300 which is adjacent to the last segment 1520 and located along the path 1505.

In another embodiment, the system may determine that the distal end of the instrument is within a threshold range of a point at which the path leaves the mapped portion of the luminal network based on identifying the location(s) of one of more unmapped intersections between the last segment 1520 and one or more unmapped segments 1530 of the luminal network 1310. In one implementation, the system may use images captured using a camera located at or near the distal end of the instrument. The system may be configured to identify visual objects within the image that are representative of an intersection (e.g., a bifurcation) in the luminal network 1310. The system may use the detected visual objects to estimate the location of the intersection between the last segment 1520 and the unmapped segment(s) 1530.

The system may also determine the distal end of the instrument is within a threshold range of a point at which the path leaves the mapped portion of the luminal network based on the distance between the current location of the instrument and the location of the intersection. In certain embodiments, the system may determine that the current location of the instrument is within a defined distance from the location of the one of more unmapped intersections.

At block 1420, the system may, in response to determining that that the distal end of the instrument is within the threshold range of the point, update the current location of the instrument based on a reduction of a weight given to the first modality. In addition to or in place of reducing the weight given to the first modality based on the threshold range, the system may also use one or more other conditions for reducing the weight given to the first modality. For example, one such condition may include determining that the instrument is located within the second to last segment (e.g., the second to last segment 1525 of FIG. 15). Another condition may include determining that the instrument is within a threshold distance from the second to last segment 1525. In another aspect, the condition may include determining that the current location of the instrument is within a defined distance from the location of one or more unmapped intersections present in the last segment 1520.

The system may also be configured to increase the weight given to the first modality in response to the instrument returning to the mapped portion of the luminal network. This increase in the weight given to the first modality may include returning the weight to the original value prior to reducing the weight in block 1420.

In certain implementations, the system may determine, based on the current location of the instrument, that the distal end of the instrument has returned to the mapped portion of the luminal network from outside of the mapped portion of the luminal network (e.g., from the unmapped portion of the luminal network). In response to determining that the distal end of the instrument has returned to the mapped portion of the luminal network, the system may update the current location of the instrument based on an increase in the weight given to the first modality. That is, the system may return to the use of the 3D model data from the 3D model data store 940 in one or more of the EM-based algorithm module 950, the image-based algorithm module 960, and the robot-based algorithm module 970.

The determination that the instrument has returned to the mapped portion of the luminal network may also involve the system storing an indication of the location at which the instrument left the mapped portion of the luminal network. For example, the system may determine a location of the instrument at which the estimation of location of the instrument was first based on the reduced weight given to the first modality. In response to determining that the instrument is retracted to the above-mentioned location, the system may then determine that the instrument has been retracted to within the mapped portion of the luminal network.

In some implementations, the reduction of the weight given to the first modality may include entering a path tracing mode. The path tracing mode may include, for example, the system displaying, on a user display, visual indicia indicative of previous locations of the instrument with respect to the model. The path tracing mode may also be referred to as a "breadcrumb" mode where new visual indicia are displayed on the user display at regular intervals. In certain implementations, the visual indicia may be indicative of historical positions of the instrument within the luminal network, and particularly, within the unmapped portion of the luminal network. Depending on the embodiment, the system may determine the location of the instrument without reference to at least one of the image data, the EM data, and the robot data when in the path tracing mode. Certain embodiments which may be used to calculate and apply an offset to EM data are described in U.S. Application No. 62/572,285, filed on Oct. 13, 2017, and U.S. patent application Ser. No. 16/143,362, now U.S. Pat. No. 11,058,493, filed on Sep. 26, 2018, each of which is incorporated herein by reference in its entirety.

In other implementations, the reduction of the weight given to the first modality may include entering a second modality for determining the location of the distal end of the instrument. Referring back to FIG. 9A, in the second modality the system 900 may determine the output navigation data provided to the output navigation data store 990 using the outside segmentation navigation module 907 in place of the navigation module 905. The outside segmentation navigation module 907 may locate (or determine) the estimated state of the medical instrument within a tubular network base on input data received from at least one of the EM data store 920, the robot data store 930, the 3D model data store 940, and the path data store 945. As described above, the system 900 may determine to enter the second modality based on path data received from the path data store 945.

The system may determine the location of the instrument in the second modality via, for example, deriving the location of the instrument based on location data (e.g., EM data, and robot data) independent of the mapped portion of the model (e.g., 3D model data). In particular, the outside segmentation navigation module 907 may use data received from each of the EM data store 920, the robot data store 930, and the 3D model data store 940 to determine a registration for the EM data. Additionally, outside segmentation navigation module 907 may use the robot data to track the amount of insertion and/or retraction of the instrument. The outside segmentation navigation module 907 may use insertion and/or retraction data to determine whether the instrument has been retracted to the point at which the second modality was entered and switch back to the first modality based on the instrument being retracted to this point.

The outside segmentation navigation module 907 may also use the 3D model data to apply an offset to the registered EM data when transitioning from the use of the navigation module 905 to the outside segmentation navigation module 907. The offset may prevent a sudden jump in the output navigation data which may otherwise occur during the transition. Certain embodiments which may be used to calculate and apply an offset to EM data are described in U.S. Application No. 62/607,246, filed on Dec. 18, 2017, and U.S. patent application Ser. No. 16/221,020, now U.S. Pat. No. 11,160,615, filed on Dec. 14, 2018, each of which is incorporated herein by reference in its entirety. In certain implementations, the outside segmentation navigation module 907 may produce output navigation data using registered EM data. Thus, the outside segmentation navigation module 907 may first determine the registration for the EM data prior to determining the output navigation data. In some implementations, the system 900 may determine the registration based on the instrument being driven a predetermined distance into the luminal network (e.g., into a third-generation segment). Thus, the outside segmentation navigation module 907 may begin producing the output navigation data in response to the instrument being driven into a third-generation segment (e.g., the third generation segments 1241, 1243, 1245, and 1247 of FIG. 12). The method 1400 ends at block 1425.

A number of example embodiments which may be used to determine whether the path leaves the mapped portion of the luminal network will be discussed in connection with FIG. 15. FIG. 15 illustrates a portion 1350 of the luminal network 1310 of FIG. 13 including a mapped portion 1320 and an unmapped portion 1330 in accordance with aspects of this disclosure. As shown in the example of FIG. 15, a target 1510 may be located within the unmapped portion 1330 of the luminal network 1310. Accordingly, a path 1505 may extend from the mapped portion 1320 of the luminal network 1310 into the unmapped portion 1330 of the luminal network 1310 before reaching the target 1510. Since the unmapped portion 1330 of the luminal network 1310 may not be available for the operator to view when selecting the path 1505 (e.g., during pre-operative path planning as discussed in connection with FIG. 17 below), the path 1505 may not necessarily follow the lumens in the unmapped portion 1330 of the luminal network 1310. In some embodiments, the path 1505 may follow a substantially straight line between a final segment 1520 of the path 1505 and the target 1510.

As shown in FIG. 15, the model 1300 includes a plurality of segments, including a first segment 1520 and a second segment 1525. The first segment 1520 may represent the final segment 1520 of the model 1300 before the path 1505 leaves the mapped portion 1320 of the luminal network 1310 while the second segment 1525 may represent the second to last (also referred to as the "penultimate") segment 1525 of the model 1300 before the path 1505 leaves the mapped portion 1320 of the luminal network 1310. The system may determine that the path leaves the mapped portion 1320 of the luminal network, for example at block 1405 illustrated in FIG. 14, based on the identification of the final segment 1520 and/or the second to last segment 1525.

In certain embodiments, the system may determine a point at which the path 1505 leaves the mapped portion 1320 of the luminal network 1310 based on an identification of the last and/or second to last segments 1520 and/or 1525. Thus, the system may determine that the path 1505 leaves the mapped portion 1320 of the luminal network 1310 before reaching the target 1510 based on a determination that the path 1505 leaves the mapped portion 1320 of the luminal network 1310 from the last segment 1520 of the model 1300.

In another embodiment, the system may determine that the instrument leaves the mapped portion 1320 of the luminal network 1310 before reaching the target 1510 based on a determination that the instrument is within a threshold distance from the second segment 1525. Thus, the system may determine the distance between the current location of the instrument and the point at which the path leaves the mapped portion 1320 of the luminal network 1310 and compare the distance to the threshold distance. In one embodiment, the system may determine the distance between the current location of the instrument and the point at which the path 1505 leaves the mapped portion 1320 of the luminal network 1310 as the length of the path 1505 between current location of the instrument and the point at which the path 1505 leaves the mapped portion 1320 of the luminal network 1310. In other embodiment, the system may determine the Euclidean distance between current location of the instrument and the point at which the path 1505 leaves the mapped portion 1320 of the luminal network 1310.

Figure 16:
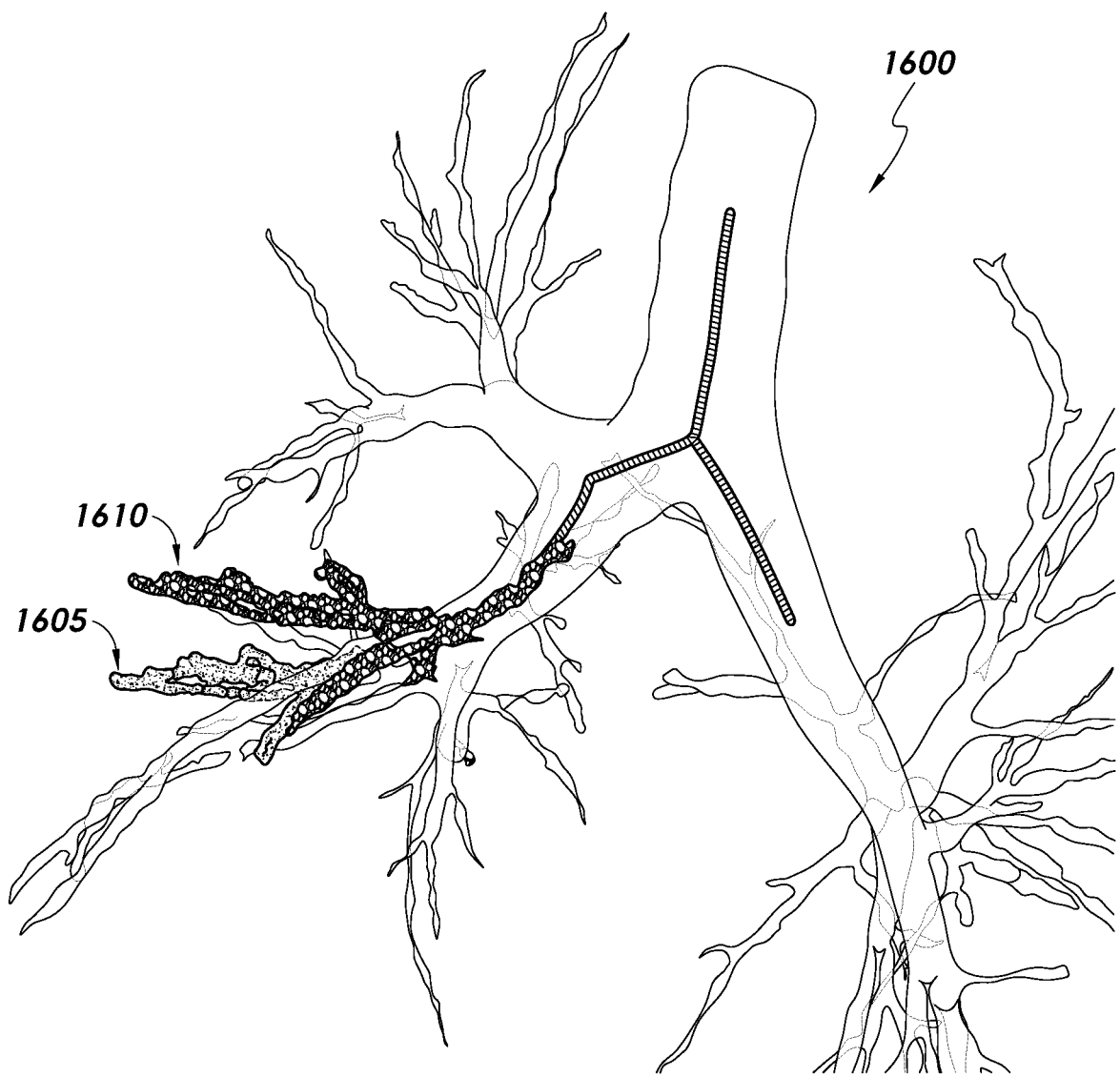
FIG. 16 is a view of a 3D model including tracked locations of a distal end of an instrument in accordance with aspects of this disclosure.

FIG. 16 is a view of a 3D model including tracked locations of a distal end of an instrument in accordance with aspects of this disclosure. In the example of FIG. 16, the view includes a 3D model of a luminal network 1600, a first set of tracked estimated locations 1605 of the instrument and a second set of tracked estimated locations 1610 of the instrument. The mapped and unmapped portions of the luminal network 1600 are not illustrated in FIG. 16.

The first set of tracked estimated locations 1605 represent the estimated location of the distal end of the instrument as estimated by the first modality as described in connection with FIG. 14 above, without any change to the weight given to the first modality. In contrast, the second set of tracked estimated locations 1610 represent the estimated location of the distal end of the instrument as estimated by the first modality as described in connection with FIG. 14 above, including the reduction to the weight given to the first modality performed in block 1420.

In the example of FIG. 16, the instrument was driven outside of a mapped portion of the luminal network 1600. Since the first modality was used without change to the weight given thereto, the first set of tracked estimated locations 1605 continued to use the preoperative 3D model data from the 3D model data store 940 even after the instrument left the mapped portion of the luminal network 1600. Accordingly, the first set of tracked estimated locations 1605 are not closely matched to the location of the unmapped portion of the luminal network 1600 and thus, provide an inaccurate estimate of the instrument location. The second set of tracked estimated locations 1610 illustrate an embodiment where the weight given to the first modality is reduced and may include entering a path tracing mode when the instrument is located in the second to last segment of the mapped portion of the model. Here, the second set of tracked estimated locations 1610 more closely track the actual locations of the luminal network 1600 than the first set of tracked estimated locations 1605 due to the switch from the first modality to the second modality.

VII. Pre-Operative Path Planning for Navigation Preparation

Figure 17:
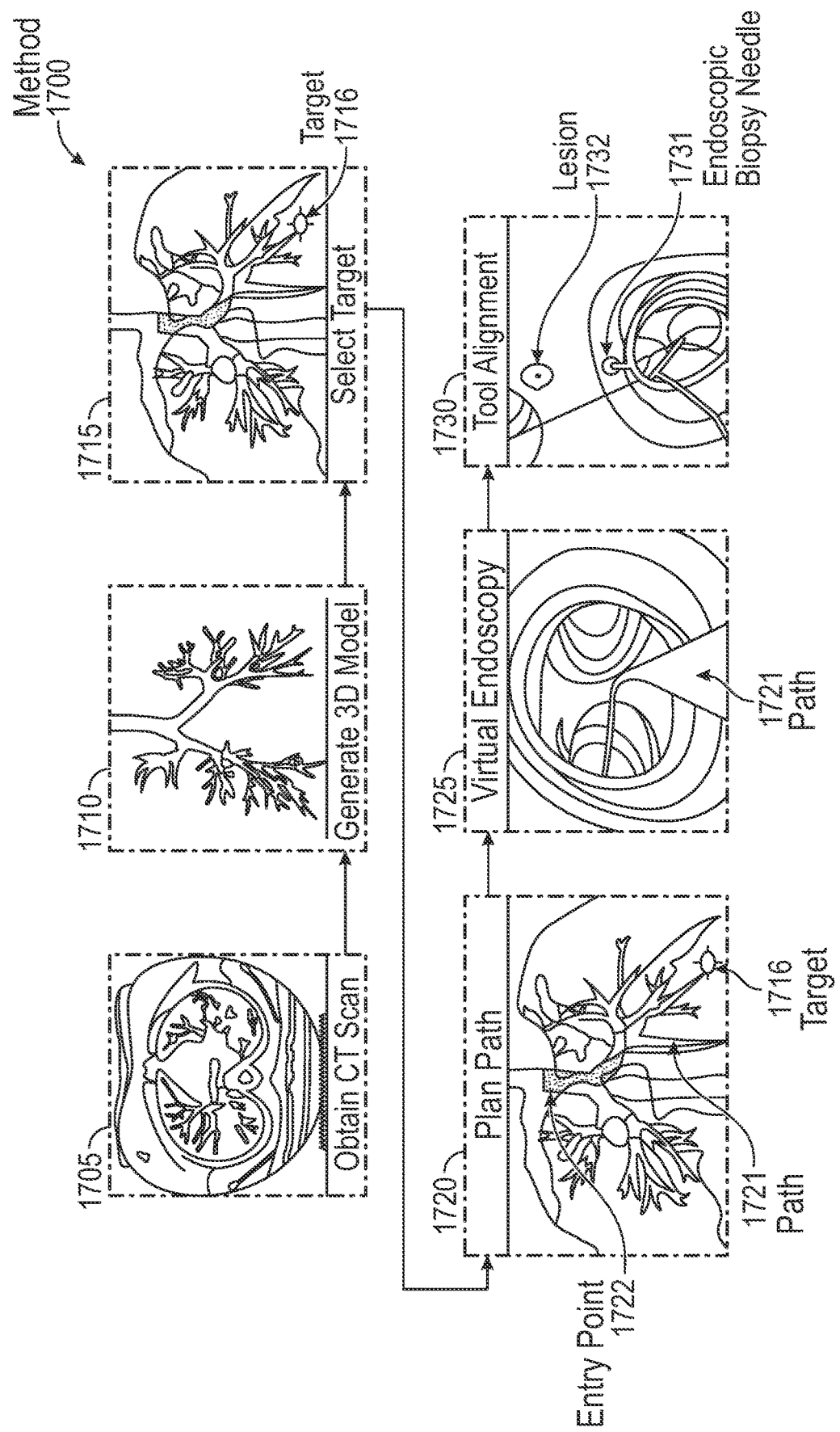
FIG. 17 show an example pre-operative method for preparation of a surgical instrument (e.g., an instrument tip) to navigate through an example tubular network, according to various embodiments.

Navigating to a particular point in a tubular network of a patient's body may involve taking certain steps pre-operatively to generate the information used to create the 3D model of the tubular network and to determine a navigation path. FIG. 17 shows an example pre-operative method for preparation of a surgical instrument (e.g., an instrument tip) to navigate through an example tubular network, according to various embodiments. In particular, FIG. 17 shows an example pre-operative method 1700 for navigating the instrument tip to a particular site within the tubular network. Alongside each step of the method 1700, a corresponding image is shown to illustrate a representation of the involved data for planning a path and navigating through the tubular network.

Initially, at block 1705, a scan/image generated based on preoperative model data (e.g., CT scan) of the tubular network is obtained, and the data from the CT scan provides 3D information about the structure and connectivity of the tubular network. For example, the image at block 1705 shows a tomographic slice of a patient's lungs.

At block 1710, a 3D model is generated based on the obtained CT scan data, and the generated 3D model can be used to assign each branch of the tubular network with a unique identity, enabling convenient navigation within the network. For example, the image at block 1710 shows a 3D model of a patient's bronchial network.

At block 1715, a target 1716 is selected, and this target may be, for example, a lesion to biopsy, or a portion of organ tissue to repair surgically. In one embodiment, the system provides a user capability for selecting the location of the target by interfacing with a computer display that can show the 3D model, such as by clicking with a mouse or touching a touchscreen. The selected target may then be displayed to the user. For example, the target 1716 is marked within the 3D bronchial model generated from step 1710.

At block 1720, a path 1721 is automatically planned from an entry point 1722 to the target 1716, and the path 1721 identifies a sequence of branches within the network to travel through, so as to reach the target 1716. In one embodiment, the tubular network may be tree-like, the path 1721 may be uniquely determined by the structure of the tubular network, while in another embodiment, the tubular network may be cyclic, and the path may be found by an appropriate algorithm such as a shortest-path algorithm.

Once the path 1721 has been determined, virtual endoscopy 1725 may be performed to give the user a preview of the endoscopic procedure. The 3D model generated from step 1710 is used to generate a sequence of 2D images as though seen by an endoscope tip while navigating the network corresponding to the 3D model. The path 1721 may be shown as a curve that may be followed to get from the entry point 1722 to the target 1716.

Once the virtual endoscope tip has arrived at the target 1716, a virtual tool alignment procedure 1730 may be performed to illustrate to the user how to manipulate endoscopic tools in order to perform a surgical procedure at the target. For example, in the illustration, a virtual endoscopic biopsy needle 1731 is maneuvered by the user in order to biopsy a lesion 1732 located beneath the surface of a bronchial tube. The lesion location is highlighted so that the user can align the needle to it, and then use the needle to pierce the surface of the bronchial tube and access the lesion underneath. This mimics the steps that will be taken during the actual surgical procedure, allowing the user to practice before performing surgery.

VIII. Implementing Systems and Terminology

Implementations disclosed herein provide systems, methods and apparatuses for path-based navigation of tubular networks.

It should be noted that the terms "couple," "coupling," "coupled" or other variations of the word couple as used herein may indicate either an indirect connection or a direct connection. For example, if a first component is "coupled" to a second component, the first component may be either indirectly connected to the second component via another component or directly connected to the second component.

The path-based navigational functions described herein may be stored as one or more instructions on a processor-readable or computer-readable medium. The term "computer-readable medium" refers to any available medium that can be accessed by a computer or processor. By way of example, and not limitation, such a medium may comprise random access memory (RAM), read-only memory (ROM), electrically erasable programmable read-only memory (EEPROM), flash memory, compact disc read-only memory (CD-ROM) or other optical disk storage may comprise RAM, ROM, EEPROM, flash memory, CD-ROM or other optical disk storage, magnetic disk storage or other magnetic storage devices, or any other medium that can be used to store desired program code in the form of instructions or data structures and that can be accessed by a computer. It should be noted that a computer-readable medium may be tangible and non-transitory. As used herein, the term "code" may refer to software, instructions, code or data that is/are executable by a computing device or processor.

The methods disclosed herein comprise one or more steps or actions for achieving the described method. The method steps and/or actions may be interchanged with one another without departing from the scope of the claims. In other words, unless a specific order of steps or actions is required for proper operation of the method that is being described, the order and/or use of specific steps and/or actions may be modified without departing from the scope of the claims.

As used herein, the term "plurality" denotes two or more. For example, a plurality of components indicates two or more components. The term "determining" encompasses a wide variety of actions and, therefore, "determining" can include calculating, computing, processing, deriving, investigating, looking up (e.g., looking up in a table, a database or another data structure), ascertaining and the like. Also, "determining" can include receiving (e.g., receiving information), accessing (e.g., accessing data in a memory) and the like. Also, "determining" can include resolving, selecting, choosing, establishing and the like.

The phrase "based on" does not mean "based only on," unless expressly specified otherwise. In other words, the phrase "based on" describes both "based only on" and "based at least on."

The previous description of the disclosed implementations is provided to enable any person skilled in the art to make or use the present invention. Various modifications to these implementations will be readily apparent to those skilled in the art, and the generic principles defined herein may be applied to other implementations without departing from the scope of the invention. For example, it will be appreciated that one of ordinary skill in the art will be able to employ a number corresponding alternative and equivalent structural details, such as equivalent ways of fastening, mounting, coupling, or engaging tool components, equivalent mechanisms for producing particular actuation motions, and equivalent mechanisms for delivering electrical energy. Thus, the present invention is not intended to be limited to the implementations shown herein but is to be accorded the widest scope consistent with the principles and novel features disclosed herein.

What is claimed is:

1. A medical robotic system, comprising:
an instrument configured to be driven through a luminal network; and
a control circuit having stored thereon a model of a mapped portion of the luminal network of a patient, a position of a target with respect to the model, and a path along at least a portion of the model from an access point to the target, the control circuit further having stored thereon computer-executable instructions to cause them to:
determine that the path leaves the mapped portion of the luminal network before reaching the target,
determine a current location of the instrument based on a weight given to at least a first modality, the first modality derives a location based on location data received from a set of one or more location sensors and the mapped portion of the model, the instrument is configured to be driven through the luminal network,
determine, based on the current location, that a distal end of the instrument is within a threshold range of a point at which the path leaves the mapped portion of the luminal network,
in response to determining that the distal end of the instrument is within the threshold range of the point at which the path leaves the mapped portion of the luminal network, update the current location of the instrument based on a reduction of the weight given to the first modality, and
command a robotic arm to move the instrument within the luminal network based on an updated location of the instrument.

2. The system of claim 1, wherein:
the model comprises a plurality of segments,
the determination that the path leaves the mapped portion of the luminal network before reaching the target comprises determining that the path leaves the mapped portion of the luminal network from a first segment of the model, and the control circuit has stored thereon computer-executable instructions to cause them to determine that the instrument is located within a second segment adjacent to the first segment and located along the path, and the updating of the current location of the instrument based on the reduction of weight given to the first modality is further in response to determining that the instrument is located within the second segment.

3. The system of claim 2, wherein:

the determination that the path leaves the mapped portion of the luminal network before reaching the target further comprises determining that the instrument is within a threshold distance from the second segment, and the updating of the current location of the instrument based on the reduction of weight given to the first modality is further in response to determining that the instrument is within the threshold distance from the second segment.

4. The system of claim 2, wherein the control circuit further has stored thereon computer-executable instructions to cause them to:

determine, based on the current location, that the distal end of the instrument has returned to the mapped portion of the luminal network from outside of the mapped portion of the luminal network, and in response to determining that the distal end of the instrument has returned to the mapped portion of the luminal network from outside of the mapped portion of the luminal network, update the current location of the instrument based on an increase in the weight given to the first modality.

5. The system of claim 4, wherein determining that the distal end of the instrument has returned to the mapped portion of the luminal network from outside of the mapped portion of the luminal network comprises:

determining a first location of the instrument at which the updating of the current location of the instrument was first based on the reduced weight given to the first modality, and determining that the instrument is retracted to the first location.

6. The system of claim 1, wherein:

the model comprises a plurality of segments, determining that the path leaves the mapped portion of the luminal network before reaching the target comprises determining that the path leaves the mapped portion of the luminal network from a first segment of the model, the control circuit further has stored thereon computer-executable instructions to cause them to:

identify a location of one or more unmapped intersections between the first segment and one or more unmapped segments the luminal network, and determine that the current location of the instrument is within a defined distance from the location of the one or more unmapped intersections, and updating the current location of the instrument based on the reduction of weight given to the first modality is further in response to determining that the current location of the instrument is within the defined distance from the location of the one or more unmapped intersections.

7. The system of claim 1, wherein the control circuit further has stored thereon computer-executable instructions to cause them to:

in response to determining that the current location of the instrument is within the threshold range of the point, enter a path tracing mode, and when in the path tracing mode, display, on a user display, visual indicia indicative of previous locations of the instrument with respect to the model.

8. The system of claim 7, wherein the visual indicia are indicative of historical positions of the instrument within the luminal network.

9. The system of claim 7, wherein:

the first modality derives the location of the instrument based on image data, electromagnetic (EM) data, and robot data when not in the path tracing mode.

10. The system of claim 9, wherein the control circuit further has stored thereon computer-executable instructions to cause them to:

determine the location of the instrument without reference to at least one of the image data, the EM data, and the robot data when in the path tracing mode.

11. The system of claim 1, wherein the control circuit further has stored thereon computer-executable instructions to cause them to:

in response to determining that that the distal end of the instrument is within the threshold range of the point, update the current location of the instrument via at least a second modality, wherein the second modality derives the location based on the location data and independent of the mapped portion of the model.

12. A non-transitory computer readable storage medium having stored thereon instructions that, when executed, cause at least one computing device to:

determine that a path leaves a mapped portion of a luminal network of a patient before reaching a target, at least one computer-readable memory having stored thereon a model of the mapped portion of the luminal network, a position of the target with respect to the model, and the path along at least a portion of the model from an access point to the target;

determine a current location of an instrument based on a weight given to at least a first modality, the first modality derives a location based on location data received from a set of one or more location sensors and the mapped portion of the model, the instrument is configured to be driven through the luminal network;

determine, based on the current location, that a distal end of the instrument is within a threshold range of a point at which the path leaves the mapped portion of the luminal network; and in response to determining that the distal end of the instrument is within the threshold range of the point at which the path leaves the mapped portion of the luminal network, update the current location of the instrument based on a reduction of the weight given to the first modality; and command a robotic arm to move the instrument within the luminal network based on the updated location of the instrument.

13. The non-transitory computer readable storage medium of claim 12, wherein:

the model comprises a plurality of segments, the determination that the path leaves the mapped portion of the luminal network before reaching the target comprises determining that the path leaves the mapped portion of the luminal network from a first segment of the model, and the non-transitory computer readable storage medium further has stored thereon instructions that, when executed, cause the at least one computing device to determine that the instrument is located within a second segment adjacent to the first segment and located along the path, and the updating of the current location of the instrument based on the reduction of weight given to the first modality is further in response to determining that the instrument is located within the second segment.

14. The non-transitory computer readable storage medium of claim 13, wherein:

the determination that the path leaves the mapped portion of the luminal network before reaching the target further comprises determining that the instrument is within a threshold distance from the second segment, and the updating of the current location of the instrument based on the reduction of weight given to the first modality is further in response to determining that the instrument is within the threshold distance from the second segment.

15. The non-transitory computer readable storage medium of claim 13, wherein the non-transitory computer readable storage medium further has stored thereon instructions that, when executed, cause the at least one computing device to:

determine, based on the current location, that the distal end of the instrument has returned to the mapped portion of the luminal network from outside of the mapped portion of the luminal network, and in response to determining that the distal end of the instrument has returned to the mapped portion of the luminal network from outside of the mapped portion of the luminal network, update the current location of the instrument based on an increase in the weight given to the first modality.

16. The non-transitory computer readable storage medium of claim 15, wherein determining that the distal end of the instrument has returned to the mapped portion of the luminal network from outside of the mapped portion of the luminal network comprises:

determining a first location of the instrument at which the updating of the current location of the instrument was first based on the reduced weight given to the first modality, and determining that the instrument is retracted to the first location.

17. The non-transitory computer readable storage medium of claim 13, wherein:

the model comprises a plurality of segments, determining that the path leaves the mapped portion of the luminal network before reaching the target comprises determining that the path leaves the mapped portion of the luminal network from a first segment of the model, the non-transitory computer readable storage medium further has stored thereon instructions that, when executed, cause the at least one computing device to:

identify a location of one or more unmapped intersections between the first segment and one or more unmapped segments the luminal network; and determine that the current location of the instrument is within a defined distance from the location of the one or more unmapped intersections, and updating the current location of the instrument based on the reduction of weight given to the first modality is further in response to determining that the current location of the instrument is within the defined distance from the location of the one or more unmapped intersections.

18. The non-transitory computer readable storage medium of claim 13, wherein the non-transitory computer readable storage medium further has stored thereon instructions that, when executed, cause the at least one computing device to:

in response to determining that the current location of the instrument is within the threshold range of the point, enter a path tracing mode, and when in the path tracing mode, display, on a user display, visual indicia indicative of previous locations of the instrument with respect to the model.

19. The non-transitory computer readable storage medium of claim 18, wherein the visual indicia are indicative of historical positions of the instrument within the luminal network.

20. The non-transitory computer readable storage medium of claim 18, wherein:

the first modality derives the location of the instrument based on image data, electromagnetic (EM) data, and robot data when not in the path tracing mode.

21. The non-transitory computer readable storage medium of claim 20, wherein the non-transitory computer readable storage medium further has stored thereon instructions that, when executed, cause the at least one computing device to:

determine the location of the instrument without reference to at least one of the image data, the EM data, and the robot data when in the path tracing mode.

22. The non-transitory computer readable storage medium of claim 12, wherein the non-transitory computer readable storage medium further has stored thereon instructions that, when executed, cause the at least one computing device to:

in response to determining that the distal end of the instrument is within the threshold range of the point, update the current location of the instrument via at least a second modality, wherein the second modality derives the location based on the location data and independent of the mapped portion of the model.

23. A method of determining a location of an instrument, comprising:

determining that a path leaves a mapped portion of a luminal network of a patient before reaching a target, at least one computer-readable memory having stored thereon a model of the mapped portion of the luminal network, a position of the target with respect to the model, and the path along at least a portion of the model from an access point to the target;

determining a current location of the instrument based on a weight given to at least a first modality, the first modality derives a location based on location data received from a set of one or more location sensors and the mapped portion of the model, the instrument is configured to be driven through the luminal network;

determining, based on the current location, that a distal end of the instrument is within a threshold range of a point at which the path leaves the mapped portion of the luminal network;

in response to determining that the distal end of the instrument is within the threshold range of the point at which the path leaves the mapped portion of the luminal network, updating the current location of the instrument based on a reduction of the weight given to the first modality; and commanding a robotic arm to move the instrument within the luminal network based on the updated location of the instrument.

24. The method of claim 23, wherein:

the model comprises a plurality of segments, the determination that the path leaves the mapped portion of the luminal network before reaching the target comprises determining that the path leaves the mapped portion of the luminal network from a first segment of the model, and the method further comprises determining that the instrument is located within a second segment adjacent to the first segment and located along the path, and the updating of the current location of the instrument based on the reduction of weight given to the first modality is further in response to determining that the instrument is located within the second segment.

25. The method of claim 24, further comprising:

the determination that the path leaves the mapped portion of the luminal network before reaching the target further comprises determining that the instrument is within a threshold distance from the second segment, and the updating of the current location of the instrument based on the reduction of weight given to the first modality is further in response to determining that the instrument is within the threshold distance from the second segment.

26. The method of claim 24, further comprising:

determining, based on the current location, that the distal end of the instrument has returned to the mapped portion of the luminal network from outside of the mapped portion of the luminal network, and in response to determining that the distal end of the instrument has returned to the mapped portion of the luminal network from outside of the mapped portion of the luminal network, updating the current location of the instrument based on an increase in the weight given to the first modality.

27. The method of claim 26, wherein determining that the distal end of the instrument has returned to the mapped portion of the luminal network from outside of the mapped portion of the luminal network comprises:

determining a first location of the instrument at which the updating of the current location of the instrument was first based on the reduced weight given to the first modality, and determining that the instrument is retracted to the first location.

28. The method of claim 23, wherein:

the model comprises a plurality of segments, determining that the path leaves the mapped portion of the luminal network before reaching the target comprises determining that the path leaves the mapped portion of the luminal network from a first segment of the model, the method further comprises:

identify a location of one or more unmapped intersections between the first segment and one or more unmapped segments the luminal network; and determine that the current location of the instrument is within a defined distance from the location of the one or more unmapped intersections, and updating the current location of the instrument based on the reduction of weight given to the first modality is further in response to determining that the current location of the instrument is within the defined distance from the location of the one or more unmapped intersections.

29. The method of claim 23, further comprising:

in response to determining that the current location of the instrument is within the threshold range of the point, entering a path tracing mode, and when in the path tracing mode, displaying, on a user display, visual indicia indicative of previous locations of the instrument with respect to the model.

30. The method of claim 29, wherein the visual indicia are indicative of historical positions of the instrument within the luminal network.

* * * * *